(12) United States Patent
Yamamoto et al.

(10) Patent No.: US 8,449,828 B2
(45) Date of Patent: May 28, 2013

(54) BLOWER TYPE CHEMICAL DIFFUSING APPARATUS, AND CHEMICAL CARTRIDGE AND CHEMICAL IMPREGNATED BODY USED THEREFOR

(75) Inventors: Kazunori Yamamoto, Hatsukaichi (JP); Shinya Kawamura, Hatsukaichi (JP); Satoshi Yamasaki, Hatsukaichi (JP); Yasuharu Takei, Hiroshima (JP); Takao Jo, Hiroshima (JP)

(73) Assignee: Fumakilla Limited, Hiroshima (JP)

( * ) Notice: Subject to any disclaimer, the term of this patent is extended or adjusted under 35 U.S.C. 154(b) by 0 days.

(21) Appl. No.: 13/010,499

(22) Filed: Jan. 20, 2011

(65) Prior Publication Data
US 2011/0110827 A1 May 12, 2011

Related U.S. Application Data

(62) Division of application No. 10/583,616, filed as application No. PCT/JP2004/019702 on Dec. 22, 2004, now Pat. No. 7,887,760.

(30) Foreign Application Priority Data

| Dec. 25, 2003 | (JP) | 2003-429128 |
| Jan. 20, 2004 | (JP) | 2004-011929 |
| Apr. 20, 2004 | (JP) | 2004-124204 |
| Apr. 23, 2004 | (JP) | 2004-128463 |
| Apr. 27, 2004 | (JP) | 2004-130590 |
| Apr. 28, 2004 | (JP) | 2004-132745 |
| May 11, 2004 | (JP) | 2004-140754 |
| May 26, 2004 | (JP) | 2004-155498 |

(51) Int. Cl.
*A62B 7/08* (2006.01)
*A24F 25/00* (2006.01)
*A61L 9/04* (2006.01)
*A01G 27/00* (2006.01)
*B05B 3/08* (2006.01)

(52) U.S. Cl.
USPC .......... 422/122; 422/120; 422/123; 239/51.5; 239/56; 239/57; 239/145; 239/326

(58) Field of Classification Search
USPC ............. 422/120, 122–123; 239/51.5, 56–57, 239/145, 187, 326
See application file for complete search history.

(56) References Cited

U.S. PATENT DOCUMENTS

| 2,585,289 A | 2/1952 | Wallace |
| 3,043,739 A | 7/1962 | Giles et al. |

(Continued)

FOREIGN PATENT DOCUMENTS

| EP | 0 093 262 A1 | 11/1983 |
| EP | 0 161 217 A2 | 11/1985 |

(Continued)

OTHER PUBLICATIONS

U.S. Appl. No. 13/010,421; First Named Inventor. Kazunori Yamamoto; Title: "Blower Type Chemical Diffusing Apparatus, and Chemical Cartridge and Chemical Impregnated Body Used Therefor"; Filed: Jan. 20, 2011.

(Continued)

*Primary Examiner* — Michael Marcheschi
*Assistant Examiner* — Christopher Vandeusen
(74) *Attorney, Agent, or Firm* — Holtz, Holtz, Goodman & Chick, P.C.

(57) ABSTRACT

A chemical cartridge for a blower-type chemical diffusing apparatus includes a chemical-impregnated body including an air-permeable and liquid-absorptive sheet impregnated with a chemical, and a retainer receptacle for containing the chemical-impregnated body. The retainer receptacle includes a liquid pool recess formed at a central area thereof such that liquid chemical stored in the liquid pool recess is permeable towards a peripheral area of the sheet.

1 Claim, 55 Drawing Sheets

U.S. PATENT DOCUMENTS

| | | | |
|---|---|---|---|
| 3,343,664 A | 9/1967 | Poitras | |
| 3,964,684 A | 6/1976 | Schimanski | |
| 4,035,451 A | 7/1977 | Tringali | |
| 4,276,236 A | 6/1981 | Sullivan et al. | |
| 4,597,781 A | 7/1986 | Spector | |
| 4,630,775 A | 12/1986 | Mandon et al. | |
| 4,666,638 A | 5/1987 | Baker et al. | |
| 4,802,626 A | 2/1989 | Forbes et al. | |
| 4,857,240 A | 8/1989 | Kearnes et al. | |
| 4,928,881 A * | 5/1990 | Barlics et al. | 239/44 |
| 5,121,881 A * | 6/1992 | Lembeck | 239/44 |
| 5,250,265 A | 10/1993 | Kawaguchi et al. | |
| 5,342,584 A | 8/1994 | Fritz et al. | |
| 5,370,829 A | 12/1994 | Kunze | |
| 5,972,213 A | 10/1999 | Golan | |
| 6,224,655 B1 | 5/2001 | Messier | |
| 6,343,434 B1 | 2/2002 | Petti | |
| 6,346,143 B1 | 2/2002 | McGowan | |
| 6,524,375 B2 | 2/2003 | Brun | |
| 7,887,760 B2 | 2/2011 | Yamamoto et al. | |
| 2001/0035095 A1 | 11/2001 | Canfield | |
| 2002/0037244 A1 | 3/2002 | Takahashi et al. | |
| 2002/0157540 A1 | 10/2002 | Lynn | |
| 2002/0197186 A1 | 12/2002 | Murray | |
| 2002/0197187 A1 | 12/2002 | Murray | |
| 2003/0150199 A1 | 8/2003 | Tanaka et al. | |
| 2003/0160062 A1 | 8/2003 | Inoue et al. | |
| 2003/0175171 A1 | 9/2003 | Yamamoto et al. | |
| 2003/0192293 A1 | 10/2003 | Choi et al. | |
| 2004/0121111 A1 * | 6/2004 | Hurwitz | 428/76 |
| 2004/0159239 A1 | 8/2004 | Nagem | |
| 2011/0108633 A1 | 5/2011 | Yamamoto et al. | |
| 2011/0108634 A1 | 5/2011 | Yamamoto et al. | |
| 2011/0116977 A1 | 5/2011 | Yamamoto et al. | |

FOREIGN PATENT DOCUMENTS

| | | |
|---|---|---|
| EP | 0 925 717 A1 | 6/1999 |
| EP | 0 962 139 A1 | 12/1999 |
| EP | 1 162 096 A1 | 12/2001 |
| EP | 1 352 562 A1 | 10/2003 |
| FR | 1 596 401 A | 7/1970 |
| FR | 2 065 630 A1 | 8/1971 |
| FR | 2 082 708 A5 | 12/1971 |
| FR | 2 248 081 A1 | 5/1975 |
| FR | 2 782 271 A1 | 2/2000 |
| FR | 2 807 973 A1 | 10/2001 |
| GB | 1 272 564 A | 5/1972 |
| GB | 1 475 004 A | 6/1977 |
| JP | 53-14329 A | 2/1978 |
| JP | 5-219166 A | 8/1993 |
| JP | 10-094555 A | 4/1998 |
| JP | 3071760 U | 6/2000 |
| JP | 2001-095458 A | 4/2001 |
| JP | 2001-197856 A | 7/2001 |
| JP | 2003-009746 A | 1/2003 |
| JP | 2003-102361 A | 4/2003 |
| JP | 2003-102362 A | 4/2003 |

OTHER PUBLICATIONS

U.S. Appl. No. 13/010,544; First Named Inventor: Shinya Kawamura; Title: "Blower Type Chemical Diffusing Apparatus, and Chemical Cartridge and Chemical Impregnated Body Used Therefor"; Filed: Jan. 20, 2011.

U.S. Appl. No. 13/010,592; First Named Inventor: Kazunori Yamamoto; Title: "Blower Type Chemical Diffusing Apparatus, and Chemical Cartridge and Chemical Impregnated Body Used Therefor"; Filed: Jan. 20, 2011.

Extended European Search Report (EESR) dated Dec. 8, 2010 (in English) in counterpart European Application No. 10179287.7.

Extended European Search Report (EESR) dated Dec. 8, 2010 (in English) in counterpart European Application No. 10179292.7.

* cited by examiner

F I G. 30
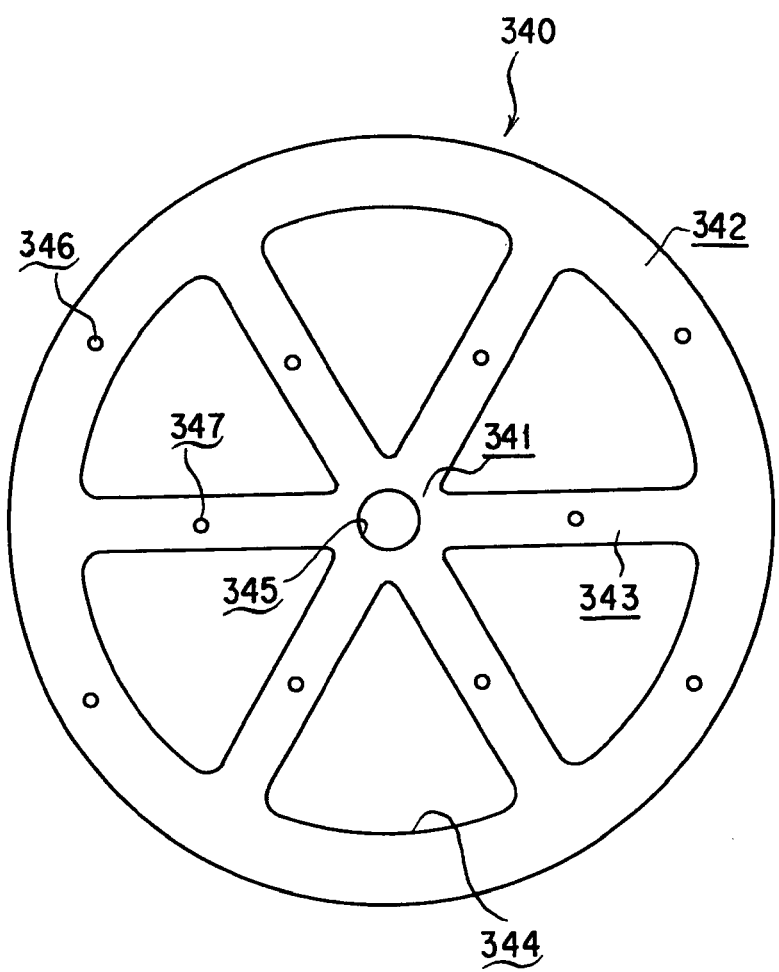

FIG. 31
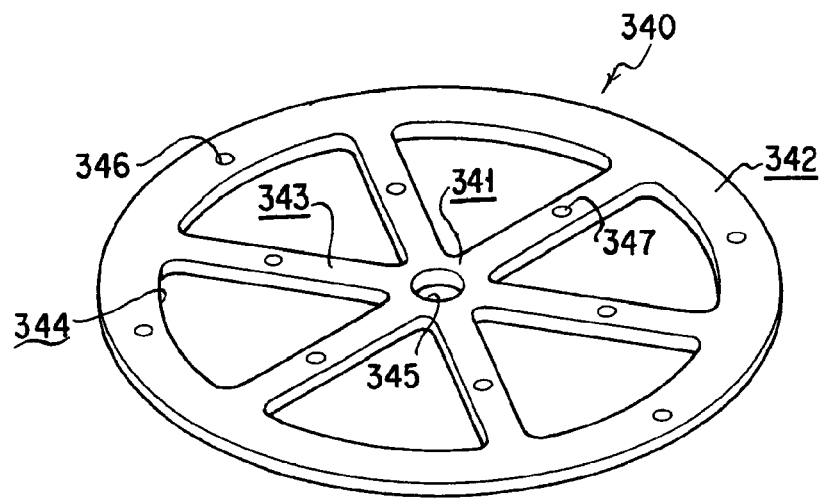
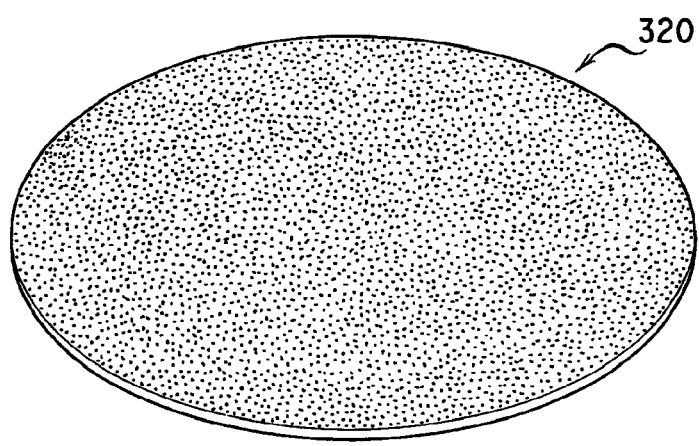
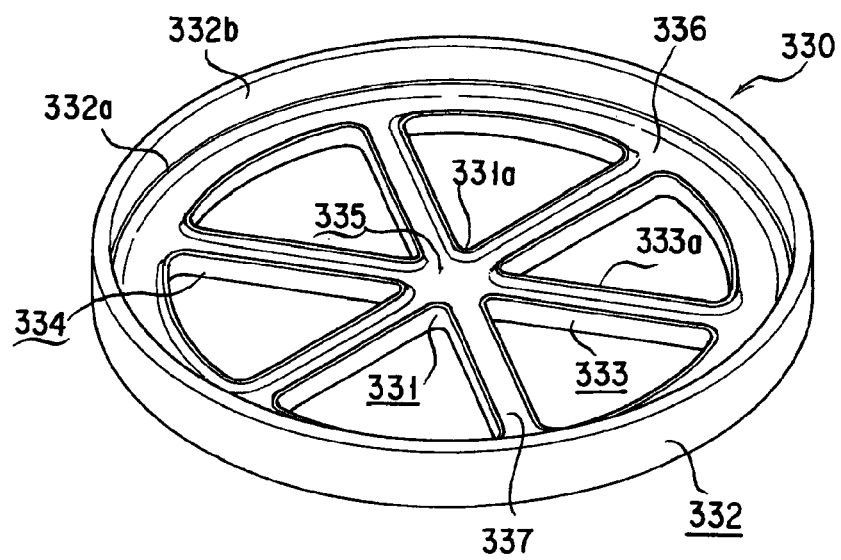

FIG. 35
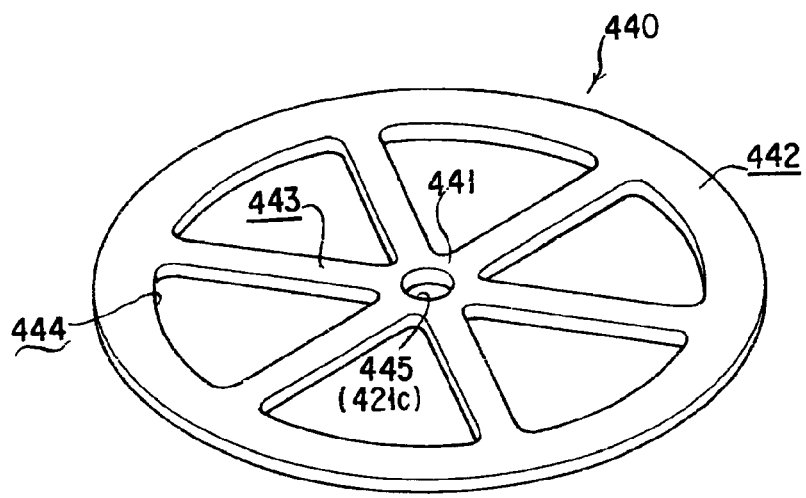
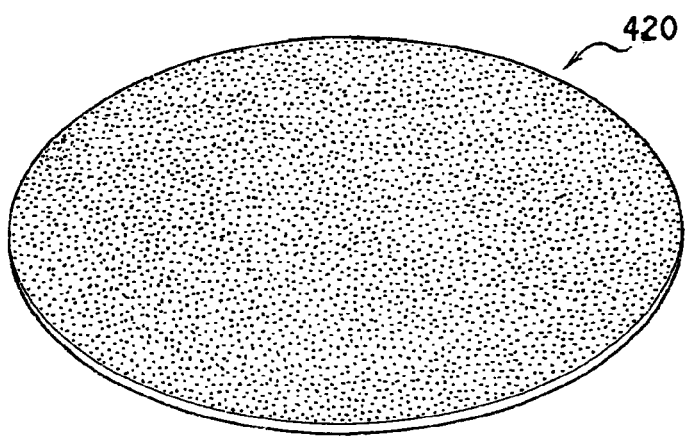
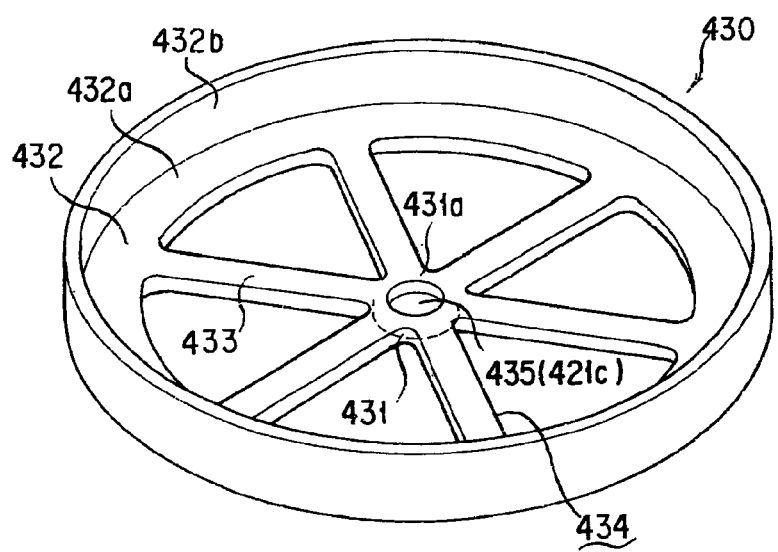

BLOWER TYPE CHEMICAL DIFFUSING APPARATUS, AND CHEMICAL CARTRIDGE AND CHEMICAL IMPREGNATED BODY USED THEREFOR

This is a Divisional Application of U.S. application Ser. No. 10/583,616, filed Dec. 4, 2006, now issued as U.S. Pat. No. 7,887,760, which is a U.S. National Phase Application under 35 USC 371 of International Application PCT/JP2004/019702, filed Dec. 22, 2004, the entire contents of both of which are incorporated herein by reference.

TECHNICAL FIELD

The present invention relates to a blower type chemical diffusing apparatus for volatilizing and diffusing a volatile chemical such as an insect pest control agent as an insecticide, miticide, vermin or pest repellent, vermin growth retardant or sucking inhibitor, an aromatic, deodorant, or germicide, by the force of an airflow or wind generated by an air blower.

The present invention also relates to a blower type chemical diffusing apparatus as a blower type vermin or insect pest control apparatus for applying airflow to a chemical receptacle retaining a vermin or insect control component to emanate or diffuse such control component together with air into an atmosphere.

The present invention also relates to a blower type chemical diffusing apparatus as a blower type chemical emanating apparatus provided with a chemical receptacle charged with a volatile chemical serving as an insecticide, repellent, aromatic, deodorant, germicide or fungicide and an air blower whereby air is drawn through an air inlet port and air is emanated or diffused through an outlet port into an atmosphere together with such volatile chemical volatilizing from the chemical receptacle and occluded into air.

The present invention also relates to a chemical cartridge for retaining a volatile chemical such as an insect pest control agent, aromatic, deodorant or germicide and permitting such volatile chemical to be emanated or diffused into an atmosphere from the chemical cartridge when used in a blower type chemical diffusing apparatus.

The present invention also relates to a chemical impregnated body or member for retaining a volatile chemical such as an insect pest control agent, aromatic, deodorant or germicide and permitting such volatile chemical to be emanated or diffused into an atmosphere from the chemical cartridge when used in a blower type chemical diffusing apparatus.

BACKGROUND ART

There is known a blower type chemical diffusing apparatus as disclosed in JP 2002-291392 A.

Such a blower type chemical diffusing apparatus is provided in its body with an air blower, a chemical receptacle (chemical cartridge) and a power supply container wherein the air blower includes a fan and a motor, the chemical receptacle is stored with a volatile chemical and the power supply container contains a battery.

And, the motor is driven to rotate the fan, which causes air to flow through the chemical receptacle, which in turn volatilizes volatile chemical and diffuses it into an atmosphere.

With the volatile chemical and the battery becoming ineffective and ending their lives with its use, the conventional blower type chemical diffusing apparatus of the type described above is designed to make them replaceable for its continued use.

Thus, for example, the power supply container is designed to contain the battery replaceably and have the chemical receptacle replaceably mounted therewith and to be itself mounted replaceably in the apparatus body so that removing the power supply container from the apparatus body allows replacing the chemical receptacle and the battery.

This arrangement entails detachably interconnecting a plurality of members together to enable replacing the chemical receptacle and battery and thus makes the structure complicated and costly.

Also, the need to remove the power supply container from the apparatus body and then to take the chemical receptacle and battery out of the removed power supply container for replacement requires troublesome handling and gives rise to a chance that either the apparatus body or the power supply container may be lost while they are detached one from the other.

Further, the inability to connect the motor for the air blower mounted in the apparatus body to the battery received in the power supply container by any cord calls for a complicated structure for electrically connecting them together.

Further, a volume of chemical receptacle in the state where it fills a large number of particulate chemical impregnated bodies in a porous receptacle body must be large in thickness.

This requires that the apparatus body be large in thickness.

There is also known a blower type apparatus for controlling harmful insects as disclosed in JP 2001-197856 A.

Such an insect control apparatus includes a chemical receptacle retaining an insect control component or ingredient, a fan and a motor which are all contained in an apparatus body (in the form of a chamber) which in turn has an air inlet and an air outlet port wherein the rotation of the fan by means of the motor causes air to be drawn through the air inlet port, to strike the chemical receptacle and to issue through the air outlet port together with insect control ingredient into an atmosphere, thereby emanating or diffusing the insect control ingredient into the atmosphere.

A conventional insect control apparatus of this type to make its insect control function effective when it is carried on a user and used in the outdoors, has its body formed with a pair of air outlet ports facing upwards and downwards, respectively, so that when used carried on the user it causes air containing insect control ingredient to issue both upwards and downwards through the upward and downward facing air outlet ports, respectively.

A conventional insect control apparatus of this type having its apparatus body formed with upward and downward facing air outlet ports so that when used as carried on a waist of the user it can cause air containing insect control ingredient to issue selectively both upwards and downwards is designed to have insect control ingredient reach both the user's head and feet. With such a conventional insect control apparatus formed simply with such upward and downward facing outlet ports alone, however, it takes time the insect control ingredient reaches the user's head and feet and it is thus not possible to control harmful insect from the very beginning of use of the apparatus.

In an open space such as the outdoors where the apparatus is used, air currents produced by wind flow and movement of the user tend to fluctuate air flows discharged and prevent them from diffusing into target directions and may not protect the user from suffering from insect attack.

Also, in a blower type chemical diffusing apparatus as disclosed in JP 2004-24161 A which is designed to draw air through an air intake or suction port by an air blower and to cause chemical volatilizing from a chemical receptacle (chemical cartridge) to issue through an air discharge port together with air drawn, as shown in FIGS. 23 and 24 the apparatus body 241 is formed on its top with the suction port 242 for drawing air and on its two opposed sides with such air discharge ports 243 for emanating chemical entrained in air drawn. And, the suction port 242 on the top of the apparatus body 241 is provided with the chemical or chemical accommodating receptacle 244 in which the chemical is retained. This chemical receptacle 244 is formed in both its top and bottom with slits 245 opening in the form of annual rings (or annual growth rings of a tree) through which air is allowed to flow. Further, the apparatus body 241 is provided in its inside with the air blower 246 and has battery cells 247 received at two opposed sides of the air blower 246, respectively, as a power supply for moving the latter.

With the apparatus 241 made up in this way, the air blower 246 built therein to work energized by the battery cells 247 draws air from the suction port 242 at its top through the chemical receptacle 244 and causes air drawn into and past the chemical receptacle 244 while carrying chemical volatilizing there to emanate and diffuse through the air discharge ports 243 at its side faces into its environment.

On the other hand, the apparatus body 241 has a wearing belt 248 attached thereto to enable it to be worn on a user's wrist or the like. Such a wearing belt 248 is flexible, thin and elongate and with a buckle 249 at one of its ends with which the apparatus body 241 can be worn on the user's wrist or the like, thereby enabling the subject blower type chemical diffusing apparatus to be used fitted on the wrist or the like.

A conventional blower type chemical diffusing apparatus of this type thus requires it's apparatus body to include a chemical receptacle containing a volatile chemical, an air blower for diffusing chemical volatilizing from the chemical receptacle into the environment and further a battery as a power supply for energizing the air blower as the weightiest component. As a result, the apparatus body tends to become large in size and heavy in weight, giving rise to the chance that this makes the user feel it hard to use the apparatus. Especially in case the subject blower type chemical diffusing apparatus is used as worn on the wrist or the like, the user may feel it disagreeable with the feeling of its size and weight.

There is also known a blower type chemical diffusing apparatus as disclosed in JP 2002-291392 A.

In a blower type chemical diffusing apparatus of this type, its apparatus body includes an air blower, a chemical cartridge and a power supply container wherein the air blower has a fan and a motor, the chemical cartridge comprising a porous receptacle that contains a large number of particulate chemical impregnated bodies impregnated with a chemical, and the power supply container accommodates a battery.

And, it is so designed that rotating the fan with the motor causes air to pass through the receptacle and to emanate with chemical entrained therein into the atmosphere.

A conventional chemical cartridge as mentioned above comprises a porous receptacle that needs to contain a large number of particulate chemical impregnated bodies impregnated with a chemical must be large in thickness, requiring such a chemical cartridge to be large in thickness.

As a result, a blower type chemical diffusing apparatus of this type requiring a chemical cartridge, an air blower and battery cells to be all mounted within its apparatus body must become large in thickness as a whole.

Further, the conventional chemical cartridge as mentioned above comprises a porous receptacle containing a large number of particulate chemical impregnated bodies impregnated with a chemical, and the chemical in these particulate chemical impregnated bodies upon volatilization is entrained in air passed through the receptacle and emitted progressively into the atmosphere. When the chemical impregnated in the chemical impregnated bodies is depleted, the receptacle as it carries the particulate chemical impregnated bodies is thrown away as waste.

Such chemical cartridges which thus require that they when used out be thrown away as waste, are unfavorable under social circumstances nowadays such as waste and energy-saving problems.

There is also known a chemical impregnated body as disclosed in JP 2001-200239 A.

This chemical impregnated body comprises a plurality of chemical carrying nets composed of twisted yarn and laid one over another wherein each of the nets is impregnated with a chemical.

A conventional chemical impregnated body as mentioned above in which a plurality of nets are laid one on another, can be made, but may make the user feel it hard to use this chemical impregnated body as having a plurality of nets laid one on another and moreover may cause a user's hand to be stained with chemical from such a chemical impregnated body when held by the hand.

When the chemical impregnated in the nets is depleted, the nets are thrown away as waste like the chemical cartridge mentioned above. Such chemical impregnated body is unfavorable under social circumstances nowadays such as waste and energy-saving problems.

There is also known a chemical cartridge as disclosed in JP Design Registration No. 1173150.

This chemical cartridge comprises a receptacle defined by an outer casing having an opening and an inner casing having an opening wherein a large number of particulate chemical impregnated bodies impregnated with a chemical are received in a space between the outer and inner casings.

This chemical cartridge is designed to contain particulate chemical impregnated bodies impregnated with a chemical in a limited portion of the volume of the cartridge through which air is passed to entrain volatilizing chemical therein for diffusion into the atmosphere, is limited in the amount of chemical it can contain per unit volume and if this is made larger must be larger in diameter, thus making the cartridge body larger in size as a whole.

As a result, such a chemical cartridge requires a large space for its accommodation in a blower type chemical diffusing apparatus and thus makes the apparatus body large in size.

JP 2002-291392 previously mentioned also discloses a chemical impregnated body which uses a large number of carrier particles impregnated with a chemical and retained in a porous receptacle.

As a result, this requires that the receptacle be large in size and hence in thickness as well, making here again the body of a blower type chemical diffusing apparatus as a whole large in size.

In contrast, the chemical impregnated body if made in the form of a sheet as a carrier impregnated with a chemical and thereby retaining the chemical can be sufficiently thin that it holds the apparatus body thin enough.

However, a chemical impregnated body so made in the form of a sheet is so weak in rigidity that it cannot sustain itself its given shape. Thus, an attempt is made to sustain a given shape of a chemical impregnated body by supporting it in its central, outer peripheral and intermediate regions with its retainer receptacle.

These regions of the chemical impregnated body supported by the retainer receptacle are large in surface area and become entirely useless in serving to emanate and diffuse chemical impregnated in these regions because air cannot pass through the regions.

In this connection there is also known a chemical impregnated body as disclosed in JP H11-92303 A which is in the form of a honeycomb impregnated with a chemical that is stronger in rigidity and larger in the amount containing chemical per unit volume than the sheet-like chemical impregnated body.

However, whichever of sheet-like or honeycomb type, such a conventional chemical impregnated body once it is used out or spent in a blower type chemical diffusing apparatus in diffusing chemical into an atmosphere must be thrown away as waste.

Such a conventional chemical impregnated body of throwaway type is unfavorable under social circumstances nowadays at waste and resource-saving standpoints.

For this reason, it is conceivable to make spent chemical impregnated body reusable by impregnating it again with chemical to have it retain the chemical again.

Then, while it may be possible to make reusable a spent chemical impregnated body especially if of sheet type by dripping to impregnate it with chemical and have it retain chemical again, impregnating a honeycomb type impregnated body, shaped to include a large number of cores, with chemical requires dipping the honeycomb body in a container filled with a large quantity of chemical or continuing to supply it with a large quantity of chemical and for a time period enough to achieve required impregnation. Not only does this require such a large quantity of chemical but also there will a specialized facility become mandatory in dealing with the chemical.

Thus, while a large number of chemical impregnated bodies can be re-impregnated with chemical and thereby made reusable successively as in a factory or manufacturing plant without difficulty to meet these requirements, it is altogether impractical for an individual user to attempt to make a conventional spent chemical retainer or cartridge reusable because a surplus chemical is wasted and cannot be dealt with.

DISCLOSURE OF THE INVENTION

It is an object of the present invention to provide a blower type chemical diffusing apparatus that is simple in structure and low in cost to enable a chemical cartridge and a battery to be renewed, that is easy to operate in renewing a chemical cartridge and a battery, that facilitates electrical connection of the battery to the motor in the blower and yet that is thinned as a whole.

It is another object of the present invention to provide a blower type chemical diffusing apparatus that configures the air discharge port so as to discharge air forcibly in desired directions and, when the apparatus is used worn on the user's waist, to cause the harmful insect control component to reach the head and feet quickly, thereby making it effective to control harmful insects from the beginning of use of the apparatus.

It is still another object of the present invention to provide a blower type chemical diffusing apparatus that is smaller in size and light in weight and can be used comfortably by the user without feeling it disagreeable.

It is a further object of the present invention to provide a chemical cartridge that is thinned, that can sustain its given shape, that is easy to handle and free from contaminating a use's hand and which when used out can be refilled with chemical and can be reused over and again.

It is still a further object of the present invention to provide a chemical cartridge that is large in amount of chemical per unit volume and that can be smaller in overall size.

It is yet a further object of the present invention to provide a chemical impregnated body that can hold its given shape, that can emit the chemical it retains into an atmosphere efficiently and which when depleted of chemical can be refilled with chemical by a user easily.

There is provided in accordance with the present invention in a first aspect thereof a blower type chemical diffusing apparatus having an apparatus casing body, an air blower, a chemical cartridge and a battery, characterized in that the apparatus casing body comprises a first side and a second side counterpart casing body openably coupled together by a hinge, the first side casing body having a blower mounting recess, an airflow section and a battery accepting recess, the second side casing body having an airflow section spaced from the airflow section in the first side casing body; the air blower has a fan adapted for rotation by a motor, the fan and the motor being mounted in the blower mounting recess; the chemical cartridge is disposed between the air blower in the first side casing body and the airflow section in the second side casing body; the battery is removably accepted in the battery accommodating recess; the blower mounting and battery accommodating recesses are spaced apart from each other in a planar direction and positioned not to overlap in a direction of their thicknesses; and the chemical cartridge contains a chemical impregnated body having a carrier in the form of a sheet impregnated with a chemical.

A blower type chemical diffusing apparatus in this aspect of the present invention, which permits the chemical cartridge and the battery in the first side counterpart casing body to be taken out and reloaded simply by turning open the second side counter part casing body about the hinge from the first side counterpart casing body, is simple and reduced in cost structurally in enabling these consumables to be renewed.

Since opening the second side counter casing body simply allows the chemical cartridge and the battery to be replace, their replacement is easy. Moreover, with these two counterpart casings then held coupled together, there can either of them be lost from the other by no means.

Moreover, since the motor and the battery for the fan is positioned in the first side counter part casing body as a common casing, it is altogether easy to electrically connect them; the motor and the battery can easily be connected electrically.

Further, since the chemical cartridge is thin and the chemical cartridge and the battery are positioned without overlapping in a direction of their thicknesses, the entire apparatus is thinned.

In a blower type chemical diffusing apparatus as set forth above, the apparatus casing body may be formed with a hook engagement section to which a hook of a hanging aid can be engaged and a hole in which a fitting section of hanging aid can be fitted.

This feature allows the apparatus to be used while it is hung or left to stand on a table or the like.

The present invention also provides in a second aspect thereof a blower type insect pest control apparatus including: an apparatus casing body having an air inlet port and a first and a second air discharge port, and a chemical receptacle, a fan and a motor in the apparatus casing body, the chemical receptacle retaining a chemical impregnated body impregnated with an insect pest control component, whereby rotating the fan by the motor allows air to be drawn through the air inlet port and air drawn to strike on the chemical impregnated body in the chemical receptacle and air entraining insect pest control component therein from the chemical impregnated body to emanate and diffuse into an environmental atmosphere, characterized in that: the first and second air discharge ports are each in the form of a hole having a radial length and inclined to a circumferential direction in which the fan rotates whereby when the apparatus is used with the apparatus casing body worn on a user, air is discharged upwards through the first air discharge port and downwards through the second air discharge port.

A blower type insect pest control apparatus in this aspect of the present invention, which permits air containing an insect pest control component to be forcibly discharged through the first and second air discharge ports, is advantageously applicable to where the apparatus is used with its casing body worn on the user's waist in that air containing an insect pest control component is allowed to issue forcibly through the first and second air discharge ports and thus allowed to reach the user's head and feet quickly.

This provides an apparatus that acts efficiently from the very beginning of its use.

In a blower type insect pest control apparatus as set forth above, the first and second air discharge ports may each be in the form of a hole that communicates its inner inlet opposed to the fan to its outer outlet open in an outer face of the apparatus casing body and wherein the hole has an upstream side guide face connecting an upstream side inlet hole edge of the inner inlet and an upstream side outlet hole edge of the outer outlet continuously to each other and a downstream side guide face connecting downstream side inlet hole edge of the inner inlet and a downstream side outlet hole edge of the outer outlet continuously each other, the upstream side and downstream side guide faces being each inclined to a circumferential direction in which the fan rotates.

With the upstream side and downstream side guide faces each inclined towards a circumferential direction in which the fan rotates according to this feature, air containing the insect pest control component can be flushed not only forcibly but also smoothly.

In a blower type insect pest control apparatus as set forth above, the apparatus casing body may be configured to comprise a base member having the first and second air discharge ports and a fan accommodating chamber, a cover member having the air inlet port and removably attached to the base member at one of its sides in a direction of its thickness and a chemical accommodating chamber disposed between the base and cover members and open to the fan accommodating chamber. Then, the base member may be formed with a motor accommodating chamber and a battery accommodating chamber which are open in a rear face of the base member at its opposite side to the cover member; and the motor and battery accommodating chambers may be adapted to accommodate the motor and the battery, respectively, and positioned so that the motor and the battery do not overlap in a direction of thickness of the base member.

This feature permits the cover member to be removed to enable the chemical receptacle to be removed. Also, since the motor and the battery are arranged not to over lap in a direction of the thickness of the base member, the entire apparatus can be thinned.

In a blower type insect pest control apparatus as set forth above, the apparatus casing body may further be formed with a third air discharge port for discharging air entraining insect pest control component therein, the third air discharge port being in the form of a hole having a radial length and being inclined to a circumferential direction in which the fan rotates whereby when the apparatus is used with the apparatus casing body worn on a user, air is discharged obliquely upwards or obliquely downwards through the third air discharge port.

According to this feature, since air containing the insect pest control component is allowed to issue through the third air discharge port obliquely upwards or obliquely downwards, it is possible to send the insect pest control component more to either the head or the feet than to elsewhere.

In a blower type insect pest control apparatus as set forth above, the third air discharge port may be in the form of a hole that communicates its inner inlet opposed to the fan to its outer outlet open in an outer face of the apparatus casing body and wherein the hole has an upstream side guide face connecting an upstream side inlet hole edge of the inner inlet and an upstream side outlet hole edge of the outer outlet continuously to each other and a downstream side guide face connecting a downstream side inlet hole edge of the inner inlet and a downstream side outlet hole edge of the outer outlet continuously each other, the upstream side and downstream side guide faces being each inclined to a circumferential direction in which the fan rotates.

According to this feature, air containing the insect pest control component can be discharge not only forcibly but also smoothly.

In a blower type insect pest control apparatus as set forth above, the apparatus casing body is formed with a subsidiary air discharge port adapted to discharge air laterally when the apparatus is used with the apparatus casing member worn on a user, thereby enabling the apparatus to emit air in all directions with upwards and downwards inclusive.

According to this feature, when the apparatus is used as worn on the user, the insect pest control component can be diffused evenly around the user.

In a blower type insect pest control apparatus as set forth above, the subsidiary air discharge port may be larger in air resistance than the first and second air discharge ports or the first, second and third air discharge ports.

This feature is advantageously applicable where the apparatus is used as worn on the user's waist in that air containing the insect pest control component can be emitted less forcibly but adequately laterally of the user and at the same time forcibly enough to its head and feet.

In a blower type insect pest control apparatus as set forth above, the subsidiary air discharge port may be in the form of a hole that communicates its inner inlet opposed to the fan to its outer outlet open in an outer face of the apparatus casing body and wherein the hole has an upstream side guide face connecting an upstream side inlet hole edge of the inner inlet and an upstream side outlet hole edge of the outer outlet continuously to each other and a downstream side guide face connecting a downstream side inlet hole edge of the inner inlet and a downstream side outlet hole edge of the outer outlet continuously each other, the upstream side and downstream side guide faces being each inclined to a circumferential direction in which the fan rotates. Then, the subsidiary air discharge port ma be less open in the direction of rotation of the fan than the first and second air discharge ports or the first, second and third air discharge ports.

According to this feature, air can be discharged forcibly through the first and second or the first, second and third air discharge ports without fail while air is discharged less forcibly through the subsidiary air discharge port without fail.

The present invention also provides in another aspect thereof a blower type chemical diffusing apparatus having an air blower and a chemical receptacle stored with a volatile chemical, characterized in that it comprises: an apparatus casing body wherein air is drawn by the fan through an air inlet port and discharged through an air discharge port while entraining chemical from the chemical receptacle therein; a power casing body separated from the apparatus casing body for containing a power supply for the air blower in the apparatus casing body; and a connection cord for connecting the apparatus casing body and the power casing body to each other and for electrically energizing the air blower in the apparatus casing body from the power supply in the power casing body.

A blower type chemical diffusing apparatus in this aspect of the present invention is designed to separate the power supply (battery) section as the weightiest component from the other components and to include them separately in a power casing body and an apparatus casing body and thereby to reduce the apparatus casing body in both size and weight as can conveniently be worn on the user's wrist. Then, the power casing body can be worn separately, e.g., in a pocket in a pant, trouser or suit, thereby permitting the apparatus to be used comfortably while relieving the user from feeling of disagreeableness it has had when wearing the conventional apparatus large in size and heavy in weight. In addition, a connection cord as set forth is conveniently provided.

In a blower type chemical diffusing apparatus as set forth above, a connection cord as set forth may advantageously be such that it can be removably attached to the apparatus casing body and/or the power casing body.

This feature allows the connection cord first connected to only either or neither of the apparatus and power casing bodies to be attached to the other or both only after they are fitted on, thereby facilitating their individual fitting operations markedly.

In a blower type chemical diffusing apparatus as set forth above, it may have a fitting means for fitting the apparatus casing to an object to be fitted.

In a blower type chemical diffusing apparatus as set forth above, it may have a fitting means for fitting the power casing to an object to be fitted.

In a blower type chemical diffusing apparatus as set forth above, it may have a fitting means for fitting the connection cord to an object to be fitted.

These features allow the blower type chemical diffusing apparatus to be readily set up by suitably fitting the apparatus casing body, the power casing body and the connection cord individually.

The present invention also provides in another aspect thereof a chemical cartridge, characterized in that it comprises: a chemical impregnated body in the form of an air permeable and liquid absorptive sheet impregnated with a chemical; a retainer receptacle for retaining the chemical impregnated body, the retainer receptacle having a hold section for holding an upper and a lower face of the chemical impregnated body across them and an air passage section through which air flows; and a space formed between hold section and chemical impregnated body and opening to an outside through an airflow section formed in the hold section.

According to this aspect of the present invention, a chemical cartridge is provided that is thinned by utilizing a chemical impregnated body that is thin in the form of a sheet held by a retainer receptacle which also serves to sustain its given shape and to protect the hand from contamination by chemical.

Also, a volume of chemical retained in those areas of a chemical impregnated body where it is held by the retainer receptacle and where there is no direct flow of air is admitted into the space stated where it is entrained in air flowing there and then discharge into the environmental atmosphere. Hence, substantially no volume of chemical retained in the chemical impregnated body will become useless.

In a chemical cartridge as set forth above, the hold section may have: a recess formed where the hold section is contacting a lower face of the chemical impregnated body; a space formed between the recess and a lower face of the chemical impregnated body; and an airflow hole formed, where the hold section is contacting an upper face of the chemical impregnated body, so that it is opposed to recess, thereby providing an air flow section.

According to this makeup of the chemical cartridge, the recess can be used to pool a liquid chemical poured into it through the airflow hole. The liquid chemical pooled in the recess is allowed to permeate into the chemical depleted body progressively and thereby to regenerate into a chemical impregnated body.

The present invention provides in still another aspect thereof a chemical cartridge, characterized in that it comprises: a chemical impregnated body in the form of an air permeable and liquid absorptive sheet impregnated with a chemical; and a retainer receptacle having a receptacle base member and a cover member for holding chemical impregnated body wherein: the receptacle base member comprises a central support section, a peripheral support section and a plurality of intermediate support sections connecting the central support section to the peripheral support section to form an airflow passage section, the receptacle base member being formed with a recess in at least one of upper faces of the central, peripheral and intermediate sections and with a space between this recess and a lower face of the liquid impregnated body, cover member comprises a central hold section, a peripheral hold section and a plurality of intermediate hold sections connecting the central hold section and the peripheral hold section to each other to form an airflow passage section, the cover member being formed with an airflow hole in at least one of the central, peripheral and intermediate hold sections so that it is opposed to the recess, whereby the receptacle base member and cover member can detachably be fitted with and coupled to each other to allow air to flow through the airflow passage section in the receptacle base member and the airflow passage section in the cover member.

Here again, a chemical cartridge is provided that can be thin, that can keep a chemical impregnated body in its given shape and that can protect the hand from contamination by chemical.

Also, with its central, peripheral and intermediate sections held with the central support and hold section, the peripheral support and hold sections and the intermediate sections of the receptacle base and cover members, a thin chemical impregnated body can be firmed held and also is easy to handle and maintain.

Moreover, a volume of chemical retained in at least one area of a chemical impregnated body where it is held by a support and a hold section and where there is no direct flow of air is admitted into the recess stated where it is entrained in air flowing there and then discharge into the environmental atmosphere. Hence, substantially no volume of chemical retained in the chemical impregnated body will become useless.

The recess, here again, can be used to pool a liquid chemical poured into it through the airflow hole. The liquid chemical pooled in the recess is allowed to permeate into the chemical depleted body progressively and thereby to regenerate into a chemical impregnated body.

In a chemical cartridge as set forth above, the receptacle base member may be formed with a recess in the central support section and annular recess in the peripheral support section.

According to this feature, the annular recess in the peripheral support section allows liquid chemical to permeate into the chemical depleted body from its whole periphery uniformly over its entire area.

In a chemical cartridge as set forth above, the central, peripheral and intermediate support sections are identical in shape and size to the central, peripheral and intermediate hold sections, respectively, so that the airflow passage sections are identical in shape and size to each other.

This makeup allows air to flow smoothly over the airflow passage sections of both the receptacle base and cover members and thus chemical in the chemical impregnated body to emanate and diffuse into the environmental atmosphere smoothly and efficiently.

The present invention also provides in a further aspect thereof a chemical cartridge characterized in that it comprises a chemical impregnated body in the form of an air permeable and liquid absorptive sheet impregnated with a chemical and a retainer receptacle for containing the chemical impregnated body wherein the retainer receptacle is formed in a central area thereof with a liquid pool recess such that liquid chemical stored in the liquid pool recess is allowed to permeate towards a peripheral area of the sheet.

Such a chemical cartridge is, here again, advantageous in that it after use can be refilled. To this end, liquid chemical is supplied into the recess in the central area of the retainer receptacle, and liquid chemical pooled in this recess of the retainer receptacle is allowed to permeate towards its periphery and then into the sheet body uniformly over its entire area.

A chemical cartridge can thus be reused over and again.

Also, by being positioned at a center of the retainer receptacle, the liquid pool recess in no way impedes the airflow from the fan which can thus be used without waste and exploited efficiently to diffuse the chemical into the environmental atmosphere.

Further, with the chemical impregnated body thin in the form of a sheet retained by a retainer receptacle, the chemical cartridge can be thinned.

Moreover, a chemical receptacle as defined above is adequate in keeping a chemical receptacle in its given shape and is also free from contaminating the hand with chemical.

In a chemical cartridge as set forth above, the retainer receptacle may be formed in a peripheral area with a liquid pool recess such that liquid chemical stored in the liquid pool recess is allowed to permeate towards a central area of the sheet. The retainer receptacle is formed in a peripheral area with a liquid pool recess such that liquid chemical stored in the liquid pool recess is allowed to permeate towards a central area of the sheet.

This makeup allows liquid chemical supplied into stored in the liquid pool recess in a central area of a body to permeate towards its peripheral are and liquid chemical supplied into and stored in the peripheral area to permeate towards the central area. Thus, even a large body can be impregnated with chemical relatively quickly.

In a chemical cartridge as set forth above, the retainer receptacle for containing the chemical impregnated body may comprise a receptacle base member and a cover member; the receptacle base member comprises a central support section, a peripheral support section and a plurality of connecting sections connecting the central and peripheral support sections to each other to form an airflow passage section; the cover member comprises a central hold section, a peripheral hold section and a plurality of connecting sections connecting the central and peripheral hold sections to each other to form an airflow passage section; a central liquid pool recess formed of a recess formed in the central support section and a supply port formed in central hold section; and a peripheral liquid pool recess formed of a peripheral recess formed in the peripheral support section and a peripheral supply section formed in the peripheral hold section.

With its central and peripheral sections held between the receptacle base and cover members here, the chemical impregnated body can be held firmly in a chemical cartridge, facilitating its handling and maintenance.

The present invention also provides in a further aspect thereof a chemical cartridge characterized in that it comprises: a chemical impregnated body in the form of a sheet and a retainer receptacle containing the chemical impregnated body wherein: the chemical impregnated body comprises a carrier in the form of an air permeable and liquid absorptive sheet having a localized high liquid retention region and impregnated with a chemical.

Here, with the chemical impregnated body being thin in the form of a sheet and held by its retainer receptacle, a chemical cartridge that is easy to handle can be provided.

A chemical cartridge so constructed is, here too, advantageous in that when its chemical is depleted after use the career can be re-supplied with chemical in the high liquid retention region. Liquid chemical impregnated in the high liquid retention region of the career is then allowed to permeate progressively over into entire body, thereby regenerating it into a fresh chemical impregnated body. A chemical cartridge can thus be used over and again.

Moreover, the career can accept a large quantity of liquid chemical at its high liquid retention region at a time. Liquid chemical supplied into the high liquid region can then permeate into it progressively over its entire area. Thus, there is regenerated a body uniformly impregnated with and retaining chemical.

In a chemical cartridge as set forth above, a portion of the carrier may be made larger in thickness than its remaining portions to constitute the high liquid retention region.

So made, the high liquid retention region higher in height can provide a sign that can be visually seen to if liquid chemical has been supplied.

The present invention provides in an another aspect thereof a chemical cartridge characterized in that it comprises a chemical impregnated body in the form of a pleated flat sheet material having a large number of pleats impregnated with a chemical, the pleats are formed by alternating mountain fold and valley fold of the sheet material at certain widths, the sheet material itself being air permeable and liquid absorptive, the pleated sheet material having a peripheral area jointed to prevent the pleats from getting out of shape.

With a chemical cartridge so made its chemical impregnated body can retain an increased amount of chemical per unit volume and the cartridge itself can thus be made smaller in size.

In particular, a chemical cartridge that retains a large amount of chemical but is thin can thus be provided.

A pleated sheet material whose periphery is processed to prevent the pleats from getting out of shape allows air to flow sub substantially uniformly over its entire area and thus chemical to diffuse substantially uniformly from the entire chemical impregnated body.

A chemical cartridge as set forth above may further comprise a fixture for holding a peripheral area of the chemical impregnated body.

A chemical cartridge as set forth above may further comprise a receptacle containing the chemical impregnated body and having an airflow section.

Then, with the fixture or receptacle that can be held by the hand a chemical cartridge can be provided that is easy to handle while protecting the hand from contamination by chemical retained by the chemical impregnated body.

The present invention also provides in another aspect thereof a chemical cartridge characterized in that it comprises: a chemical impregnated body in the form of a pleated flat sheet material having a large number of pleats impregnated with a chemical, the pleats are formed by alternating mountain fold and valley fold of the sheet material at certain widths, the sheet material itself being air permeable and liquid absorptive; and a fixture for holding a peripheral area of the pleated sheet material with that area squeezed to keep the pleats not getting out of shape.

With a chemical cartridge so made its chemical impregnated body can retain an increased amount of chemical per unit volume and the cartridge itself can thus be made smaller in size.

In particular, a chemical cartridge that retains a large amount of chemical but is thin can thus be provided.

Also, with its peripheral area squeezed to keep the pleats not getting out of shape, the pleated sheet material allows air to flow substantially uniformly over its area and thus the chemical to diffuse substantially uniformly from the entire chemical impregnated body.

Further, with the fixture that can be held by the hand, a chemical cartridge can be provided that is easy to handle while protecting the hand from contamination by chemical.

Moreover, with its peripheral area squeezed with the fixture to keep the pleats not getting out of shape, the pleated sheet material need not be jointed separately and can be manufactured with greater easiness.

The present invention also provides in a further aspect thereof a chemical cartridge characterized in that it comprises: a chemical impregnated body in the form of a pleated flat sheet material having a large number of pleats impregnated with a chemical, the pleats are formed by alternating mountain fold and valley fold of the sheet material at certain widths, the sheet material itself being air permeable and liquid absorptive; and a receptacle containing the chemical impregnated body and having an airflow section.

With a chemical cartridge so made its chemical impregnated body can retain an increased amount of chemical per unit volume and the cartridge itself can thus be made smaller in size.

In particular, a chemical cartridge that retains a large amount of chemical but is thin can thus be provided.

Further, with the receptacle that can be held by the hand, a chemical cartridge can be provided that is easy to handle while protecting the hand from contamination by chemical.

The present invention also provides in yet another aspect thereof a chemical cartridge characterized in that it comprises: a chemical impregnated body in the form of a pleated flat sheet material having a large number of pleats impregnated with a chemical, the pleats are formed by alternating mountain fold and valley fold of the sheet material at certain widths, the sheet material itself being air permeable and liquid absorptive, the pleated sheet material being deformable into a hollow cylindrical shape; and a receptacle configured to include an annular hollow and an axial hollow, to allow air to flow through these hollows, and to accept the chemical impregnated body in the annular hollow.

With a chemical cartridge so made its chemical retainer can retain an increased amount of chemical per unit volume and the cartridge itself can thus be made smaller in size.

In particular, a chemical cartridge that retains a large amount of chemical but is thin can thus be provided.

Further, with the receptacle that can be held by the hand, a chemical cartridge can be provided that is easy to handle while protecting the hand from contamination by chemical.

According to a chemical cartridge so constructed, a pleated sheet material which itself is liquid absorptive can, after use or depletion be, be refilled and thoroughly impregnated with liquid chemical; it can be reused over and again.

The present invention also provides in yet another aspect thereof a chemical impregnated body characterized in that it comprises: a honeycomb body having a large number of honeycomb cores open to a pair of opposed side faces thereof in a direction of its thickness and providing airflow passages parallel to the thickness direction; and a sheet body disposed adjacent to one of side faces over an entire area thereof wherein the honeycomb and sheet bodies are impregnated with a chemical.

A chemical impregnated body as mentioned above can sustain its given shape wherein a honeycomb body acts also to reinforce a body.

A honeycomb body through which air flows smoothly does not impede air flowing through a sheet body; the chemical retained in the honeycomb and sheet bodies can be diffused efficiently in to the environmental atmosphere.

When the honeycomb and sheet bodies are depleted of chemical, the sheet body can be supplied with chemical to allow the supplied chemical to permeate into the sheet body itself and also into the honeycomb progressively.

Thus, the user can readily regenerate a chemical impregnated body from a depleted body by simply a sheet body in the depleted body with chemical to allow the supplied chemical to permeate into the sheet and honeycomb bodies.

A chemical impregnated body as set forth above may further comprise a retainer receptacle for retaining therein honeycomb and sheet bodies and holding them in intimate contact with each other.

With a honeycomb and a sheet body brought together into intimate contact, liquid chemical supplied to the sheet body is allowed to permeate into the honeycomb body without fail.

In a chemical impregnated body as set forth above, the receptacle comprises a receptacle base member having a support section for supporting the sheet body; and a hold member for fitting engagement with the receptacle base member to hold the honeycomb and sheet bodies in intimate contact with each other.

According to this makeup, a honeycomb and a sheet body are brought into intimate contact without fail when the sheet body is supported from a support section of a receptacle base member which is then fitted with and thereby coupled to a hold member.

In a chemical impregnated body as set forth above, the support section is formed with a liquid chemical pool section and a chemical inlet port for supplying liquid chemical into the liquid chemical pool section.

This makeup facilitates supplying a honeycomb body with liquid chemical when liquid chemical is poured into a liquid chemical pool section through a supply inlet and the supplied liquid pooled is allowed to permeate into the sheet body over its entire area.

BRIEF DESCRIPTION OF THE DRAWINGS

The present invention will better be understood from the following detailed description and the drawings attached hereto showing certain illustrative forms of implementation of the present invention. In this connection, it should be noted that such forms of implementation illustrated in the accompanying drawings hereof are intended in no way to limit the present invention but to facilitate an explanation and understanding thereof. In the drawings.

FIG. 30 is a top plan view illustrating a cover member;

FIG. 31 is a broken perspective view of the chemical cartridge shown in FIG. 25;

FIG. 35 is a decomposed perspective view of the chemical cartridge shown in FIG. 34;

BEST MODES FOR CARRYING OUT THE INVENTION

Figure 1:
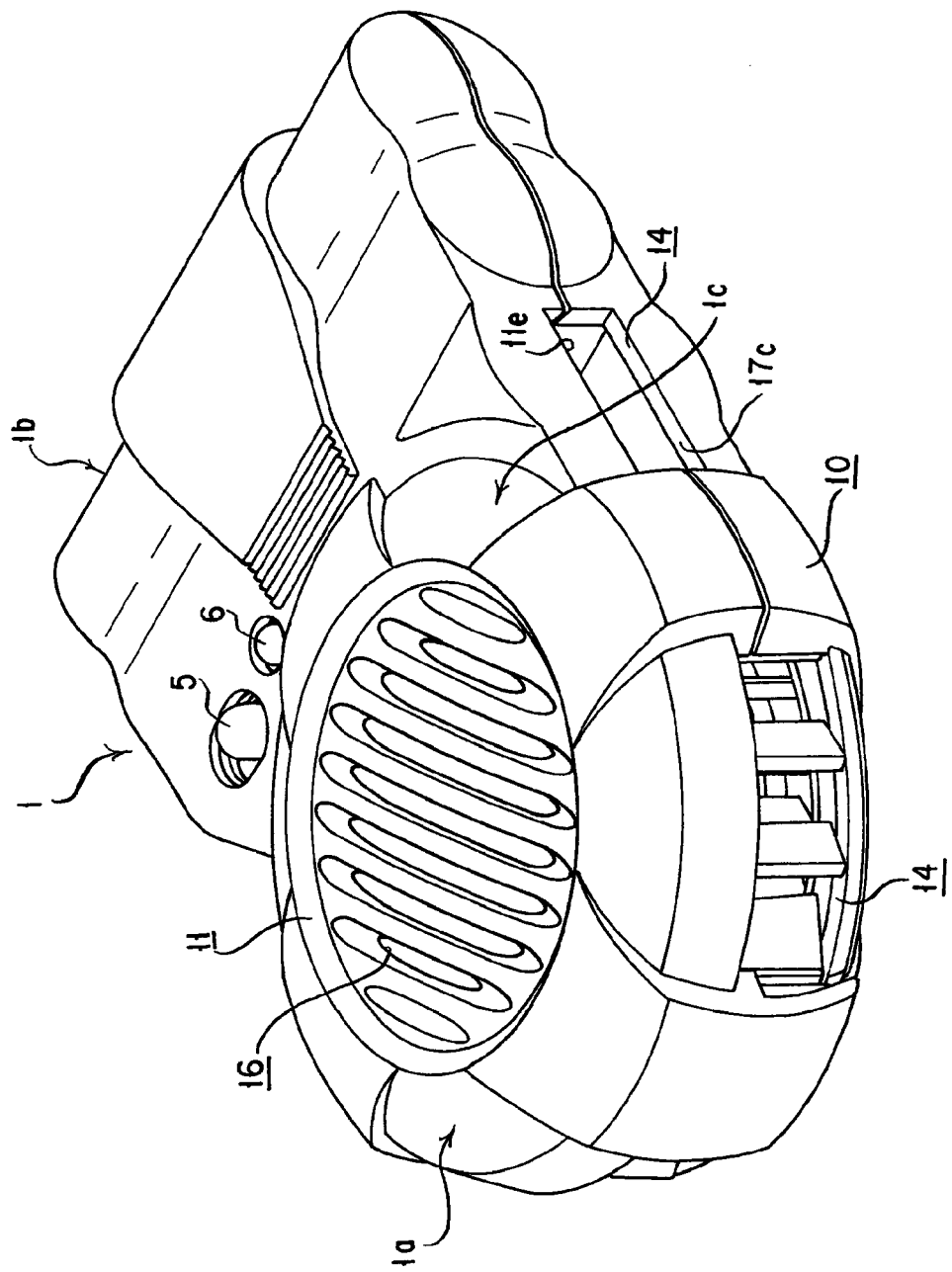
FIG. 1 is a perspective view illustrating a blower type chemical diffusing apparatus that represents a first form of implementation of the present invention, the apparatus being shown in its closed state.
Figure 2:
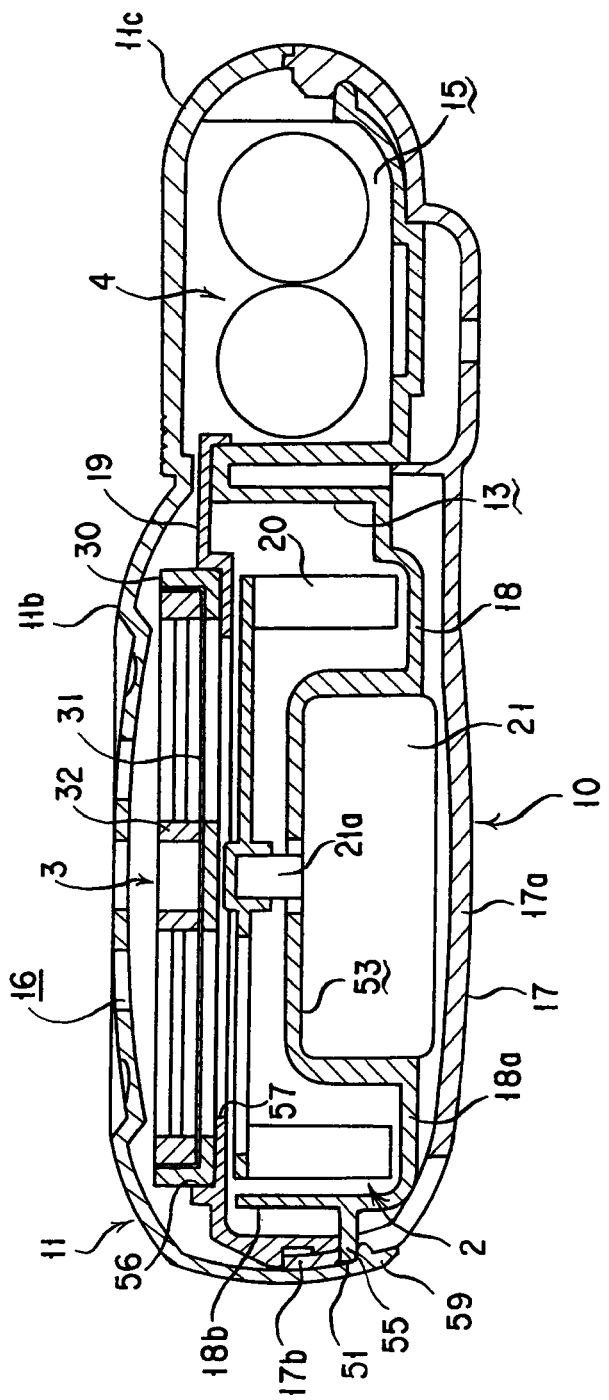
FIG. 2 is a longitudinal cross sectional view of the apparatus shown in FIG. 1.
Figure 3:
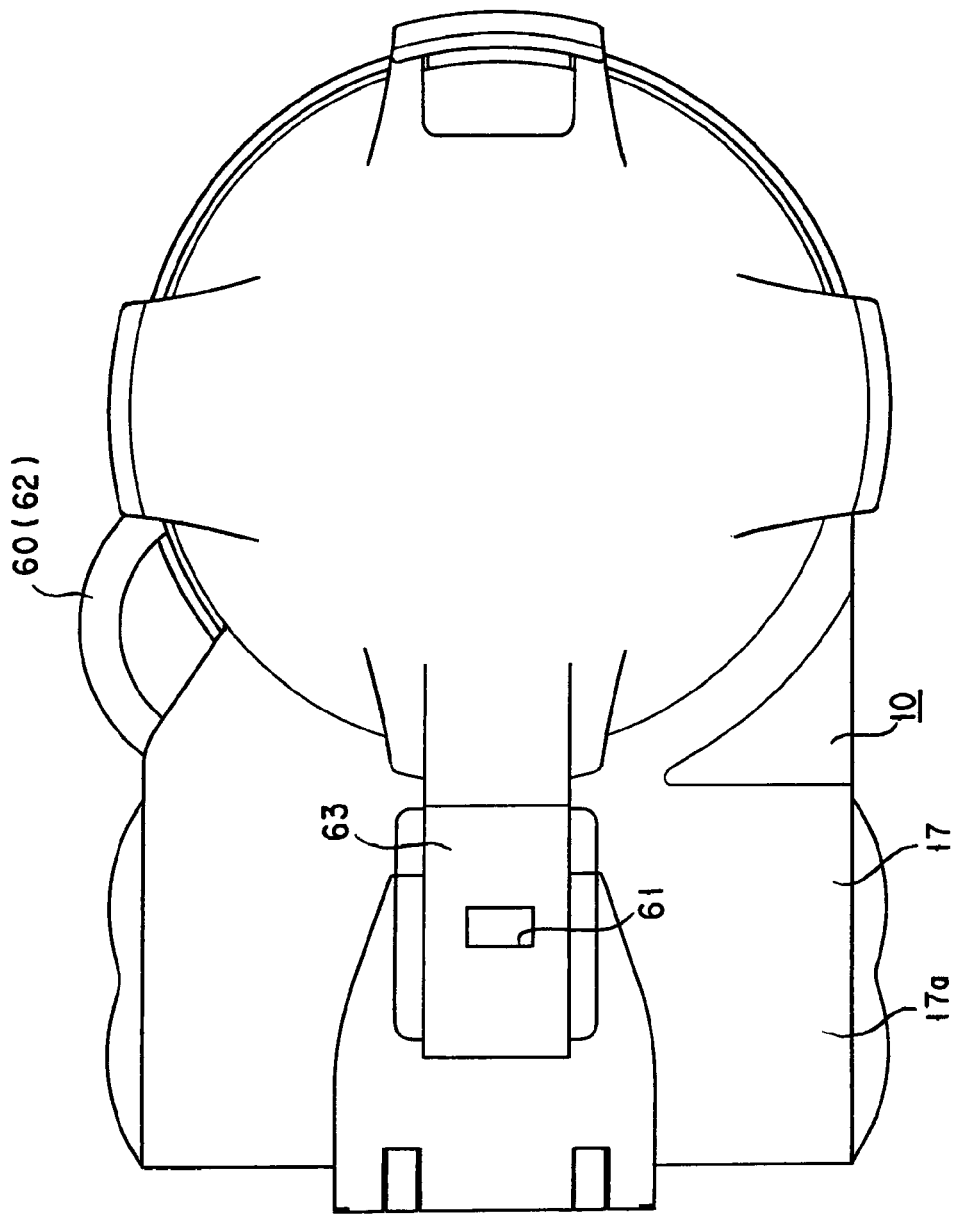
FIG. 3 is a rear view of the apparatus shown in FIG. 1.

At the outset, mention is made of a first form of implementation of the present invention.

Referring to FIGS. 1 to 4, a blower type chemical diffusing apparatus according to the first form of implementation of the invention includes an apparatus or casing main body 1, and an air blower 2, a chemical cartridge 3 and a battery 4 which are contained in the casing main body 1.

The casing main body 1 comprises a first and a second counterpart casing member 10 and 11 openably interconnected by a hinge 12 so they can make the casing main body 1 open and closed.

The first casing member 10 is extremely small in thickness compared with its planar size, namely thin plate-like. It is formed with a blower mounting recess 13, air passages 14 open to the blower mounting recess 13, and a battery accommodating recess 15. The blower mounting recess 13 and the battery accepting recess 15 are each open to an inner side lateral face 10a of the first casing member 10 and are mutually spaced apart in a plane thereof so that they do not lie one above the other in a direction of its thickness. The air passages 14 open the blower mounting recess 13 to an outer surface 10b of the first casing member 10.

The second casing member 11 is extremely small in thickness compared with its planar size, namely thin plate-like. It can take two positions, viz. one in which it covers, and the other in which it uncovers, both the blower mounting recess 13 and the battery accommodating recess 15. The second casing member 11 is formed with air passages 16 in an area thereof that is opposed to the blower mounting recess 13 of the first casing member 10.

The air blower 2 includes a fan 20 and a motor 21 mounted as received within the blower mounting recess 13 and is designed so that the rotation of the fan 20 by the motor 21 when the second casing member 11 is in its closed state causes air to flow over the air passages 14 of the first casing member 10 and the air passages 16 of the second casing member 11.

For example, air may be drawn through the air passages 16 of the second casing member 11 and discharged through the air passages 14 of the first casing member 10 into the atmosphere, or vice versa.

The chemical cartridge 3 includes a chemical impregnated body that is a carrier in the form of a sheet impregnated with a chemical placed on an annular edge in the blower mounting recess 13 and, when the second casing member 11 is brought into its closed position, is held against the annular edge with an inner face 11b thereof.

The battery accommodating recess 15 provides a space in which the battery 3 in the form of dry cells can removably be set.

With the apparatus configured as mentioned above, bringing the second casing member 11 into its open position relative to the first casing member 10 allows removing, setting in place and exchanging the cartridge 3 and the battery 4.

And, bringing the second casing member 11 into its close position relative to the first casing member 10 followed by driving the motor 21 to rotate the fan 20 permits air to pass through the chemical impregnated body in the chemical cartridge and air having chemical entrained therein to be emanated and diffused into an environmental atmosphere.

Further, the apparatus casing body 1 even in its closed position is itself extremely small in thickness compared with its planar size, namely thin and plate-like. Here, its planar size is as large as slightly larger than those of the fan 20 and the battery 4, namely a planar size practically without having any area other than the area in which the fan 20 and the battery 4 can just be accommodated within the apparatus casing body 1 (thus, omitting any useless planar space).

Thus, the apparatus casing body 1 is made thin and compact, permitting the blower type chemical diffusing apparatus to be made thin and compact.

This makes the apparatus easy to handle and renders its required molds smaller in size and stock material less in amount, thus reducing its cost of manufacture as well.

Specifically, as seen in its planar shape the apparatus casing body 1 comprises a first region 1a that is nearly circular, a second region 1b that is nearly rectangular and a third or intermediate region 1c interconnecting the first and second regions 1a and 1b, and as a whole is nearly rectangular except for the first region 1a that is nearly circular.

The first, nearly circular region 1a has a planar size that is slightly larger than the outer diameter of the fan 20, the second, nearly rectangular region 1b has a planar size that is slightly larger than that of the battery 4 and the intermediate region 1c is in the planar form of a pair of deltas simply to make the first and second regions contiguous so that there is no useless space in contour and volume of the apparatus.

As a result, the apparatus casing body 1 has its surface contour appropriately convexed and concaved, giving aesthetic accentuation to its overall shape and making the apparatus visually attractive to the user.

In contrast, the casing body of a conventional apparatus of this type was is monotonous in its surface contour without such an accentuation so that its appearance was not much attractive to the user.

The air passages 14 can be formed not only in the first region 1a but also in both sides of the intermediate region 1c so that chemical can be emanated and diffused towards a greater number of directions.

Mention is next made of further configurations of the apparatus components.

The first casing member 10 includes an outer shell 17, an inner shell 18 and an inner plate 19. The outer shell 17 is dish shaped comprising a surface plate 17a provided with side plates 17b along it and formed with air passage cutouts 50 and also with a first and a second engagement section 51 and 52

The inner shell 18 comprises a base plate 18a provided with a side plate and is fitted into the outer shell 17.

The base plate 18a is formed with a recess 53 open to the surface plate 17a of the outer shell 17. The motor 21 is received and mounted in position in the recess 53 from which its output shaft 21a projects passing through the base plate 18a and has the fan 20 attached thereto. The fan 20 is here a sirocco fan but may be a propeller fan or the like.

The side plate 18b is provided with a plurality of draft guides 54 and also with an engaging section 55 for engagement with the engagement section 51.

The inner plate 19 has an annular reentrant 56 defining a circular opening 57 and is formed with an engaging section 58 for engagement with the engagement section 52 of the outer shell 1 to cover the fan 20.

The makeup described above allows the air blower 2 to be readily set in position in the first casing member 10, namely by accommodating and mounting the motor 21 in position in the recess 53 of the inner shell 18 and fitting the inner shell 18 in this state into the outer shell 17, followed by attaching the fan 20 and then fitting the inner plate 19. Not only is this structure easy to assemble but also it looks agreeable with the motor 21 placed out of view by the outer shell 17.

The outer shell 17 and the inner shell 18 also make the battery accommodating recess 15.

The second casing member 11 is dish shaped comprising a surface plate 11b provided with a side plate 11c, which is formed with engagement section 59 that is designed to engage with the engagement section 55 of the inner shell 18. The surface plate 11b has a round raised area 11d formed with the air passages 16, e.g., in the form of a plurality of slits as shown.

The side plate 17b of the outer shell 17 in the first casing member 10 is formed midway of its length with a cutout 17c while the side plate 11c of the second casing member 11 is likewise formed midway of its length with a cutout 11e, these cutouts being formed as opposed to each other to provide the air passages 14, as shown in FIG. 1.

The chemical cartridge 3 includes a round dish-shaped receptacle 30 with its one side open, a disk-shaped chemical impregnated body 31 loaded in this round receptacle 30 and a round lid 32 fitted into the latter. Here, the round receptacle 30 and round lid 32 are formed with air passages 30a air passages 32a, respectively.

The chemical impregnated body 31 is a chemical carrier in the form of a sheet-like or thin disk impregnated with a chemical.

The round receptacle 30 is placed on the annular reentrant 56 of the inner plate 19 so as to fit with and be carried by it. Then, bringing the second casing member 11 into its closed position places its round raised area 11d in opposition to the round lid 32.

This sets the round receptacle 30 (and the chemical cartridge 3) in position firmly in the apparatus casing body 1.

The air blower 2 and the battery 4 are spaced apart from each other in planar position and do not overlap in the direction of thickness while the chemical cartridge 3 using a chemical impregnated body or carrier in the form of a sheet is thin.

These in combination give rise to a blower type chemical diffusing apparatus which as a whole is thin.

The apparatus casing body 1 so that it can be used in suspension is provided on its side face with a hanger loop 60 and also in its bottom face with a hanger opening 61, which can be alternatively used for hooking.

The hanger loop 60 may be formed, for example, of a U-shaped piece 62 raised from and made integral with one of the side plates 18b of the inner shell 18 in the first casing member 10 of the apparatus casing body 1.

The hanger opening 61 may be formed in a nearly L-shaped attachment piece 63 raised from and made integral with the surface plate 17a of the outer shell 17 in the first casing member 10 of the apparatus casing body 1.

Figure 5:
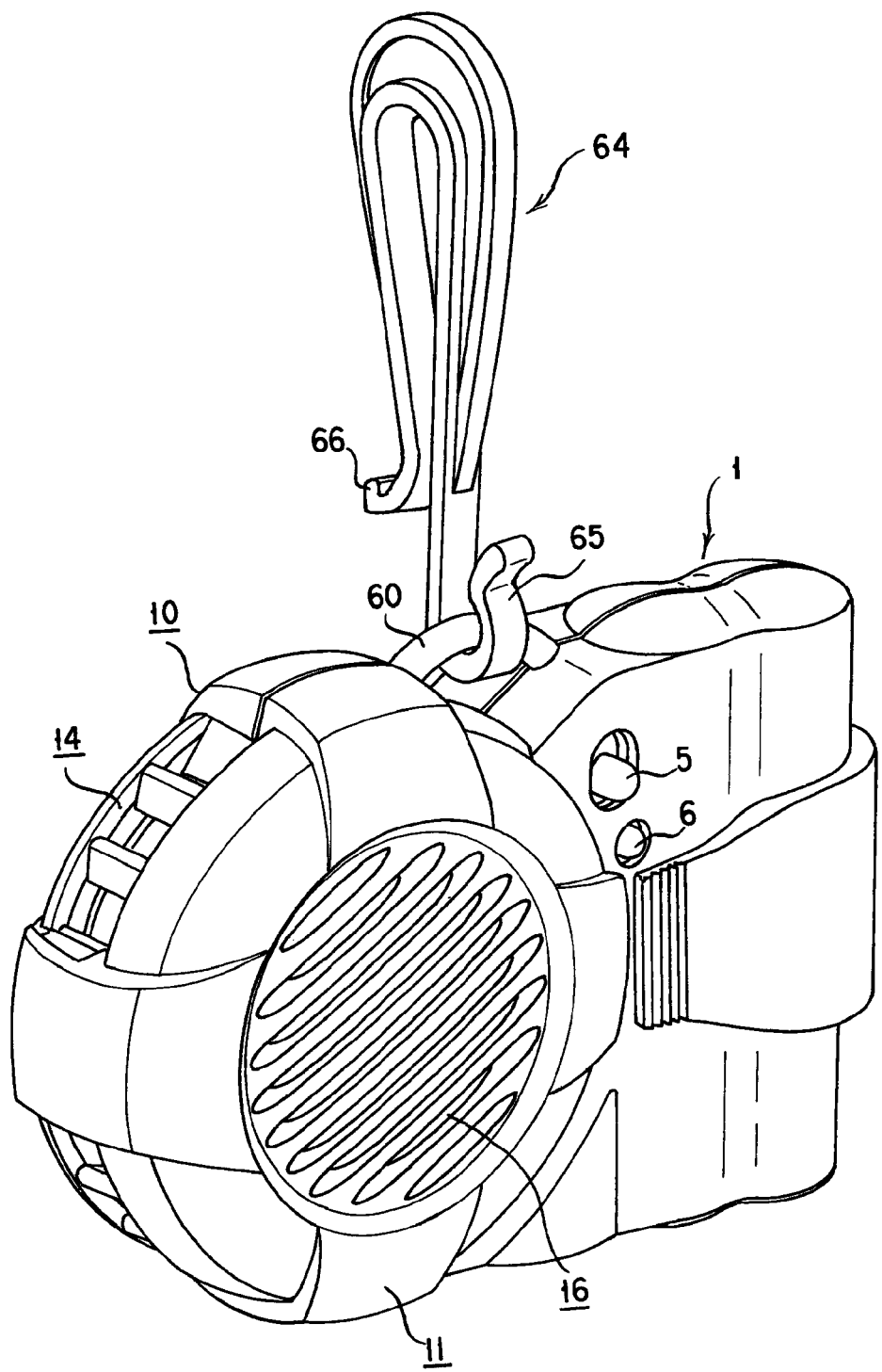
FIG. 5 is a perspective view of the apparatus while it is hung.
Figure 6:
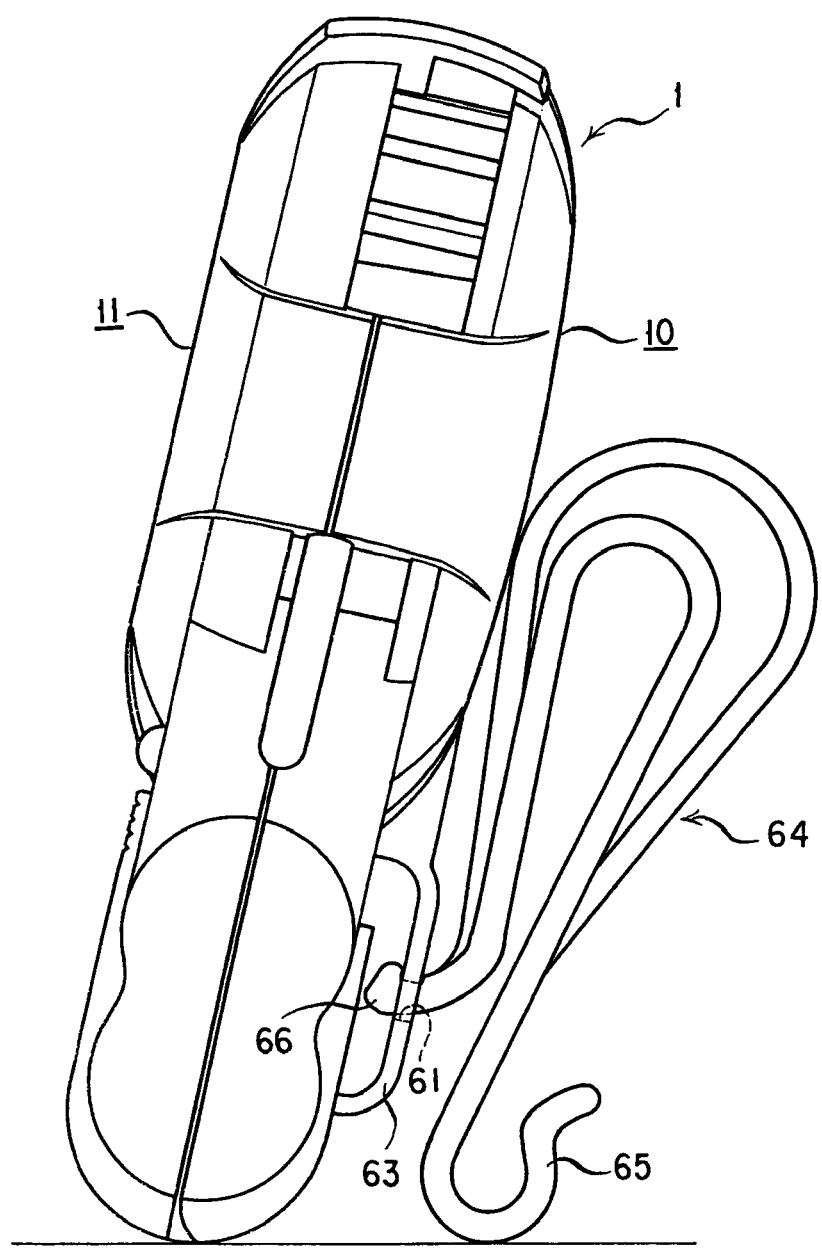
FIG. 6 is an elevational side view of the apparatus in use.

As shown in FIGS. 5 and 6, a hanger (hanging utensil) 64 may be used that has a first hook 60 and a second hook 66 which are to engage the pieces 62 and 63 for the hanger loop 65 and the hanger opening 61, respectively.

So equipped as mentioned above, a blower type chemical diffusing apparatus according to the present invention can be carried by the user by being hung on the hanger 64 which as shown in FIG. 5 can in turn be hung on a belt the user wears.

Also, the use of the hanger 64 as a fall protector for the apparatus casing body 1 upon inserting the hook 66 in the opening 61 and erecting the casing body 1 longitudinally to stand on a supporting plane as shown in FIG. 6 allows a blower type chemical diffusing apparatus according to the present invention to be used as it rests on a floor, table or the like.

Further, a string can be tied to the hanger loop 60 and then be used to hang the apparatus on a wall or the like or on a part of the body or a piece of clothing of the user.

Also, the apparatus that is thus thin and compact can be readily handled by any user from a child to a grownup, with its casing body attached to the waist, neck, arm or leg.

Figure 4:
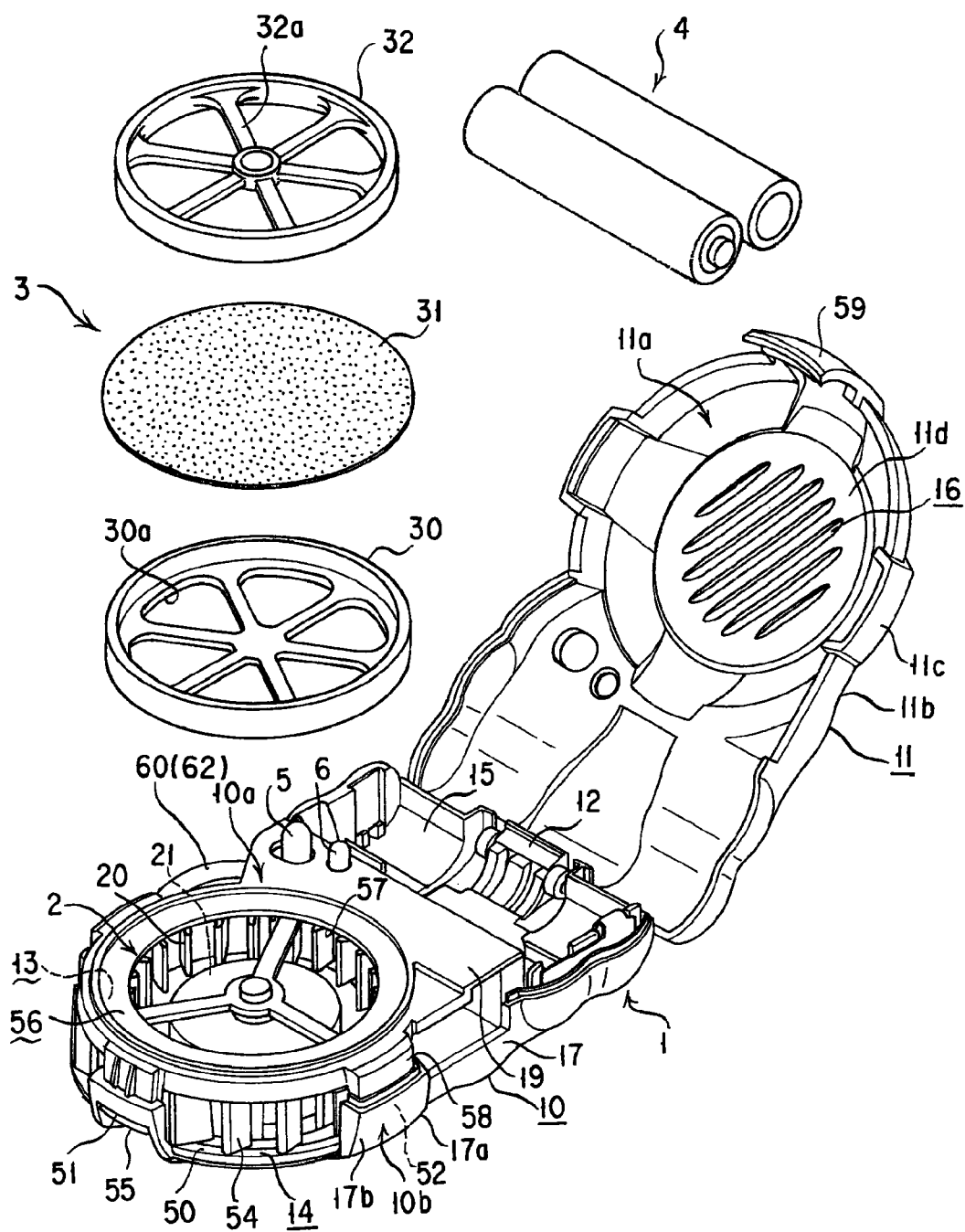
FIG. 4 is a perspective view of the apparatus of FIG. 1 shown in its open state also with a chemical retainer shown as broken.

In FIGS. 1 and 4, a switch 5 and a lamp 6 are also shown. The switch 5 is turned on and off to energize and deenergize the motor 21 while turning the lamp 6 on and off, respectively.

The sheet-like carrier used as impregnated with a chemical in the present invention is illustratively made of a porous paper, cloth, woven or nonwoven fabric or net material. Taking its stability as it is placed into consideration, it is desirable that the chemical impregnated body for use be firmly held by a receptacle and its lid or coating a portion, e.g., an outer peripheral portion, of the sheet-like chemical impregnated body with a resin or the like. Further, considering its portability, it is desirable that the carrier be a thin sheet having a thickness of 2 to 5 mm and an area of 700 to 3,000 mm$^2$.

The chemical for use in the present invention may be an insect pest control agent such as an insecticide, miticide, vermin or pest repellent, vermin growth retardant or sucking inhibitor, aromatic, deodorant or bactericide, and should be volatile.

Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical carrier thin and small.

The power supply for the motor 21 can illustratively be one or more of dry cells such as alkaline dry cells of size AAAA, AAA, AA, C and D, manganese dry cells of size AAAA, AAA, AA, C and D, rectangular-shaped alkaline cell (9 volts), lithium cells and lithium button cells which can be used singly or in combination.

The fan 20 for use in the present invention can be a centrifugal fan which preferably has a size as stated below.

The centrifugal fan preferably has a diameter D of 30 mm to 60 mm. If it is smaller in diameter, then its rotation will not produce a sufficient centrifugal force, which requires larger energy to rotate it more rapidly and deteriorates energy efficiency.

This also reduces the volume of the internal space that it takes, which in turn reduces choices of the motor 21. Conversely, making the fan larger in D than 60 mm will make the apparatus larger in size and its portability poor.

The centrifugal fan preferably has a ratio: D/d of outer diameter D to inner diameter d that is 1.05 to 1.6. If it is smaller than 1.05, then a consequential reduction of a fan blade in width will not produce enough wind. Conversely, if it exceeds 1.6, then the resistance to rotation that the fan blade receives will become excessive, again deteriorating its energy efficiency.

The centrifugal fan preferably has an effective height of blade h ranging between 2 mm to 10 mm. If it is lower than 2 mm in height, the blade will not have enough surface area to produce adequate wind. Conversely, not only will a height more than 10 mm make the fan inadequate to make the apparatus thin but also a resultant increase in resistance to rotation will reduce its energy efficiency.

If the motor is placed anywhere other than in the common internal space in which the centrifugal fan is placed, there will be no bad influence on wind inlet but it is then required that the apparatus have a thickness at the minimum that is the sum of those of the fan and motor. This has been the way adopted by the prior art, however, in failing to make an apparatus of this type so small in both thickness and size as here.

If the motor housing (i.e., the recess 53 in FIG. 2) in which the motor 21 is accepted takes more than 60% of the internal space taken to accept the centrifugal fan, then the balance space will be insufficient for the fan to develop enough air flow and operate efficiently.

Accordingly, the motor housing (i.e., the recess 53 in FIG. 2) stored with the motor 21 should be sized to take a volume within 60% of the internal space for the centrifugal fan to make the apparatus as a whole thin and small in size while operating efficiently to diffuse a chemical.

This proportion, 60%, of space occupancy of the motor housing (i.e., the recess 53 in FIG. 2) should preferably be approached.

An explanation is next given in respect of a second form of implementation of the present invention.

Figure 7:
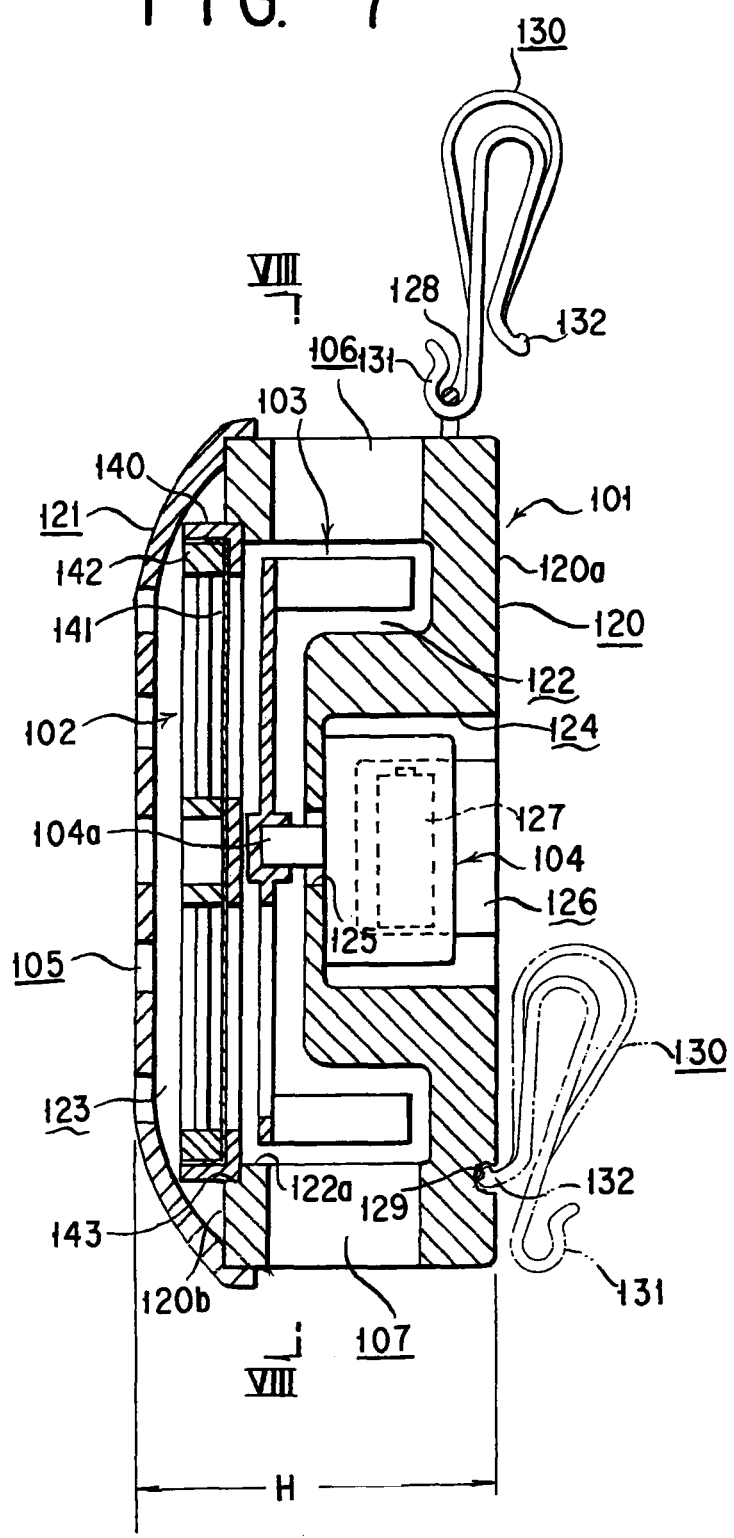
FIG. 7 is a longitudinal cross sectional view illustrating a blower type insect pest control apparatus that represents a second form of implementation of the present invention.
Figure 8:
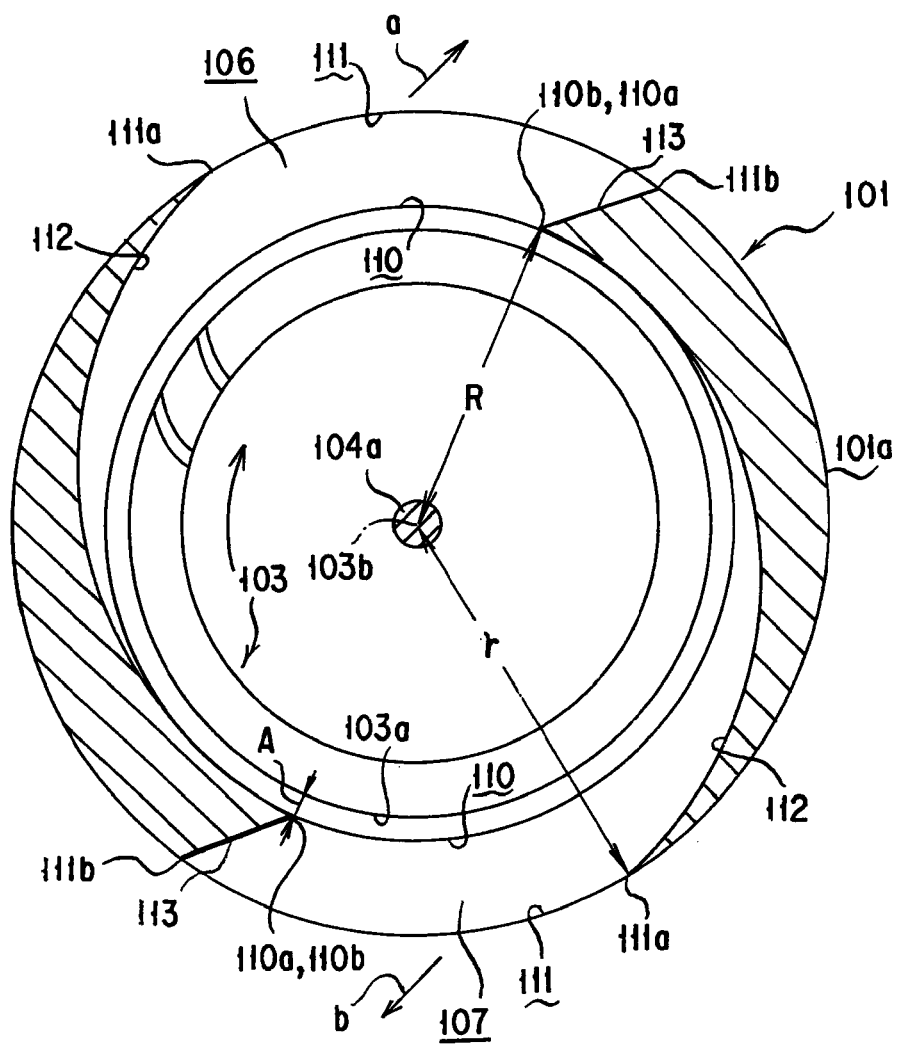
FIG. 8 is a cross sectional view of the apparatus taken alone the line VIII-VIII in FIG. 7.
Figure 9:
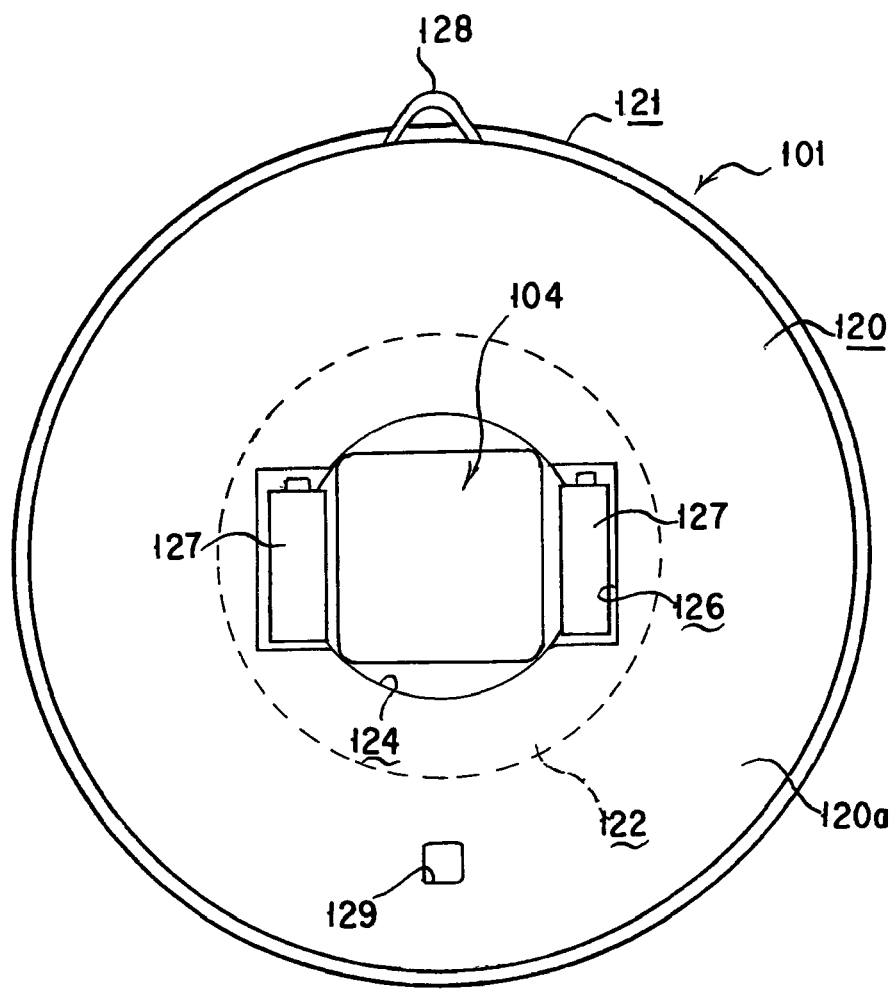
FIG. 9 is a right hand side cross sectional view of the apparatus shown in FIG. 7.

Referring to FIGS. 7, 8 and 9, there is shown an apparatus casing body 101 having a chemical receptacle (chemical cartridge) 102, a fan 103 and a motor 104 stored therein whereby with the fan 103 rotated by the motor 104 air is drawn through air inlet ports 105 into the inside of the chemical receptacle 102 and strikes on the chemical receptacle 102 having a chemical impregnated body impregnated with a chemical that is an insect pest control component). Air then entraining therein such chemical from the chemical impregnated body in the chemical receptacle 102 is discharged through a first and a second air discharge port 106 and 107 into the outside of the casing body 101.

When the apparatus is used with the casing body 101 worn and carried by the user, air containing the insect pest control component or chemical is discharged both through the first air discharge port 106 upwards and through the second air discharge port 107 downwards.

The first and second air discharge ports 106 and 107 are each in the form of an inclined hole having a radial length and with an inlet 110 that lies inner and open to the fan 103 and an outlet 111 that lies outer and open in an outer face 101a of the casing body 101. In each of the first and second air discharge ports 106 and 107, the outer outlet 111 is defined with its upstream and downstream side outlet hole edges 111a and 111b while the inner inlet 110 is defined with its upstream and downstream side inlet hole edges 110a and 110b. In each of the first and second air discharge ports 106 and 107, an upstream side guide face 112 connects the upstream side inlet hole edge 110a in the inner inlet 110 and the upstream side outlet hole edge 111a to each other while a downstream side guide face 113 connects the downstream side inlet hole edge 110b and the downstream side outlet hole edge 111b to each other.

In each of the first and second air discharge ports 106 and 107, the upstream side guide face 112 is inclined so that the upstream side outlet hole edge 111a lies downstream of the upstream side inlet hole edge 110a, the guide face 112 being preferably arcuate.

In each of the first and second air discharge ports 106 and 107, the downstream side guide face 113 is inclined so that the downstream side outlet hole edge 111b lies downstream of the downstream side inlet hole edge 110b, the guide face 113 being preferably arcuate.

The upstream side inner hole edge 110a in the first air discharge port 106 (e.g., the upstream side air discharge port) and the downstream side inner hole edge 110b in the second air discharge port 107 (e.g., the downstream side air discharge port) lie preferably close to, and more preferably also act as, the downstream side inlet hole edge 110b in the second air discharge port 107 and the upstream side inlet hole edge 110a in the first air discharge port 106, respectively.

Here, the terms "upstream" and "downstream" are used in relation to the direction in which the fan 103 is rotated.

Also, the term "inclined" is used to the state of being inclined to a radial direction.

In other words, the first and second air discharge ports 106 and 107 are each in the form of a hole inclined to a direction of rotation of the fan.

With the makeup described above, the rotation of the fan 103 causes air to issue forcibly through the first and second air discharge ports 106 and 107 as indicated by the arrows a and b.

Thus, when the apparatus is used with the casing body 101 attached to the waist of a user, air containing an insect pest control component is allowed to issue forcibly towards his/ her head and feet. Since the insect pest control component is therefore allowed to reach the head and feet quickly, it is possible to protect the user from harmful insects immediately after the apparatus begins to be used.

Mention is next made of specific configurations of apparatus components.

The apparatus casing body 101 comprises a base member 120 and a cover member 121 removably attached thereto and is provided with a fan, a chemical and a motor accommodating chamber 122, 123 and 124.

The fan accommodating chamber 122 is round in which a fan 103 is rotatably mounted. The fan accommodating chamber 122 has a round peripheral face 122a in which are open the first and second air discharge ports 106 and 107, or their respective inner inlets 110.

Communicating with the fan accommodating chamber 122, the chemical accommodating chamber 123 is opposed and defined with the cover member 121, the cover member 121 being formed with the air inlet ports 105.

The motor accommodating chamber 124 is formed in the base member 120 by opening in its rear face 120a and is partitioned from the fan accommodating chamber 122 by a wall of the base member 120, through which the output shaft 104a of a motor 104 is passed projecting into the fan accommodating chamber 122 wherein it is coupled to the fan 103.

Also lying in the base member 120 is a battery accommodating section 126 that is formed so as not to open the fan accommodating chamber 122 and further not to overlap the motor accommodating chamber 124 in the direction of their thicknesses. The battery accommodating section 126 is formed in the base member 120 as a recess open to its rear face 120a and spatially continuous with the motor accommodating chamber 124.

In this battery accommodating section 126, typically in two compartments thereof disposed as shown across the motor accommodating chamber 124 are accepted two battery cells 127, respectively.

With this battery or these battery cells 127, the motor 104 is energized and driven.

With the casing body 101 constructed as mentioned above, its thickness H can be minimized since the battery 127 and the motor 104 can no longer overlap in its thickness direction.

Further, the motor accommodating chamber 124 and the battery accommodating section (recesses or compartments) which are open in the rear face 120a of the base member 120 can be with their cap or caps for closure.

The casing body 101 is also provided in its base member 120 with a hanger loop 128 and a hanger hole 129.

The hanger loop 128 as shown in FIG. 7 enables the casing body 101 to be hung on a hanging utensil 130 which can in turn be attached to or clipped on a user's belt or the like in use of the apparatus.

Figure 10:
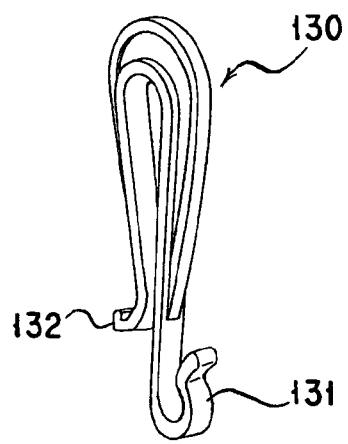
FIG. 10 is a perspective view illustrating a hanging gadget used in the apparatus of FIG. 7.

The hanging utensil 130 as shown in FIG. 10 has at its one end a hook 131 that can engage the hanger loop 128 to hook the casing body 101 on the hanging utensil 130, which has at its other end another hook 132 that can be fitted into the hole 129.

With the hook 132 fitted in the hole 129 as shown in FIG. 7, therefore, the utensil 130 when oriented to stand as indicated by the imaginary line with the hook 131 placed in contact with a supporting plane such as a table can also be used to support the casing body 101, namely the apparatus placed on thereon.

Of course, the apparatus can also be used with the rear face 120a of the base member 120 placed on such a supporting surface.

Figure 11:
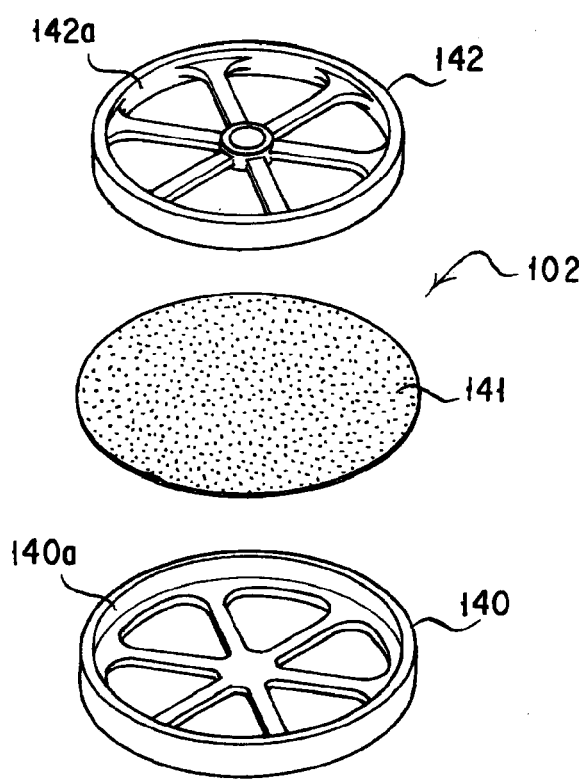
FIG. 11 is a exploded perspective view of a chemical receptacle.

The chemical receptacle 102 as shown in FIG. 11 comprises a round dish-shaped receptacle 140 with its one side open and has a disk-shaped chemical impregnated body 141 loaded in this round receptacle 140 and a round lid 142 fitted into the latter. Here, the round receptacle 140 and round lid 142 are formed with air passages 140a air passages 142a, respectively.

The chemical impregnated body 141 is a chemical carrier in the form of a sheet-like or thin disk impregnated with a chemical.

The round receptacle 140 is placed on the annular reentrant 143 formed in a front face 120b of the base member 120 so as to fit with and be carried by it.

As mentioned above, the chemical receptacle 102 using a chemical integrate body 141 in the form of a sheet-like carrier impregnated with an insect pest control component is thin and can make the apparatus casing body 101 small in thickness H.

Mention is next made of further details of the first and second air discharge ports 106 and 107.

Referring to FIG. 8, the fan 103 has its outer peripheral face 103a which is preferably spaced from the upstream side inlet hole edge 110a by a distance A ranging from 0.1 mm to 5 mm.

The fan 103 has its center 103b which is preferably spaced from the upstream side inlet hole edge 110a by a distance R having relationship: r=1.05×R~2.5×R where r is distance between the center 103b of the fan 103 and the upstream side outlet hole edge 111a.

This converges wind flows produced by rotation of the fan 103 to converge efficiently in the first and second air discharge ports 106 (through these flow paths) and 107, thereby causing air containing the insect pest control component to be forcibly discharged therethrough.

To with, although it is desirable on the one hand that distance A approach A=0 infinitely, on the other hand if A<0.1 mm it then becomes difficult to control accuracy of the members of which the apparatus is made. Then, an inaccuracy will produce an interference between the fan 103 and the upstream side inlet hole edge, which can be avoided only at a significant additional cost then required to achieve due precision.

Conversely, if A>5 mm, the wind by the fan 103 will then tend to be led less into the first and second air discharge ports 106 and 107 and rather pass round the regions of distance A and circulate almost within the fan accommodating chamber 122. Then, the wind will be lost of its force there with a consequent loss of diffusion efficiency.

Also, if r<1.05×R, then the width of the first and second air discharge ports 106 and 107 will become so small that the wind by the fan 103 while passing through them suffers a pressure loss.

Conversely, if r>2.5×R, then the width of the first and second air discharge ports 106 and 107 will become so large in that the wind by the fan 103 spreads out suddenly there, losing its pressure again with a consequent loss of diffusion efficiency.

Here, the term "width of the first and second air discharge ports 106 and 107" is used to mean the radial distance between the inner inlet 110 and the outer outlet 111.

While the first and second air discharge ports 106 and 107 are typically constructed as mentioned above to have an identical air resistance to discharge an identical air flow therethrough so that an identical amount of the insect pest control component may be emitted towards both the user's head and foot regions, it may be desirable depending on a place of use to emit more of it towards one of these regions than towards the other.

Then, the air resistance of a selected one of the first and second air discharge ports 106 and 107 can be made smaller than that of the other to cause air entraining more in amount of the insect pest control component to be emitted through the selected air discharge port into the outside air. Alternatively, a third air discharge port may additionally be formed in the base member 120 through which to cause air containing the insect pest control component to be emitted towards upwards or downwards.

Figure 12:
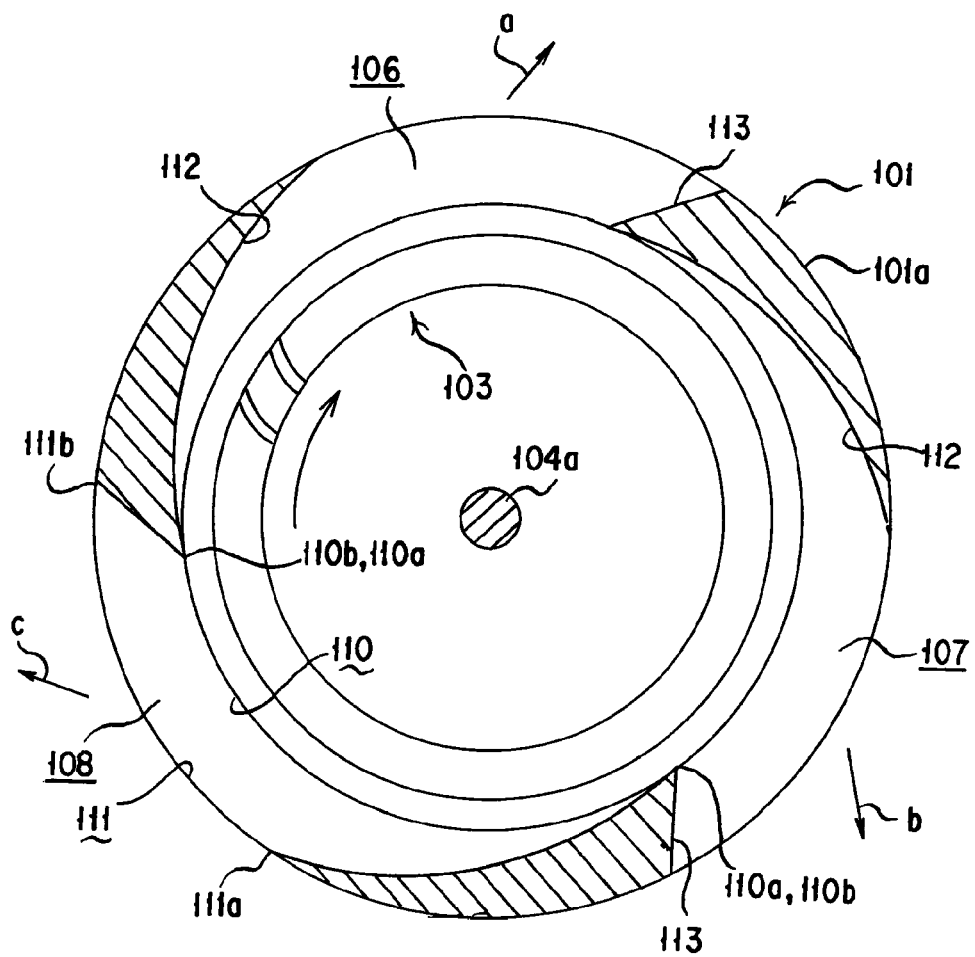
FIG. 12 is a cross sectional view of a region of an air discharge port illustrating a first modification of the blower type insect pest control apparatus.

For example, in a modification here as shown in FIG. 12 a first, a second and a third air discharge port 106, 107 and 108 may be formed as angularly spaced apart by an angle of 120° in a vertical plane such that air is emitted through the first, second and third air discharge ports 106, 107 and 108 upwards, downwards and obliquely upwards as indicated by the arrows a, b and c, respectively.

This modification therefore permits the insect pest component to be emitted more upwards.

Should the apparatus be designed to cause the insect pest control component to be emitted more downwards, the third exhaust port 108 can be so arranged and configured as to discharge air obliquely downwards. For example, the apparatus can take a position vertically opposite to that shown in FIG. 12.

While only the first and second air discharge ports 106 and 107 or the first, second and third air discharge ports 106, 107 and 108 are shown above to be provided, the apparatus especially when designed for use as worn on the waist may be formed with a subsidiary air discharge port or ports to direct air laterally thereof where the insect pest control component may become deficient so that air is emitted in all directions with upwards and downwards inclusive.

Figure 13:
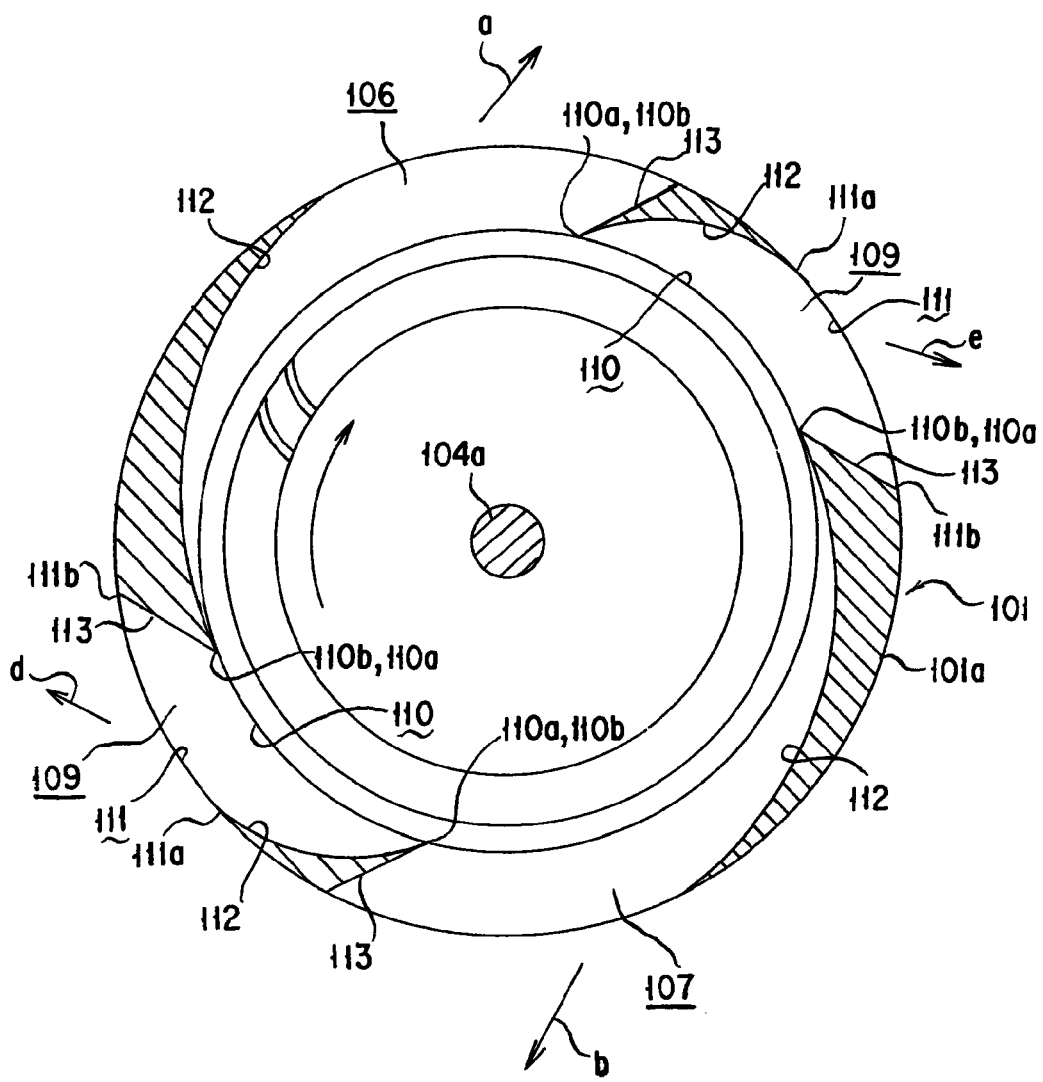
FIG. 13 is a cross sectional view of a region of an air discharge port illustrating a second modification of the blower type insect pest control apparatus.

For example, subsidiary air discharge ports 109 facing laterally right and left sides may be formed in a second modification here as shown in FIG. 13.

Such a subsidiary air discharge port 109 is substantially identical in shape to but larger in air resistance than the first and second air discharge ports 106 and 107 mentioned above. For example, it is less open in the direction of rotation of the fan and less in the amount of air discharged and less energetic than the first and second air discharge ports 106 and 107.

Thus, the sizes in the rotation of the fan between the upstream side inlet hole edge 110a and the downstream side inlet hole edge 110b and between the upstream side outlet hole edge 111a and the downstream side outlet hole edge 111b in the subsidiary air discharge port 109 are smaller in than those in the first ands second air discharge ports 106 band 107.

Since this allows air containing the insect pest control component to be discharged laterally towards the right and left sides as indicated by the arrows d and e, the insect pest control component can be emitted laterally of the user's waist, as well as towards the user's head and feet.

One or two such subsidiary air discharge ports 109 may be provided on only one or both of the right and left hand sides of the user's waist.

In effect, there need be no limitation imposed on the number of subsidiary air discharge ports as mentioned above.

The total number of air discharge ports is preferably at most six, including two main air discharge ports in the up and down sides (first and air discharge ports 106 and 107) or three main air discharge ports in three sides (first, second and third air discharge ports 106, 107 and 108) and one or more subsidiary air discharge ports 109. That will be sufficient to cover insect pest control effects in lateral directions and more than that will merely weaken the power of air upwards and downwards.

To prevent entry of contaminants through the first, second and third air discharge ports 106, 107, 108 and subsidiary air discharge ports 109, a plurality of current plates may be provided for these air discharge ports, which are preferably oriented horizontally parallel to wind flows and mutually spaced apart by a distance of 1 to mm.

Each such current plate is preferably shaped rectangular, elliptical or in the form of a water drop or any other that does not impede wind flows.

The chemical for use in the present invention may be a miticide, vermin or pest repellent, insecticide, or vermin growth retardant or sucking inhibitor, and should be volatile.

Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical carrier thin and small.

The sheet-like carrier used as impregnated with a chemical in the present invention is illustratively made of a porous paper, cloth, woven or nonwoven fabric or net material. Taking its stability as it is placed into consideration, it is desirable that the chemical impregnated body for use be firmly held by a receptacle and its lid or coating a portion, e.g., an outer peripheral portion, of the sheet-like chemical impregnated body with a resin or the like. The receptacle and lid may be composed of a material such as polyethylene terephthalate, polypropylene, polyethylene, polyacetal, nylon, acrylic, ABS, paper, AS or metal. Further, considering its portability, it is desirable that the carrier be a thin sheet having a thickness of 2 to 5 mm and an area of 700 to 3,000 $mm^2$.

Especially, nonwoven fabric is suitable, preferably a "metsuke" (mass per unit area) of 10 $g/m^2$ and more preferably 20 to 50 $g/m^2$. If it exceeds 100 $g/m^2$, then the chemical impregnated body will become too large in air resistance to pass the wind by the fan and to diffuse the chemical smoothly. Conversely, it is smaller than 10 $g/m^2$, the chemical in amount that can be retained in the chemical carrier will be too little and soon become short of supply to justify its manufacture.

The fan may be a centrifugal fan such as a sirocco fan, radial fan or turbo fan.

The fan should be rotated at a rate of rotation of preferably 500 to 4,000 rpm and more preferably 700 to 3,000 rpm.

The centrifugal fan should have a diameter preferably of 20 to 100 mm and preferably 30 to 60 mm. It should have a height preferably of 2 to 50 mm and more preferably 5 to 20 mm.

The fan, especially sirocco fan or radial fan, should preferably have a number of blades of 10 to 50.

The power supply for driving the fan can illustratively be one or more of dry cells such as alkaline dry cells of size AAAA, AAA, AA, C and D, manganese dry cells of size AAAA, AAA, AA, C and D, rectangular-shaped alkaline cell (9 volts), lithium cells and lithium button cells which can be used single or in combination. A plurality such dry cells can be used connected in series or parallel. A secondary battery can also be used preferably equipped with an AC adapter for recharging by a domestic power supply (at AC 100 volts).

The casing body 101 can be attached to the user not only by the hanger as shown but also in any way such as by means of a clip or with which to hang the apparatus on or a hole formed through which a belt or strap can be passed to attach the apparatus on a region of the user's feet, waist or the arms.

The casing body 101 can be equipped with a switch to turn on off energizing the apparatus and also with an indicator of LED, neon lamp or liquid crystal type for displaying the apparatus being energized. Further, the fan itself can be made visible from the outside so that the state of the apparatus being energized can be seen from the fan rotating.

It should also be advantageous to set both the battery and chemical impregnated body in the chemical receptacle to end their supplies simultaneously. Then, the battery and the chemical receptacle can be mounted in a cartridge so that they can be replaced as a body, thereby improving the expediency of the apparatus in maintenance.

Conversely, if the battery and the chemical impregnated body are not made ending simultaneously, then it should be desirable to make the respective endpoints of the battery and the chemical impregnated body in the chemical receptacle indicated by being displayed individually.

While the casing body 101 (base member 120) is shown above as its peripheral region forming the fan accommodating chamber 122 is larger in thickness to form the air discharge ports, this is not a limitation.

For example, a region of the casing body 101 that is outer to the fan accommodating chamber 122 is formed with a plurality of guide blades circumferentially spaced apart such that interstices between these guide blades form air discharge ports.

A substitute battery accommodating chamber or chambers may be provided in a region or regions lateral of the casing body 101 and to the base member 120.

Although the foregoing description implies the user primarily as a human being, the term is here applicable to a pet such as a dog or livestock such as a cow. In this case, a front to back region of it from its head to tail or from its face to belly and rear feet is an area of interest to which the insect pest control component is to be directed.

An explanation is next given in respect of a third form of implementation of the present invention.

Figure 14:
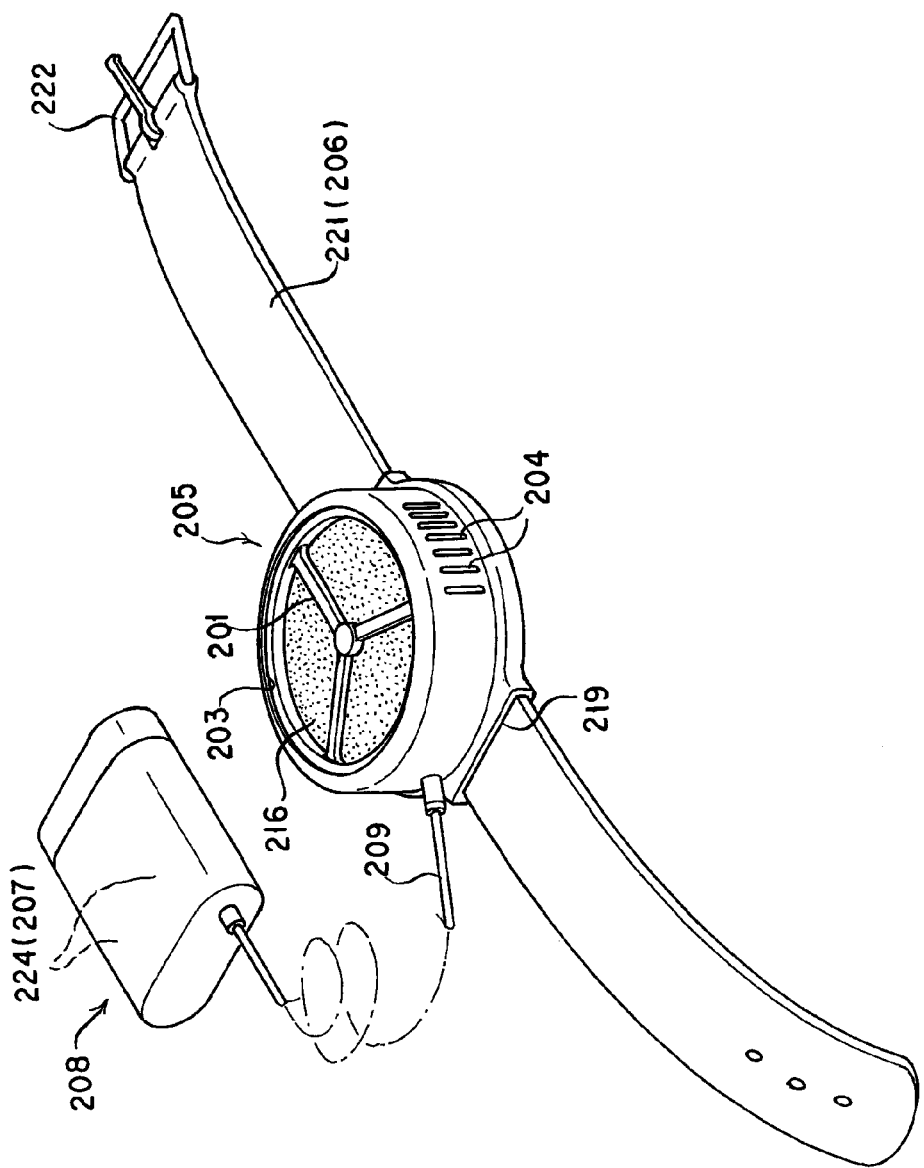
FIG. 14 is a perspective view illustrating a blower type chemical diffusing apparatus that represents a third form of implementation of the present invention.
Figure 15:
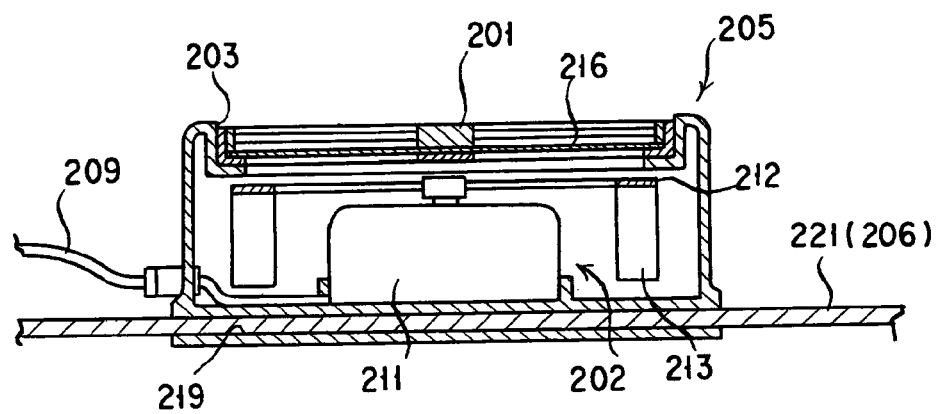
FIG. 15 is a side cross sectional view of the blower type chemical diffusing apparatus shown in FIG. 14.
Figure 16:
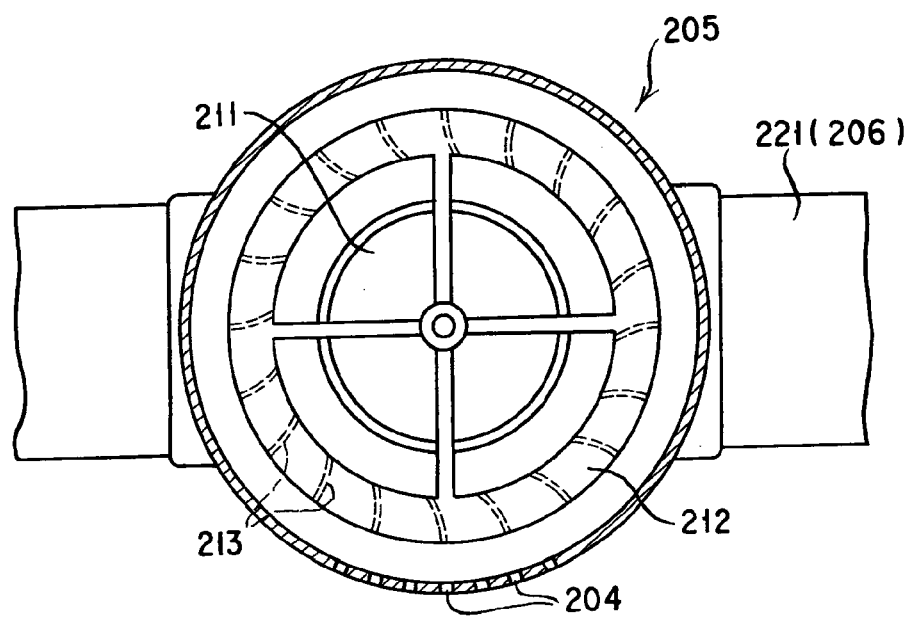
FIG. 16 is a plan view, in part shown in cross section, of the blower type chemical diffusing apparatus shown in FIG. 14.

As shown in FIGS. 14, 15 and 16 a blower type chemical diffusing apparatus according to this form of implementation of the invention includes a chemical receptacle (chemical cartridge) 201 and an air blower 202. It further comprises a main casing body 205 having an air intake port 203 through which air is drawn by the air blower 202 and an air discharge port 204 through which air entraining therein a the chemical volatilizing from the chemical receptacle 201 is emitted; a power casing body 208 separated from the main casing body 205 and containing a power source 207 for the air blower 202 in the main casing body 205; and an electrical cord 209 connecting between the main casing body 205 and the power casing body 208 for energizing the air blower 202 in the main casing body 205 from the power source 207 in the power casing body 208.

More specifically, the main casing body 205 is in the form generally of a circular cylinder that is axially short. And, it forms the air inlet port that is largely open upwards while forming the air discharge port 204 which is open in the form of a plurality of slits in one of its side faces. It should be noted here that the number of such air discharge ports and the size and shape of each of such air inlet and outlet ports are not limited to those shown and described.

And, the main casing body 205 has in its inside and beneath it the air blower 202 positioned. The air blower 202 comprises a motor 211 and a sirocco fan 212 as a sort of the centrifugal fan wherein the motor 211 having its output shaft connected to the fan 212. The sirocco fan 212 has a number of slanting blades 213 circumferentially equidistantly spaced apart, which are rotated by the motor 211 to draw air through the air inlet port 203 at the top of the sirocco fan 212 to cause air drawn to flow centrifugally within the main casing body 205 and to emanate through the air discharge port 204 from the side face of the main casing body 205. However, the use here of the sirocco fan 212 being a sort of the centrifugal fan as the air blower 202 is not a limitation but any other suitable fan such as, for example, a propeller fan having an impeller in the form of a propeller about its axis may be used. When such a propeller fan is used as the blower fan, the main casing body 205 may be formed at its bottom with an air passage hole serving as an air inlet port and may use the abovementioned port 203 as an air discharge port. And, adjacent to the latter there may, as mentioned below, be disposed the chemical receptacle 201 charged with a volatile chemical so that air drawn by the blower fan through the air inlet port at the bottom passes through the chemical receptacle 201 at the air discharge port across the blower fan and upon entraining therein the volatilizing chemical to issue into the outside.

Figure 17:
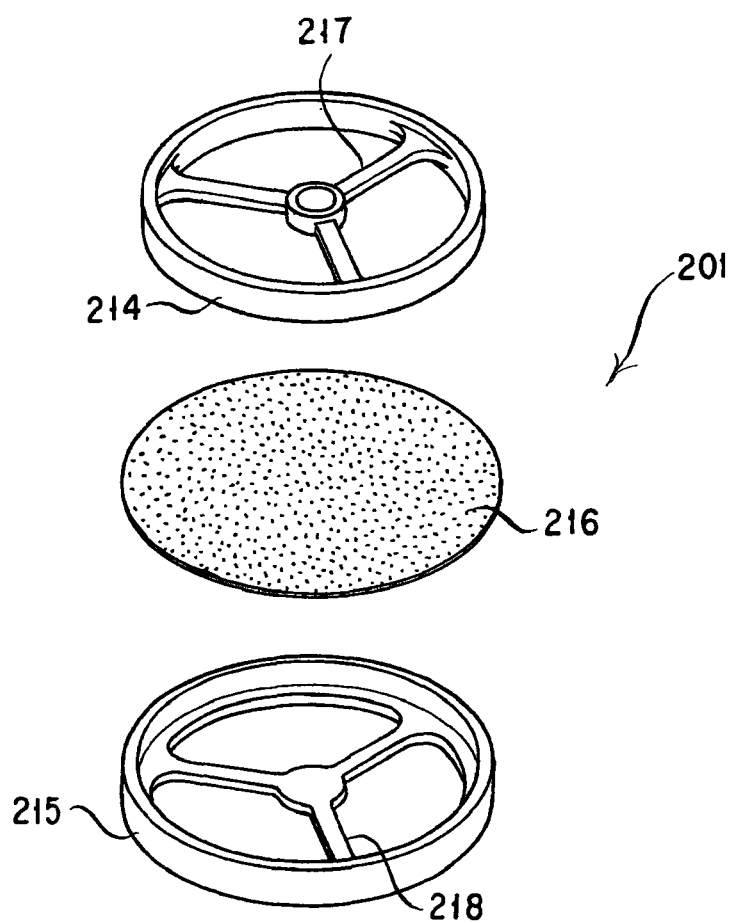
FIG. 17 is a decomposed perspective view illustrating a chemical receptacle.

The chemical receptacle 201 charged with the chemical and disposed as shown within the main casing body 205 is fitted with a region of the main casing body 205 defining the air inlet port 203 at its top so that it lies above the air blower 202. As shown in FIG. 17, the chemical receptacle 201 is round and small in thickness and comprises an upper and a lower member 214 and 215 which to accept a chemical carrier (chemical impregnated body) between them and are fitted together. The upper and lower members 214 and 215 are formed with large apertures 217 and large apertures 218, respectively, through which air passes to cause chemical contained in the chemical carrier 216 to volatilize.

The volatile chemical with which the chemical carrier is to be impregnated in the chemical receptacle 201 is a chemical that serves as an insecticide, repellent, aromatic, deodorant, germicide or fungicide. Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety. Further, such specific chemicals as methofluthrin, transfluthrin, empenthrin, terallethrin and profluthrin which are highly active and which in a small amount exhibit efficaciousness can desirably be used as they can make the chemical carrier thin and small.

Also, the chemical receptacle 201 and the chemical carrier 216 are not limited to types as described but may be any ones suitable to retain a volatile chemical. For example, the chemical carrier 216 may not only be in the form of a sheet but also may be in the form of a net, lattices, a honeycomb, a flocculate, a sponge and may be large number of particles which are impregnated with a chemical. Further, the chemical receptacle 201 need not be one in which a chemical carrier 216 impregnated with a chemical is retained but may be one which itself is made of a hard sponge or foamed body and impregnated with a chemical, namely which itself retains the chemical therein. Such a chemical receptacle 201 may be of any suitable shape and of any suitable material as desired.

The main casing body 205 is formed at its lower face with a fitting 219 for attaching thereto a fitting means 206 that enables the main casing body 205 to be fitted onto an object wherein the fitting 219 is here in the form of a thin and elongate hole extending in its depth across a full length of the casing main body 205.

Then, the fitting means 206 that enables attaching the main casing body 205 to an object is attached to the fitting 219 which has a thin hole passing through the main casing body 205. The fitting means 206 is here in the form of a flexible and elongate belt 221 which with a buckle had at its one end can be worn on a user's wrist. This wearing belt enables the main casing body 205 for the subject blower type chemical diffusing apparatus to be fitted to a user's wrist or the like for its use.

The fitting means 206 shown by the wearing belt 221 is not limited to that described but may have a length ranging from several centimeters that enables its fitting around a user's wrist or the like to 1 or 2 meters suitable for fitting around a user's waist or any suitable supporting object and thus may be of a length as desired. It may also take any of a variety of forms including a belt, band and string. Its material is not limited but may be any known suitable material such as synthetic resin, leather, cloth, textile and rubber. The attachment means used for the wearing belt 221 need not be a buckle 222 as shown but may take a button form, hook form, a plug-in belt form, a Hook-and-Loop fastener (e.g., "magic tape" [registered trade mark]) form or the like.

Figure 18:
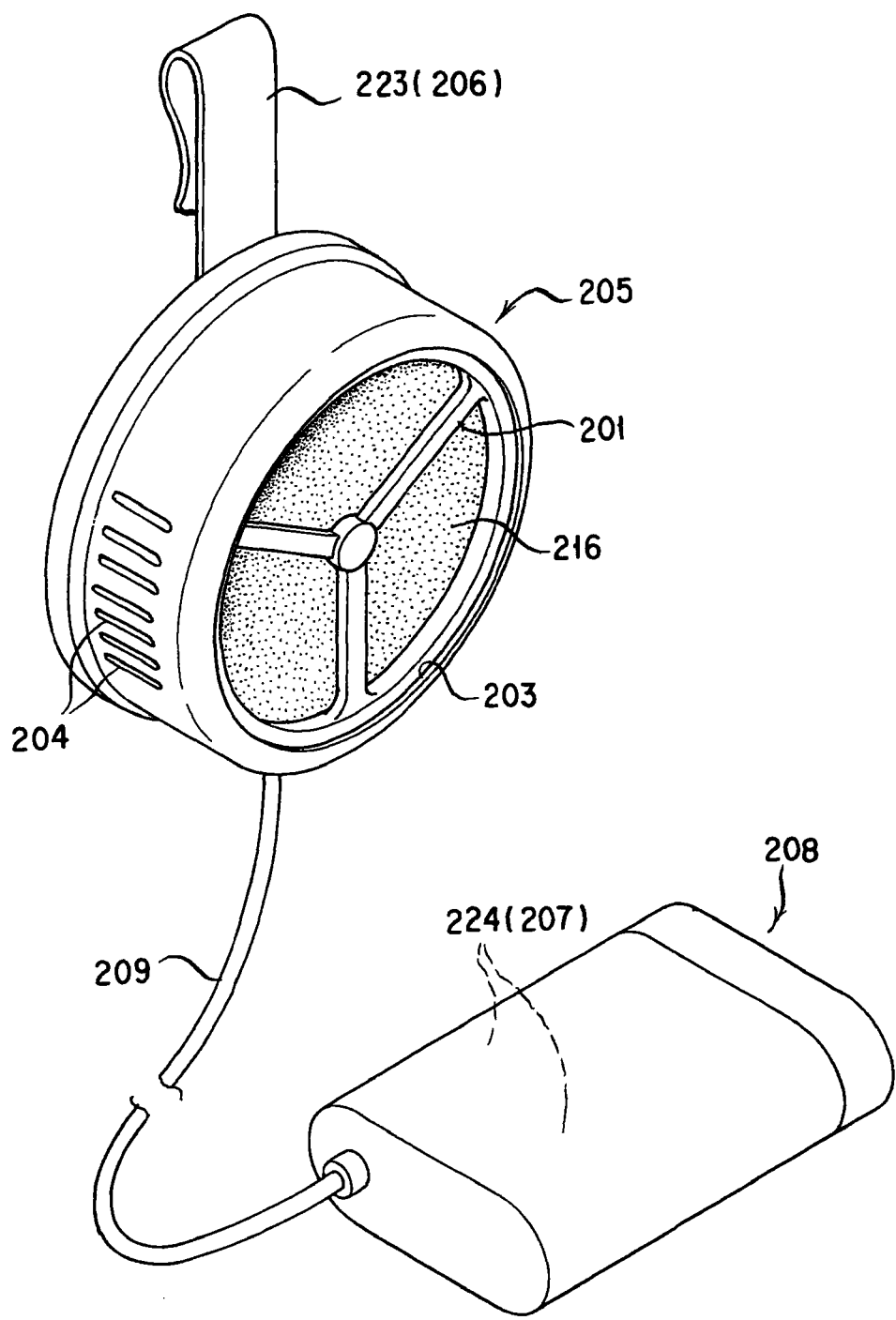
FIG. 18 is a perspective view illustrating another fitting means that can be used with a blower type chemical diffusing apparatus according to the present invention.

Further, the fitting means 206 need not be limited to a wearing belt 221 as shown but may take a form of a belt to be worn around a leg, a hook 223 for hooking at a belt worn on a pant or at a pocket as shown in FIG. 18, or a form of pin or clip to be attached directly to clothing.

The power casing body 208 includes the power source 207 for the air blower 202 in the main casing body 205 and is separate from the main casing body 205. The power source 207 included in the power casing body 208 is a battery 224. The power casing body 208 is a box of a size that is the minimum for accepting the battery 224 required, for example, comprising two dry cells. The battery 224 other than a dry cell or cells may be a rechargeable battery. Separating the power casing body 208 from the main casing body 205 allows making the power casing body 208 larger in size so that the battery 224 larger in size and dry cells 224 larger in number can be used accepted therein. This in turn permits increasing the voltage that can be applied to the main casing body 205 so as to make the output power of the air blower 202, e.g., the strength of the driven fan, finely adjustable while making the subject blower type chemical diffusing apparatus usable over a prolonged time span.

The power casing body 208 may also be adapted so it can have a fitting means 206 attached thereto that enables it to be an object. The fitting means 206 may, here too, be a wearing belt 221, a hook 223, or a pin or clip as mentioned above.

The coupling cord 209 extending between the main casing body 205 and the power casing body 208 to connect them together is an electrical cord for electrically energizing the air blower 202 in the casing main body 205 from the battery 224 as the power source 207 in the power casing body 208. The connection cord 209 should preferably be made as small in diameter as possible. The connection cord 209 may optionally be provided midway or at its one end with a take-up mechanism to make its length adjustable.

Figure 19:
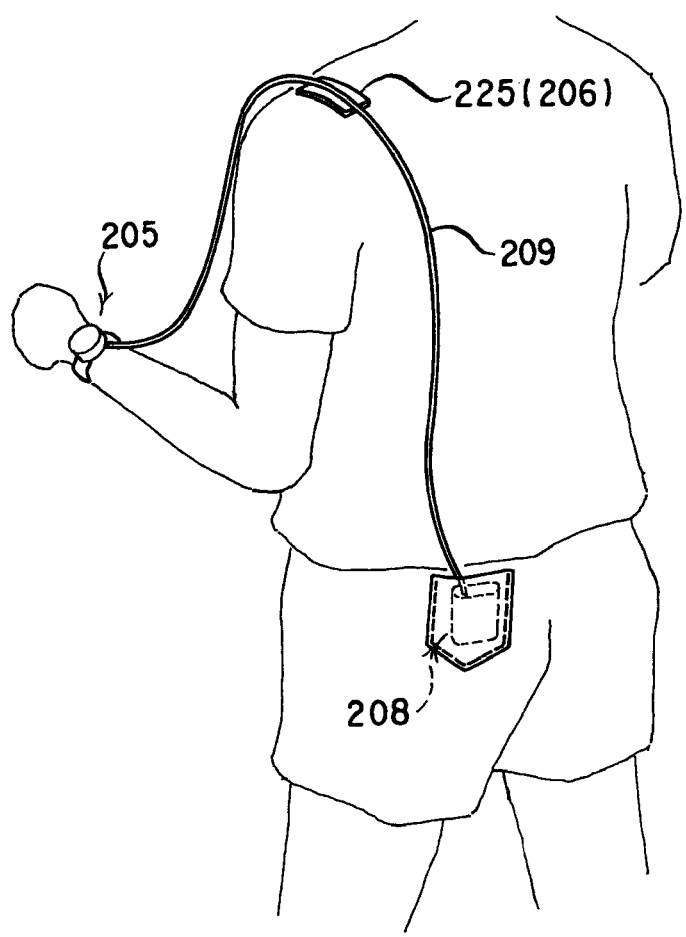
FIG. 19 is an explanatory view illustrating an example of use of a blower type chemical diffusing apparatus according to the present invention.

In FIG. 19, the connection cord 209 is shown also provided with a fitting means 206 that enables itself to be attached to an object. The fitting means 206 here is an attaching member 225 that may be a Hook-and-Loop fastener tape (e.g., a "magic tape"—registered trademark) attached to the connection cord 209 at its midway and having surface irregularities to enable the member to stick to clothing or the like. The attaching member 225 is, of course, not limited to this particular example but may be a safety pin or a clothespin or any other suitable means that can make the connection cord 209 clinging to clothing or the like.

The connection cord 209 may be adapted to make itself detachable from the main casing body 205 or the power casing body 208 or both.

Figure 20:
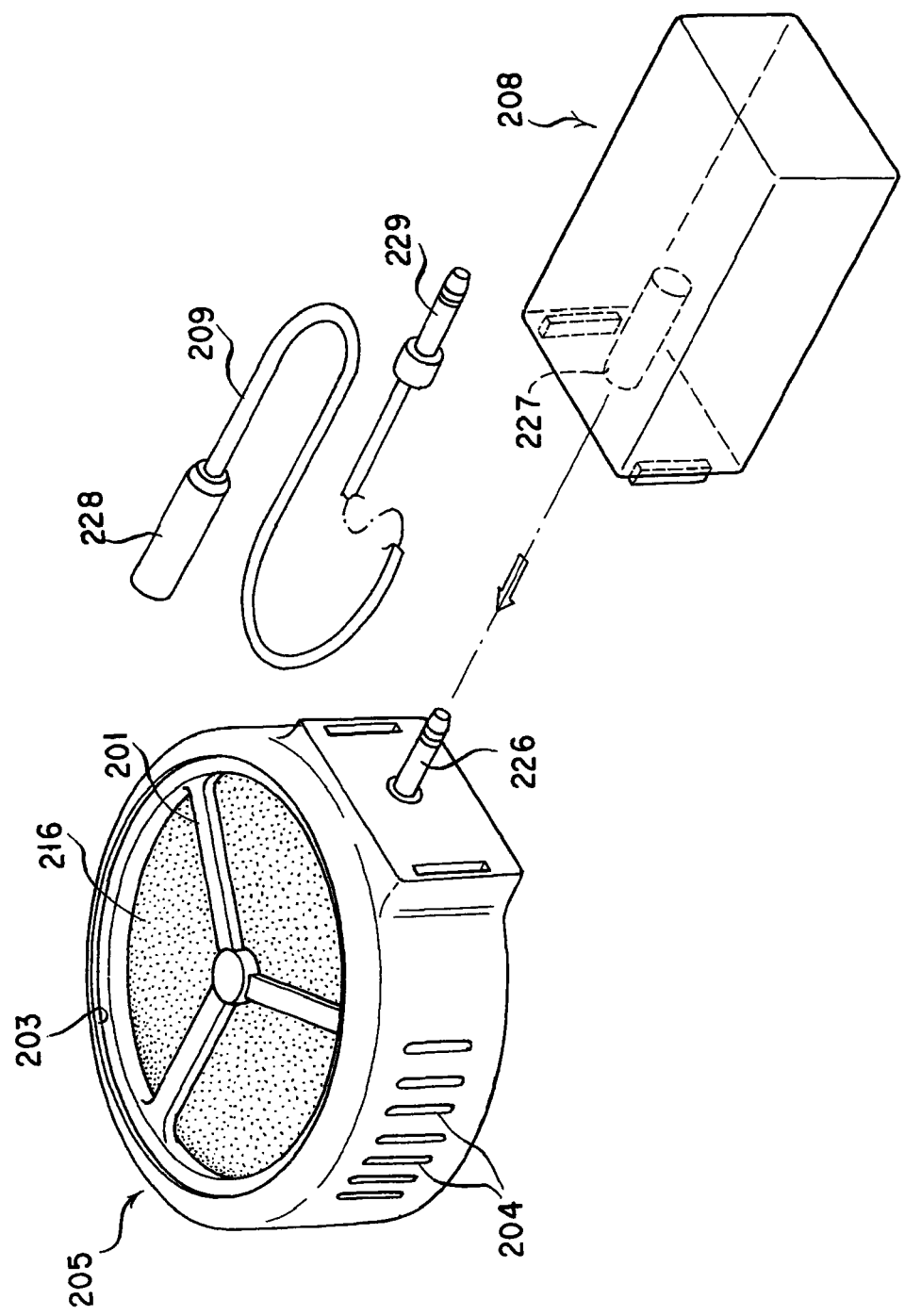
FIG. 20 is an explanatory view illustrating another example of the separation of a power casing body from an apparatus casing body.

With the connection cord 209 made detachable from both the main casing body 205 and the power casing body 208, as shown in FIG. 20 the main casing body 205 may be provided on its side face with a pin 226 projecting therefrom and the power casing body 208 provided in its side face with a jack 227 recessed therein. Then, the connection cord 20 may be provided at its one end with a jack 228 and at its other end with a pin 229. This permits the main casing body 205 and the power casing body 208 which are normally connected together via the connection cord 209 for use of the apparatus to be used in the state that they are directly connected together depending on particular circumstances of their use.

In an example of the use of the blower type chemical diffusing apparatus constructed as mentioned above, the main casing body 205 is fitted to a wrist, leg or waist portion of the body of a user via the wearing belt 221. On the other hand, the power casing body 208 is accepted in a pocket of clothing or a pant of the user or attached to the user's waist via another wearing belt 221. Then, the main casing body 205 and the power casing body 208 are connected together via the connection cord 209 and electric current is passed to the main casing body 205 from the power casing body 208 via the connection cord 209 to operate the air blower 202 in the main casing body 205. Then, the air blower 202 in the main casing body 205 draws air through the air inlet ports 203 and causes air drawn to pass through the chemical receptacle 201 included in the main casing body 205 and air entraining therein chemical volatilizing from the chemical receptacle 201 to emanate and diffuse laterally into the outside through the air discharge ports.

With a blower type chemical diffusing apparatus which as mentioned above comprises a main casing body 205 whereby air drawn by an air blower 202 is emanated together with a chemical volatilizing from a chemical receptacle 201 and entrained therein, a power casing body 208 separate from the main casing body 205 for accommodating a battery 224 as a power supply 207 for the air blower 202, and a connection cord 209 for connecting the main casing body 205 and the power casing body 208 to each other, the main casing body 205 is rendered small in size and light in weight by virtue of the fact that the power casing body 208 containing the battery 224 as the power supply 207 that is the weightiest of components of the apparatus is made separate from the main casing body 205 and that the main casing body 205 is allowed merely to contain the chemical receptacle 201 and the air blower 202. This allows a user, for example, to fit the main casing body 205 of the subject blower type chemical diffusing apparatus on its wrist or the like using a wearing belt 221 and to store the power casing body 208 in a pocket of its clothing and then to use the apparatus comfortably without feeling disagreeable with the size and weight of the apparatus.

Also, since the main casing body 205 and the power casing body 208 which are separated from each other are used in the state that they are connected together via the connection cord 209, even if either the main casing body 205 or the power casing body 208 in use happen to fall upon detaching from the user's body on which they are worn, the connection cord 209 coupling them together prevents them from being lost together.

Also, making the connection cord 209 removable from the main casing body 205 and the power casing 208 allows the connection cord 209 in the use of the apparatus after either the main casing body 205 or the power casing body 208 is fitted onto the user's body to be connected to it, thereby facilitating its fitting onto the user's body.

Further, providing the main casing body 205, the power casing body 208, the connecting cord 209 or each of two or all of them with a fitting means 206, e.g., a wearing belt 221, a hook 223, a pin or a clip, that enables the same to be fitted on any supporting object as desired allows the subject blower type chemical diffusing apparatus to be easily fitted onto any desired part of the user's body or any other supporting object.

Figure 21:
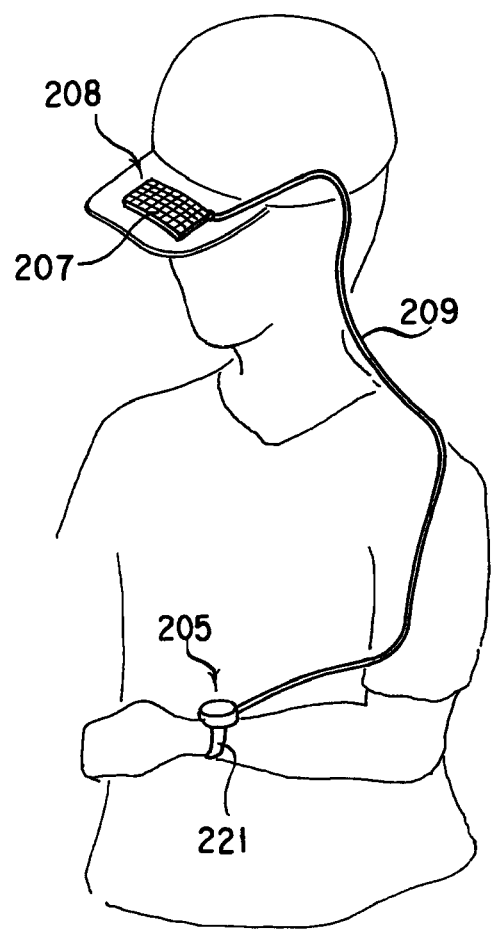
FIG. 21 is an explanatory view illustrating another example of use of a blower type chemical diffusing apparatus according to the present invention.

The blower type chemical diffusing apparatus according to the present invention is not limited to the particular forms of implementation illustrated above. For example, while the battery 224 contained as the power source 207 in the power casing body 208 is illustrated as comprising a dry cell or cells, it may be a solar cell or cells. Should a solar cell or cells be used as the power source 207 or the battery 224, the subject blower type chemical diffusing apparatus may be used as shown in FIG. 21 upon sticking the power casing body 208 onto the brim of a hat the user wears or a shoulder or the like of the user while fitting the main casing body 205 onto a wrist of the user by means of the wearing belt 221.

Figure 22:
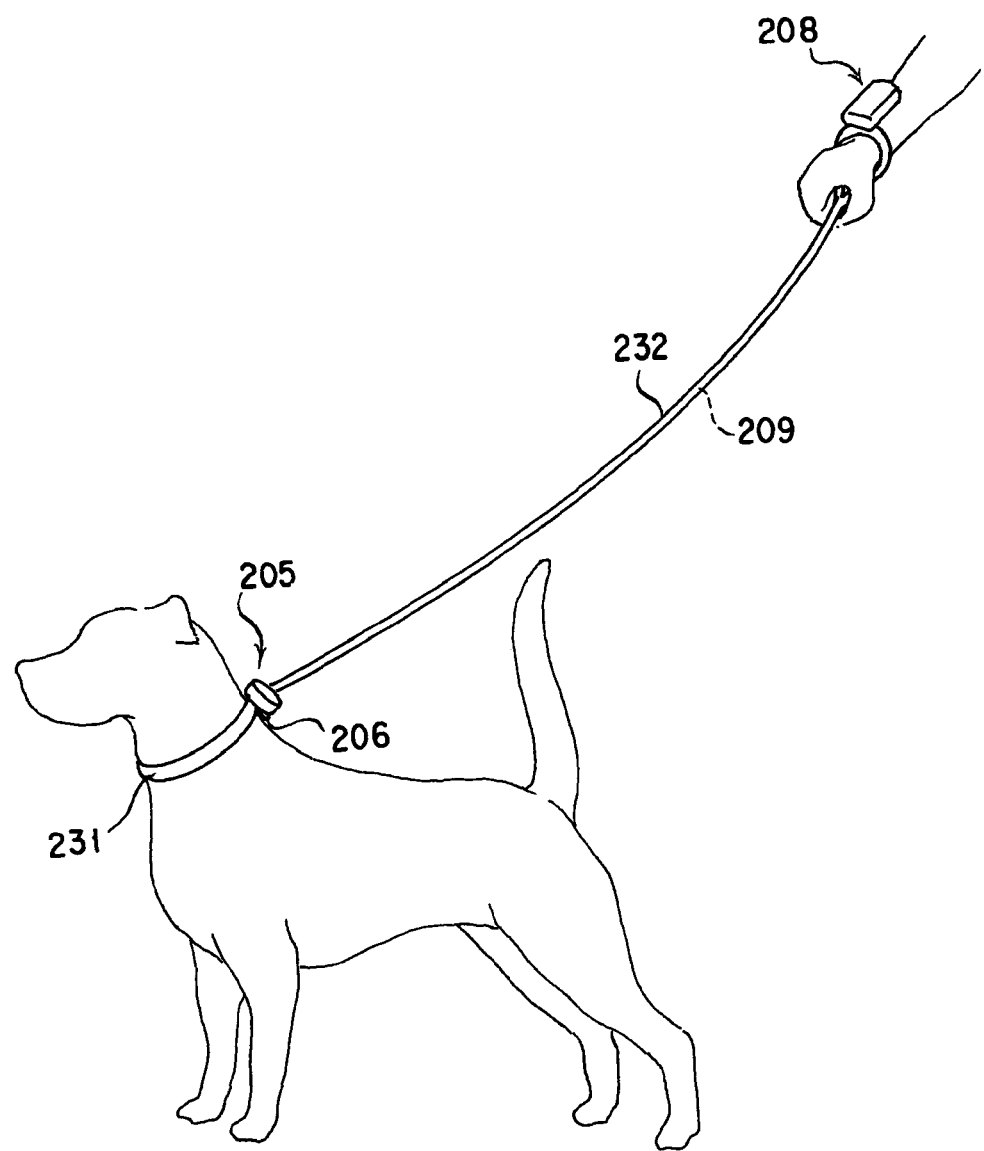
FIG. 22 is an explanatory view illustrating still another example of use of a blower type chemical diffusing apparatus according to the present invention.
Figure 23:
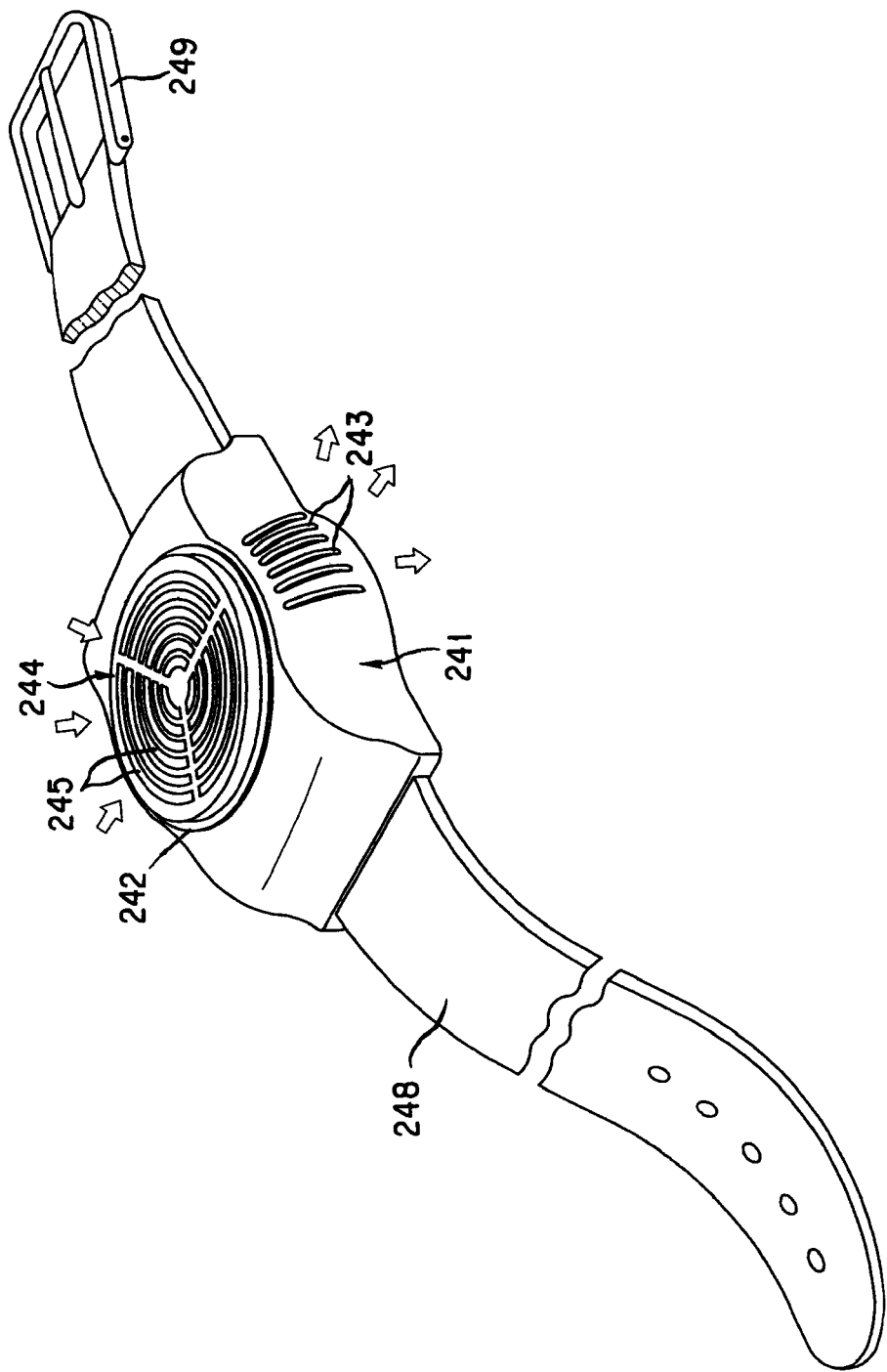
FIG. 23 is a perspective view illustrating a conventional blower type chemical diffusing apparatus.
Figure 24:
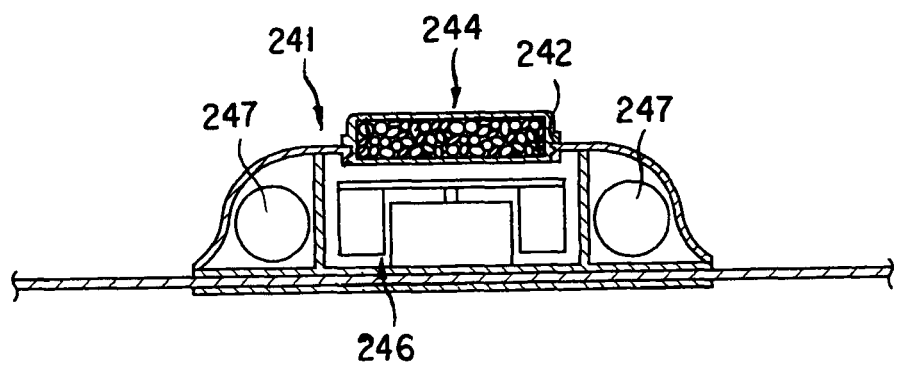
FIG. 24 is a side cross sectional view of the apparatus shown in FIG. 23.

Also, the subject blower type chemical diffusing apparatus can be used not only by a human being. For example, it may be used on a pet such as a dog. In this case, as shown in FIG. 22 the main casing body 205 may be fitted to a collar 231 of the pet by means of the fitting means 206 such as a hook and the power casing body 208 fitted onto a wrist or the like of its owner. Then, a connection cord 209 to extend between the main casing body 205 and the power casing body 208 may be put together with a lead 232 to extend between the pet's collar 231 and a owner's hand to form a cord incorporated lead for use on a pet.

Also, while in the forms of implementation described above, the fitting means 206 is shown as necessarily attached to the main casing body 205, this is not a limitation. A fitting means 206 as described may be attached to each of the main casing body 205, the power casing body 208 and the connection cord 209 or one or each of two of them. It is also possible to provide a subject blower type chemical diffusing apparatus omitting the fitting means 206.

Also, while in the forms of implementation described above, the main casing body 205 is shown as having the chemical receptacle 201 disposed adjacent to the air inlet ports 203, the chemical receptacle 201 may be disposed adjacent to the air discharge ports 204 when equipped with a suitable mounting means therefor. Further, it is possible to provide a chemical receptacle 201 for each of the air inlet and air discharge ports 203 and 204. It is also possible to disposed a chemical receptacle 201 at an inner or outer peripheral side of the sirocco fan 212 and then to integrate the chemical receptacle 201 with the air blower 202, or to have the sirocco fan 212 in the air blower 202 carry a chemical and to make it removable, or to attach or dispose a chemical receptacle 201 in the form of a porous sheet at the front of a large number of blades 213 in the sirocco fan 212 and to make it removable.

An explanation is next given in respect of a fourth form of implementation of the present invention.

Figure 25:
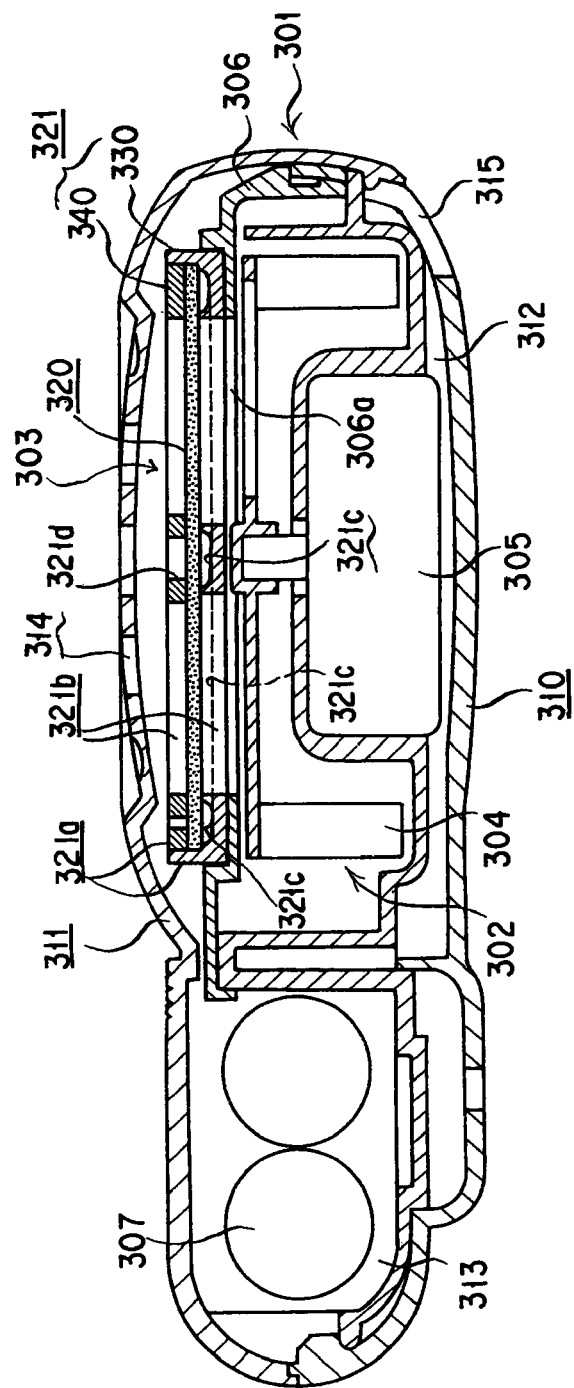
FIG. 25 is a cross sectional view illustrating a blower type chemical diffusing apparatus using a chemical cartridge that represents a forth form of implementation of the present invention.
Figure 26:
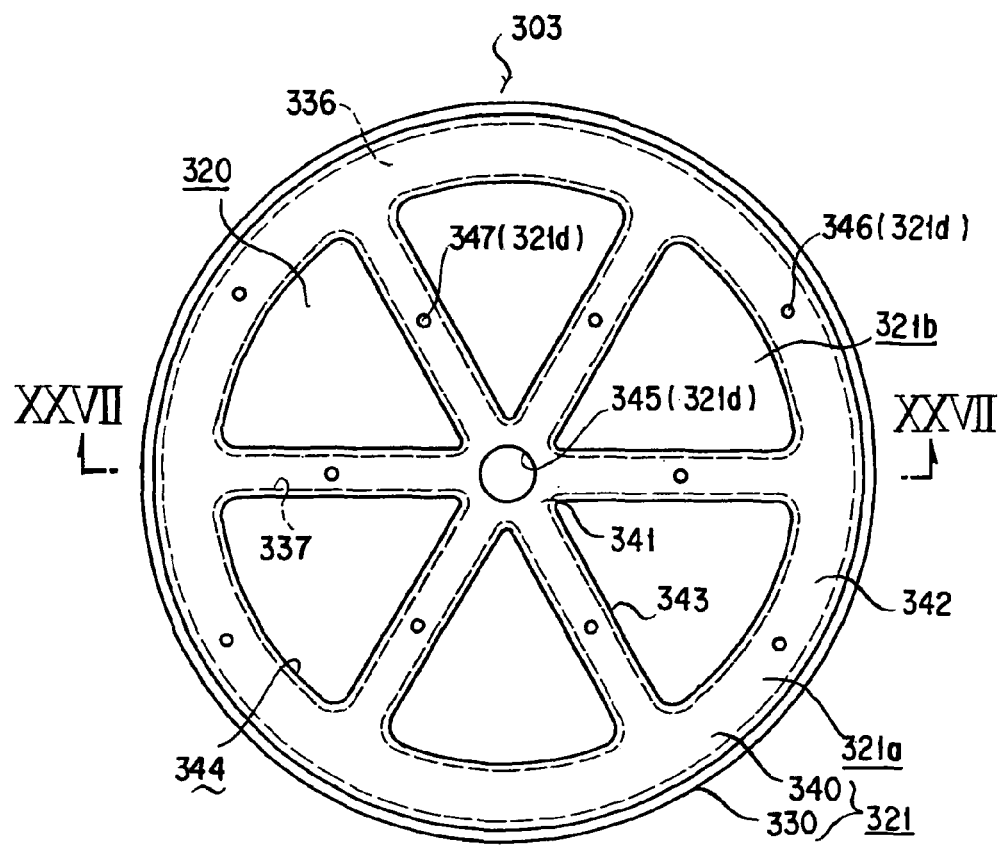
FIG. 26 is a top plan view of the chemical cartridge shown in FIG. 25.
Figure 27:
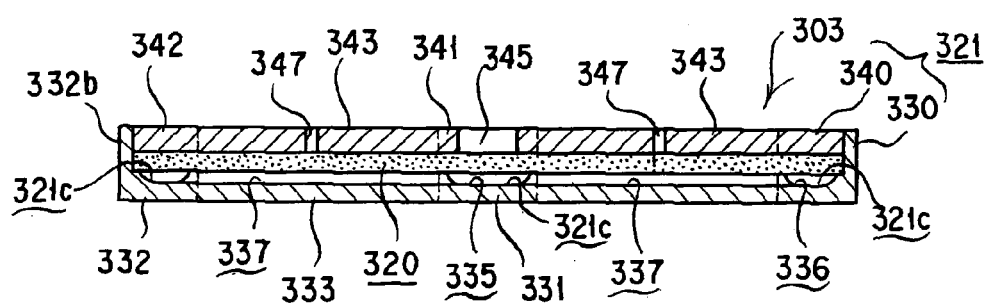
FIG. 27 is a cross sectional view of the chemical cartridge taken along the line XXVII-XXVII in FIG. 26.
Figure 28:
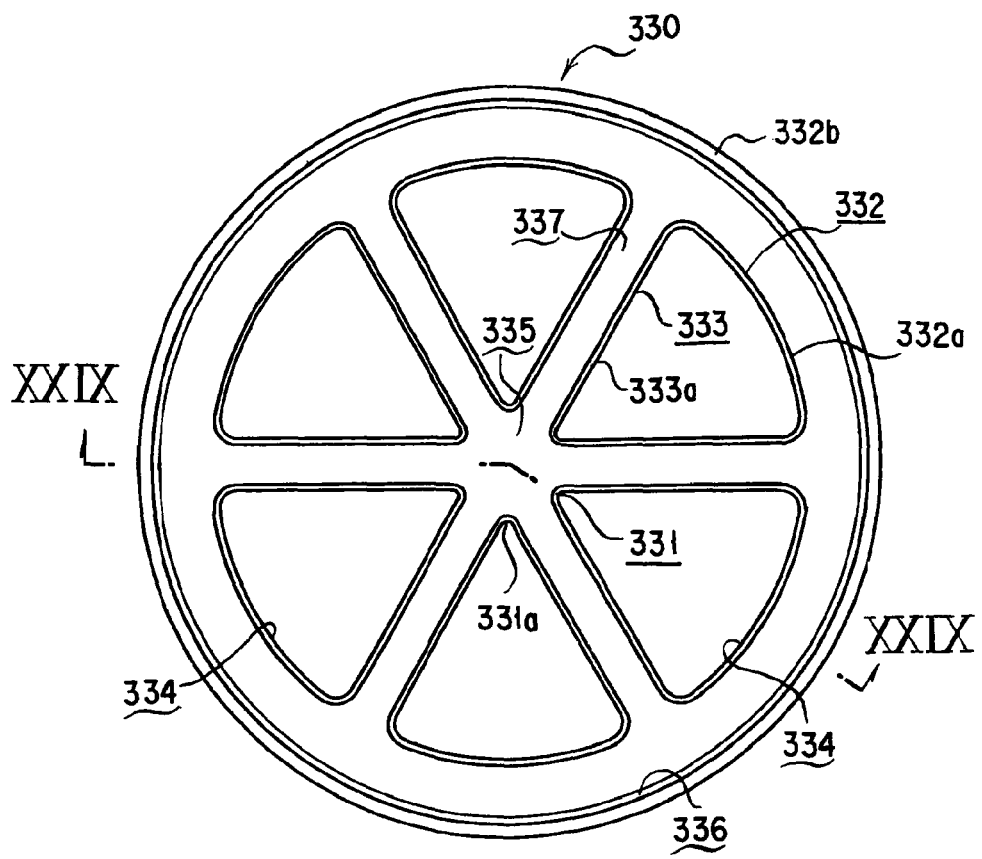
FIG. 28 is a top plan view illustrating a receptacle base member in the chemical cartridge shown.
Figure 29:
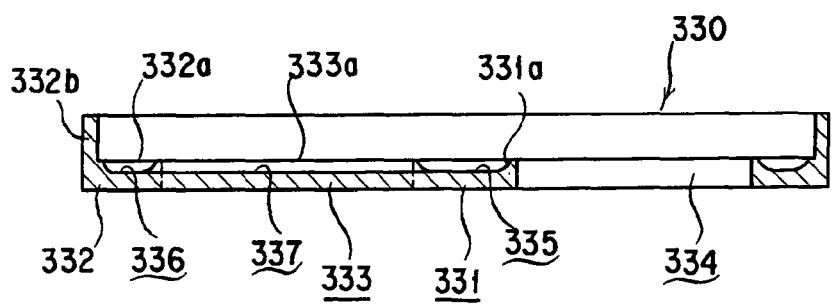
FIG. 29 is a cross sectional view of the base member taken along the line XXIX-XXIX in FIG. 28.

While with reference to FIG. 25 a chemical cartridge of the present invention will, as an example of its use, be described as applied to a blower type chemical diffusing apparatus using a chemical cartridge to diffuse a chemical into an atmosphere, it will be understood that the present invention when applied is not limited to this particular use.

As shown in FIG. 25, a main casing body 301 is provided with an air blower 302 and has a chemical cartridge 303 removably attached thereto wherein a fan 304 of the air blower 302 is rotated by a motor 305 to pass air through the chemical cartridge 303.

The main casing body 301 includes a base member 310 and a cover member 311, is formed with a blower mounting section 312 and a battery accepting section 313 and has an air inlet section 314 and an air discharge section 315.

The air blower 302 has a fan 304 and a motor 305 mounted in a housing 306 provided in the blower mounting section 312. The housing 306 has an air inlet port 306a communicating with the air inlet section 314 and also has an air discharge port (not shown) communicating with the air discharge section 315.

A battery 307 shown as comprising two dry cells is attached into the battery accepting section 313.

The cover member 311 is so connected to the main casing body 310 that it can be opened and closed whereby opening the cover member 311 allows the chemical cartridge 303 and the battery 307 to be removed and fitted in.

The chemical cartridge 303 is adapted to accept a chemical carrier or impregnated body 320 in the form of a porous or air permeable and liquid absorptive sheet impregnated with a chemical, and has a retainer or retainer receptacle 321 for retaining the chemical impregnated body 320.

In other words, since the chemical impregnated body 320, which is in the form of such a sheet, so liquid-absorptive and so weak in stiffness that it cannot sustain itself and if it is held directly by a hand, a chemical therein may adhere to the hand, it is held along a portion thereof with the retainer receptacle 321 to cause air to pass through other portions thereof.

So configured and arranged, the chemical cartridge 303 can be made thin because the chemical carrier or impregnated body 320 is here thin and the retainer receptacle 321 can be made thin.

Therefore, using such a chemical cartridge 303 allows thinning a blower type chemical diffusing apparatus as described.

The retainer receptacle 321 includes a holder section 321a holding upper and lower faces of the chemical impregnated body 320 from up and down and an air flow section 321b through which air flows.

Between the holder section 321a and the chemical impregnated body 320 there is formed a space 321c, which is open to the outside through a vent section 321d formed in holder section 321a so that air may be passed through the space 321c.

Preferably, the holder section 321a is formed with a recess where it is contacting the lower face of the chemical impregnated body 320 and the space 321c is formed between this recess and the lower face of the chemical impregnated body 320. And, the holder section 321a where it is contacting the upper face of the chemical impregnated body 320 is formed with vent holes constituting the vent section 321d and through which the space 321c (recess) is open to the outside.

So constructed, the retainer receptacle 321 can retain the chemical impregnated body 320 in the form of a sheet while maintaining its shape and can be held with a hand without the fear that chemical may contaminate the hand.

Also, while chemical in a region of the chemical impregnated body 320 where it is held by the holder section 321a is no volatilizing with air flow since air flow is prevented there, the chemical there is still volatilizing into the space 321c and from the latter to the outside through the air flow section 321b and thus allowed to emanate and diffuse into the environmental atmosphere.

While mention is specifically made below of the retainer receptacle 321 as regards its possible shape, it should be understood that this is by way of example only and not limiting the same.

The retainer receptacle 321 as shown in FIGS. 25 to 31 comprises a receptacle body member 330 and a receptacle cover member 340 by and between which the chemical impregnated body 320 is held and retained.

The receptacle body member 330 has a central support section 331, a peripheral support section 332 spaced from and around the central support section 330 and a plurality of intermediate support sections 333 connecting the peripheral support section 332 to the central support section 331 wherein a space defined with the central support section 331, the peripheral support section 332 and neighboring intermediate support sections 333 connected together by the peripheral support section 332 is open constituting an air flow section 334.

The central support section 331 has its upper face 331a formed with a recess 335 where it is contacting the lower face of the chemical impregnated body 320 and forming the space 321c elsewhere where it is opposed to the lower face of the chemical impregnated body 320.

The peripheral support sections 332 have its upper face 332a formed with an annular recess 336 where they are contacting the lower face of the chemical impregnated body 320 and forming the space 321c elsewhere they are opposed to the lower face of the chemical impregnated body 320.

The intermediate support sections 333 have their upper faces 333a formed with recesses 337 where they are contacting the lower face of the chemical impregnated body 320 which recesses communicate between the recess 335 and the annular recess 336, the upper faces 333a forming the space 321c elsewhere where they are opposed to the lower face of the chemical impregnated body 320.

The receptacle cover member 340 has a central hold section 341, a plurality of peripheral hold sections 342 spaced and around the central hold section 341 and a plurality of intermediate hold sections 343 connecting the peripheral hold section 342 to the central hold section 341 wherein a space defined with the central hold section 341, the peripheral hold section 342 and neighboring intermediate hold sections 343 connected together by the peripheral section 342 is open constituting an air flow section 344.

The central hold section 341 is identical in size to the central support section 331 and has a vent hole 345 opposed to the recess 335.

The peripheral hold section 342 is identical in size to the peripheral support section 332 and has a vent hole 346 opposed to the annular recess 336.

The intermediate hold sections 343 are identical in shape and size to the intermediate support sections 333, and the air flow sections 344 are opposed to the air flow sections 334 so that air smoothly flows through both the air flow sections 334 and 344. The intermediate hold sections 343 are formed with vent holes 347 so they are opposed to the recesses 337, respectively.

The receptacle body member 330 and the receptacle cover member 340 are detachably attached together.

In the form of implementation illustrated, the peripheral support section 332 has its outer edge raised from its upper face 332a to form a raised rim 332b in the form of a ring in which is the chemical impregnated body 320 and then the receptacle cover member 340 fitted.

As an alternative to this attachment design, the cover member 340 may be formed with such a raised rim which can be fitted over the outer edge or rim of the peripheral support section 332 to attach the cover member 340 to the receptacle body member 330. Yet alternatively, the receptacle body and cover members 330 and 340 may be provided with a pin and a hole which can be mated with each other to attach these members together.

Also, while in this firm of implementation the intermediate support and hold sections 333 and 343 are each shown comprising a plurality of subsections extending radially, not only may such subsections if adopted be in the form of a lattice but also each section 333, 343 may, for example, comprise a porous plate or the like.

So constructed and arranged as mentioned above, the retainer receptacle 321 acts to hold and support the chemical impregnated body 320 by supporting and holding a central region thereof with and between the central support and hold sections 331 and 341, a peripheral region thereof with and between the peripheral support and hold sections 332 and 342 and an intermediate region thereof with and between the intermediate support and hold sections 333 and 343.

This allows air flowing through the air flow sections 334 and 344 to pass through the chemical impregnated body 320.

Air is also allowed to flow through the space 321c formed between the recesses 335, 336 and 337 and the lower face of the chemical impregnated body 320.

So constructed and adapted as mentioned above, the chemical cartridge 303 is loaded in the main casing body 301 and in this form of implementation is attached to the upper face of the housing 306.

And, rotating the fan 304 causes air to flow through the chemical impregnated body 320 and chemical to emanate and diffuse into the environmental atmosphere.

Also, chemical in a region of the chemical impregnated body 320 which is held between each pair of support and hold sections is allowed to volatilize the space 321c and then to be entrained there in air flowing from the vent holes whereby air having chemical entrained therein is emitted into the atmosphere as the fan 304 is rotated.

Also, with the support sections 331, 332 and 333 formed on their upper faces with the recesses 335, 336 and 337 to form the space 321c and with the hold sections 341, 342 and 343 formed with the vent holes 345, 346 and 347 to make the space 321c open to the outside, it is possible to use the recesses 335, 336 and 337 to have a used chemical carrier 320 impregnated again with a chemical.

For example, a used chemical cartridge (with a chemical carrier depleted of chemical) 303 is removed from the main casing body 301 and liquid chemical is poured into the vent holes 345, 346 and 347 to supply and store the recesses 335, 336 and 337 therewith.

Liquid chemical stored in the recesses 335, 336 and 337 is allowed to impregnate into the chemical carrier 320 over its entire body to form an unused chemical cartridge impregnated with the chemical.

Since liquid chemical loaded in the recess 335 is impregnated into a center region of the chemical carrier 320, liquid chemical loaded in the annular recess 336 is impregnated into a peripheral region of the chemical carrier 320 and liquid chemical loaded in the recess 337 for communication is impregnated into an intermediate region of the chemical carrier 320, the chemical carrier 320 is impregnated with chemical quickly over its entire body.

Here, ways in which to supply a liquid chemical may visually check an amount of its supply using a calibrated dropping pipette, a dosage ampule, a metered container or a container with a metering cup, or a nozzle.

Also, since in supplying a chemical it is convenient if the time of its supply can visually be checked, it is desirable to use a chemical impregnated body 320 that may be of known type with an indicator displaying the time of its depletion.

While in the form of implementation described above the receptacle body member 330 is shown as having three support sections 331, 332 and 333 formed in their upper faces 331a, 332a and 333a with recesses 335, 336 and 337 and the receptacle cover member 340 as having three hold sections 341, 342 and 343 formed with vent holes 345, 346 and 347, not limiting the same and they may have only a pair of opposed support and hold sections formed with a recess and a vent hole, respectively, or two pairs of opposed support and hold sections formed with recesses and vent holes, respectively.

To with, there should be at least a pair of opposed support and hold sections formed with a recess and a vent hole, respectively.

Figure 32:
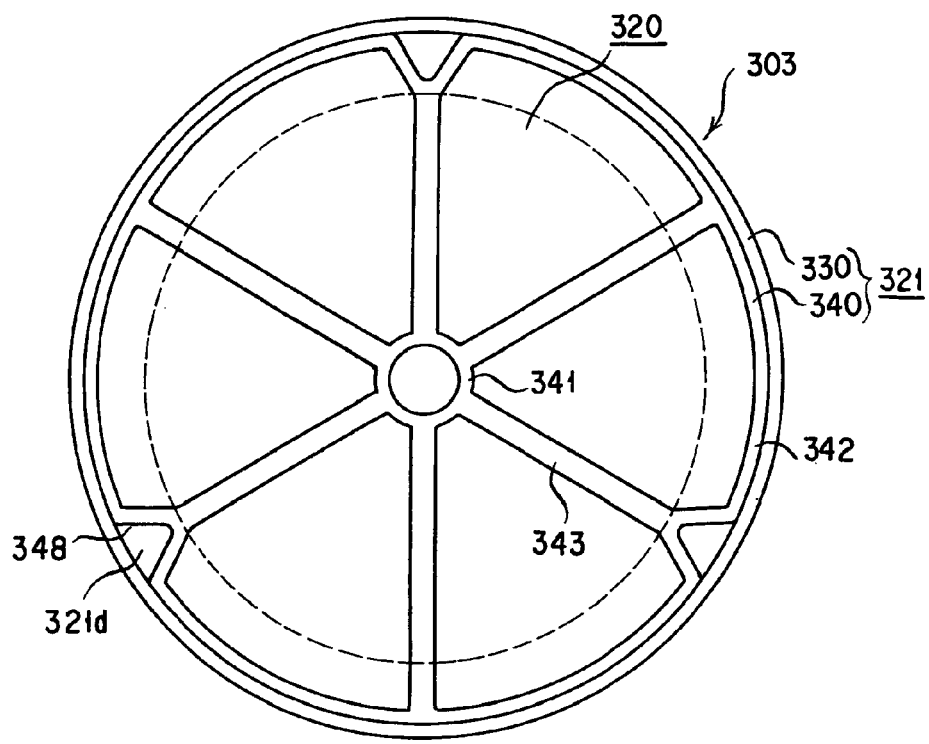
FIG. 32 is a top plan view illustrating a modification of the chemical cartridge according to the fourth form of implementation of the present invention.
Figure 33:
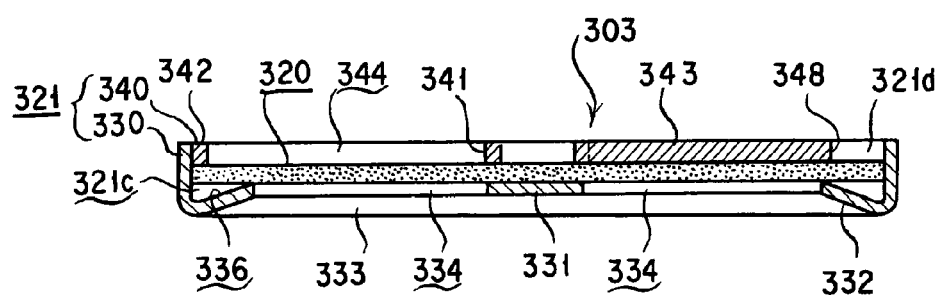
FIG. 33 is a cross sectional view of the modified chemical cartridge shown in FIG. 32.

For example, in a modification as shown in FIGS. 32 and 33, the peripheral support section 332 in the receptacle body member 330 may have its inner edge bent inwards to form an annular recess 336 whose cross section is in the form of a V, providing a space 321c between itself and the lower face of the chemical impregnated body 320.

On the other hand, portions of the peripheral hold section 342 in the receptacle cover member 340, e.g. portions where it continues to the intermediate hold sections, may be bent inwards to form recesses 348.

These recesses 348 are formed to provide vent sections 321d between themselves and the raised rim 332b of the receptacle body member 330.

While in this case the space 321c is formed beneath the chemical impregnated body 320, it may alternatively be formed above or both above and beneath the chemical impregnated body 320.

Not only is a chemical cartridge 303 according to the present invention used with a blower type chemical diffusing apparatus as described above, but also it can be directly attached to the fan in an air blower and may otherwise be integrated into the fan. Further, it can be disposed in either an air inlet or outlet side. Yet further, it can be attached at the blowout port of an air conditioner.

The chemical that can be impregnated into a chemical carrier or impregnated body of the present invention may be a insect pest control agent (insecticide, repellent, growth inhibitor, miticide, insect control essential oil or the like), aromatic, aromatic deodorant, deodorant, fungicide, disinfectant or vermin repellent, and especially such a chemical that is volatile at an ordinary temperature or air flow conditions.

Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical carrier thin and small.

The blank materials of which the chemical carrier of the present invention may be formed include natural and chemical fibers, nonwoven fabric (of natural, chemical and carbon fibers), resin net (polyester, polypropylene, polyvinyl chloride), cloth (woven or knitted), paper yarn (pulp, linter, synthetic paper). The material may be a formed body such in the form of a sheet, net, honeycomb, drain board, or lattice, a body yieldable to keep its shape when confined, or flocculate or sponge.

Of these materials, a sheet-like material of nonwoven fabric that excels in air permeability and chemical retention is preferred.

An explanation is next given in respect of a fifth form of implementation of the present invention.

Figure 34:
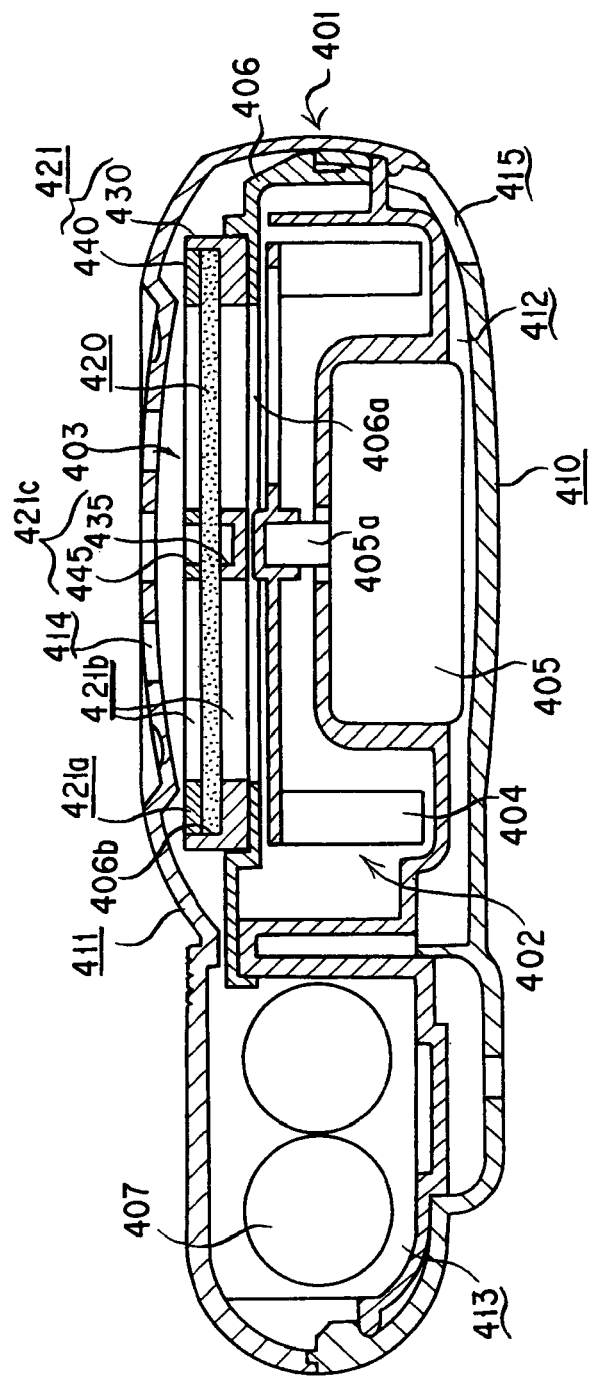
FIG. 34 is a cross sectional view illustrating a blower type chemical diffusing apparatus using a chemical cartridge that represents a fifth form of implementation of the present invention.

While with reference to FIG. 34 a chemical cartridge in another form of the present invention will, as an example of its use, be described as applied to a blower type chemical diffusing apparatus using a chemical cartridge to diffuse a chemical into an atmosphere, this particular use is not a limitation of the invention.

As shown in FIG. 34, a main casing body 401 is provided with an air blower 402 and has a chemical cartridge 403 removably attached thereto wherein a fan 404 of the air blower 402 is rotated by a motor 405 to pass air through the chemical cartridge 403.

The main casing body 401 includes a base member 410 and a cover member 411, is formed with a blower mounting section 412 and a battery accepting section 413 and has an air inlet section 414 and an air discharge section 415.

The air blower 402 has a fan 404 and a motor 405 mounted in a housing 406 provided in the blower mounting section 412. The housing 406 has an air inlet port 406a communicating with the air inlet section 414 and also has an air discharge port (not shown) communicating with the air discharge section 415.

A battery 407 shown as comprising two dry cells is attached into the battery accepting section 413.

The cover member 411 is so connected to the main casing body 410 that it can be opened and closed whereby opening the cover member 411 allows the chemical cartridge 403 and the battery 407 to be removed and fitted in.

The chemical cartridge 403 is adapted to accept a chemical carrier or impregnated body 420 in the form of a porous or air permeable and liquid absorptive sheet impregnated with a chemical, and has a retainer or retainer receptacle 421 for retaining the chemical impregnated body 420.

In other words, since the chemical impregnated body 420, which is in the form of such a sheet, so liquid-absorptive and so weak in stiffness that it cannot sustain itself and if it is held directly by a hand, a chemical therein may adhere to the hand, it is held along a portion thereof with the retainer receptacle 421 to cause air to pass through other portions thereof.

The retainer receptacle 421 includes a holder section 421a holding the chemical impregnated body 420 and an air flow section 421b through which air flows. The holder section 421a has a liquid pool recess 421c at its center, namely at the center of the retainer receptacle 421.

The housing 406 is formed with a recess 406b in which the retainer receptacle 421 is fitted and firmly seated. Then, rotating the fan 404 causes air to flow through the chemical impregnated body 420 and chemical to emanate and diffuse therewith into the environmental atmosphere.

So constructed as mentioned above, the chemical cartridge 403 after use, namely with chemical carrier 420 depleted of chemical, is removed from the main casing body 401, and liquid chemical is supplied into the liquid pool recess 421c and pooled there.

Liquid chemical pooled in the liquid pool recess 421c is allowed to impregnate the chemical carrier 420 progressively therewith over its entire body to form an unused chemical cartridge impregnated with the chemical.

Therefore, this is a chemical cartridge that can be repeatedly used by being re-supplied with chemical each time it is used up.

Since the chemical cartridge 403 is seated opposed to the fan 404 with its center opposed to the center of the fan 404, the center of the retainer receptacle 421 is opposed to that of the fan 404.

Thus, provided positioned at the center of the retainer receptacle 421, the liquid pool recess 421c in the use of the apparatus lies in an area where the air flows by rotation of the fan 404 are scarce, and little impedes them, permitting almost all of them to pass through the chemical impregnated body 420 and thereby to be consumed effectively to diffuse chemical into the atmosphere with little loss of the output of the air blower 402.

To with, the liquid pool recess 421c as shown in FIG. 34 is positioned to lie opposed to the center of the fan 404 coupled to the axis of rotation 405a of the motor 405 where the air flows from the fan 404 reach least around it and are substantially in no way impeded by the presence of the liquid pool recess 421c.

Also, the chemical cartridge 403 can be made thin because the chemical carrier or impregnated body 420 is here thin and the retainer receptacle 321 can be made thin.

Mention is next made of a specific shape of the retainer receptacle 421.

The retainer receptacle 421 as shown in FIGS. 34 and 35 comprises a receptacle body member 430 and a receptacle cover member 440 by and between which the chemical impregnated body 420 is held and retained.

The receptacle body member 430 has a central support section 431, a peripheral support section 432 spaced from and around the central support section 430 and a plurality of connecting support sections 433 connecting the peripheral support section 432 to the central support section 431 wherein a space defined with the central support section 431, the peripheral support section 432 and neighboring connecting support sections 433 connected together by the peripheral support section 432 is open constituting an air flow section 434.

The central support section 431 has its support face 431a formed with a recess 435.

The receptacle cover member 440 has a central hold section 441, a plurality of peripheral hold sections 442 spaced and around the central hold section 441 and a plurality of connecting hold sections 443 connecting the peripheral hold section 442 to the central hold section 441 wherein a space defined with the central hold section 441, the peripheral hold section 442 and neighboring connecting hold sections 443 connected together by the peripheral section 442 is open constituting an air flow section 444.

The central hold section 441 is identical in size to the central support section 431 and has a supply port 445 opposed to the recess 435, the supply port 445 and the recess 435 constituting the liquid pool recess 421c.

The peripheral hold section 442 is identical in size to the peripheral support section 432.

The connecting hold sections 443 are identical in shape and size to the connecting support sections 433, and the air flow sections 444 are opposed to the air flow sections 434 so that air smoothly flows through both the air flow sections 434 and 444.

The receptacle body member 430 and the receptacle cover member 440 are detachably attached together.

In the form of implementation illustrated, the peripheral support section 432 has its outer edge raised from its support face 432a to form a raised rim 432b in the form of a ring in which the chemical impregnated body 420 is fitted and then the receptacle cover member 440 is fitted.

As an alternative to this attachment design, the cover member 440 may be formed with such a raised rim which can be fitted over the outer edge or rim of the peripheral support section 432 to attach the cover member 440 to the receptacle body member 430. Yet alternatively, the receptacle body and cover members 430 and 440 may be provided with a pin and a hole which can be mated with each other to attach these members together.

Also, while in this firm of implementation the connecting support and hold sections 433 and 443 are each shown comprising a plurality of subsections extending radially, not only may such subsections if adopted be in the form of a lattice but also each section 433, 443 may, for example, comprise a porous plate or the like.

So constructed and arranged as mentioned above, the retainer receptacle 421 acts to hold and support the chemical cartridge 420 by supporting and holding a central region thereof with and between the central support and hold sections 431 and 441, a peripheral region thereof with and between the peripheral support and hold sections 432 and 442 and an intermediate region thereof with and between the connecting support and hold sections 433 and 443.

This allows air flowing through the air flow sections 434 and 444 to pass through the chemical impregnated body 420.

Thus, a used chemical cartridge (with a chemical carrier depleted of chemical) 403 is removed from the main casing body 401 and liquid chemical is poured into the supply port 445 to supply and store the recess 435, or the recess 435 and the supply port 445 therewith.

Liquid chemical stored in the recess 435 is allowed to impregnate into the chemical carrier 320 over its entire body to form an unused chemical cartridge impregnated with the chemical.

The depth of the liquid pool recess 421c can be determined depending on the amount of chemical to be supplied and has no particular limitation. If the lower face of the sheet and the upper face of the recess 435 abut each other, the depth may then be such that the liquid chemical supplied stays by its surface tension with the sheet body. If the depth is excessive, then some liquid may be left without contacting the sheet.

Mention is next made of a first modification of the chemical cartridge mentioned above.

Figure 36:
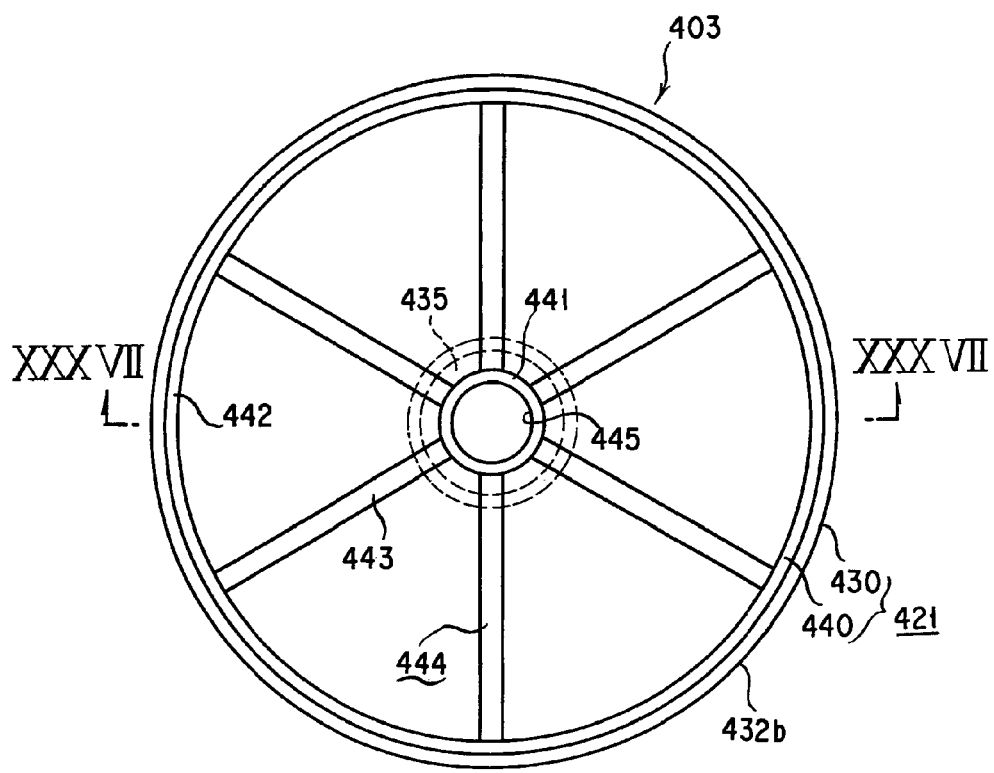
FIG. 36 is a top plan view illustrating a modification of the chemical cartridge shown in FIG. 35.
Figure 37:
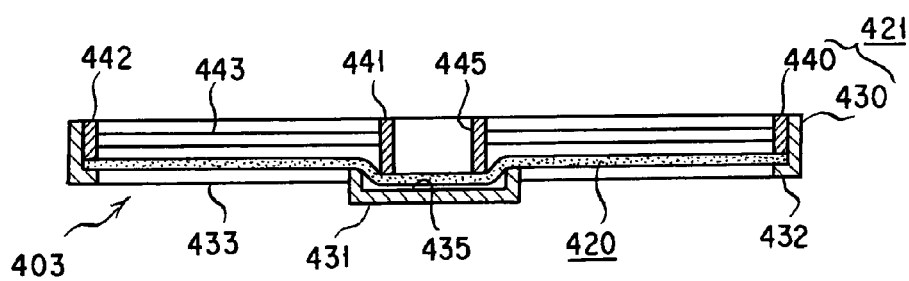
FIG. 37 is a cross sectional view of the chemical cartridge taken along the line XXXVII-XXXVII in FIG. 36.

As shown in FIGS. 36 and 37, the central support section 431 of the receptacle body member 430 is made larger in size than the central hold section 441 of the receptacle cover member 440 with recess 435 larger in size than the central hold section 441.

The central hold section of the cover member 440 is made thicker than the connecting section 443 so it protrudes downwards beyond each connecting section 443 to press the chemical impregnated body 420 into the recess 435 therewith.

This assists the chemical stored in the recess 435 to impregnate into the body the sheet.

If the sheet is positioned to lie close to or in contact with the base of the recess 435 as shown in FIG. 37, the depth of the recess 421c is determined depending on the amount of chemical to be supplied and need not be much since the chemical as soon as it is supplied will begin to permeate around.

The preceding form of implementation and its first modification mentioned above are particularly advantageous if the chemical impregnated body 420 is small. If it is large, it is desirable to form a liquid pool recess in the peripheral section as well so that chemical may be supplied into both the central and peripheral sections to permeate both from central towards peripheral and from peripheral towards central.

This is effective to have chemical permeate quickly into the entire body of a sheet and thus advantageous in the man manufacture of such products.

Figure 38:
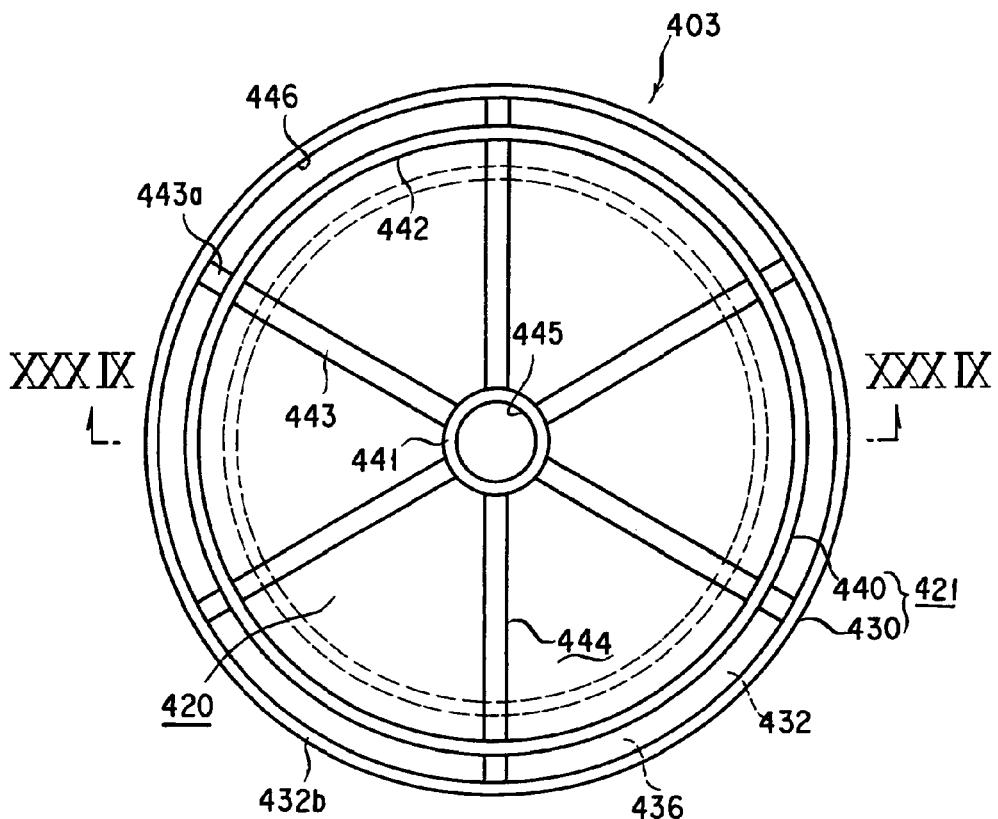
FIG. 38 is a top plan view illustrating a second modification of the chemical cartridge according to the fifth form of implementation of the present invention.
Figure 39:
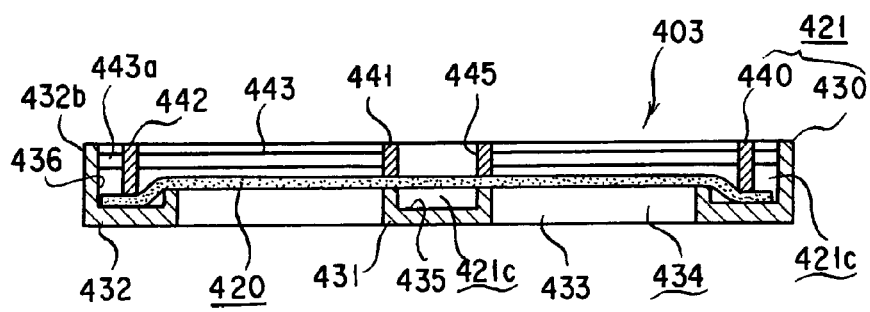
FIG. 39 is a cross sectional view of the modified chemical cartridge taken along the line XXXIX-XXXIX in FIG. 38.

For example, in a second modification as shown in FIGS. 38 and 39, in the receptacle body member 431 the central support section 431 is formed with the recess 435 and the peripheral section 432 is formed with a peripheral recess 436 that is e.g., annular.

The central hold section 441 in the cover member 440 is formed with the supply port 445. Each connecting section 443 is extend outwards to project from each peripheral hold section 442, forming an extension 443a in contact with the raised edge 432b while providing a gap between the peripheral hold section 442 and the raised edge 432b to constitute a peripheral supply port 446.

A peripheral recess 436 thus formed is made to act as a liquid pool recess 421c in the peripheral section.

In this second modification, the peripheral hold section 442 is made thicker than the central hold section 441 to press a peripheral edge of the chemical impregnated body 420 into the peripheral recess 436 to assist the chemical to permeate into the chemical impregnated body 420.

Figure 40:
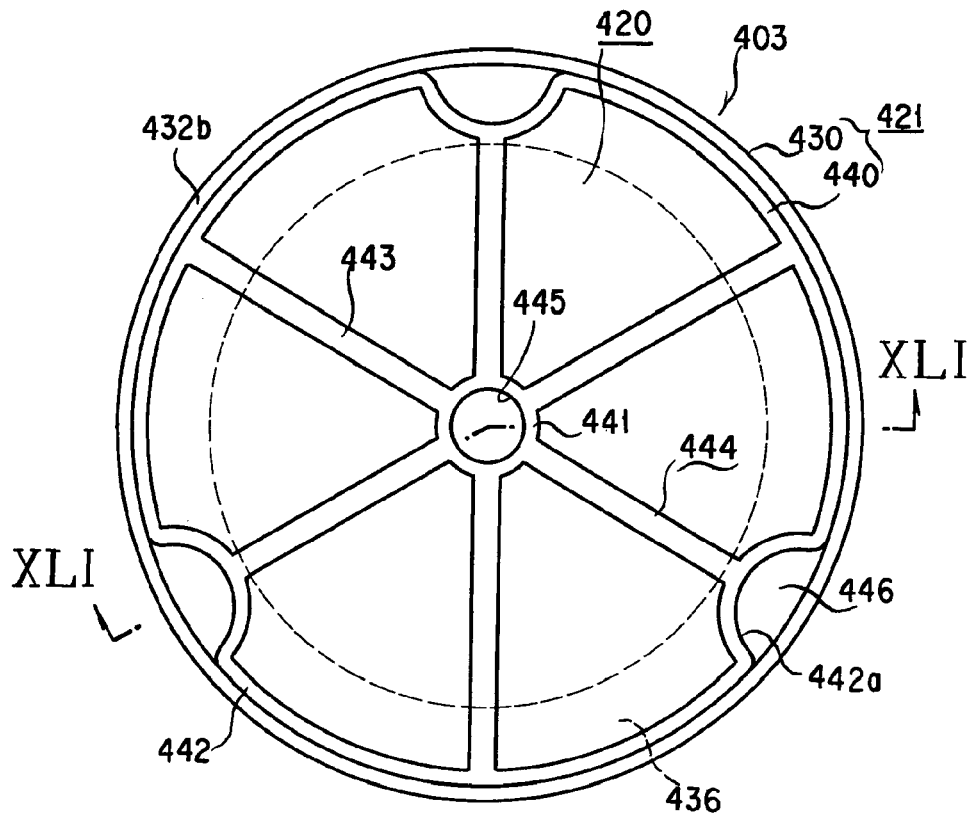
FIG. 40 is a top plan view illustrating a third modification of the chemical cartridge according to the fifth form of implementation of the present invention.
Figure 41:
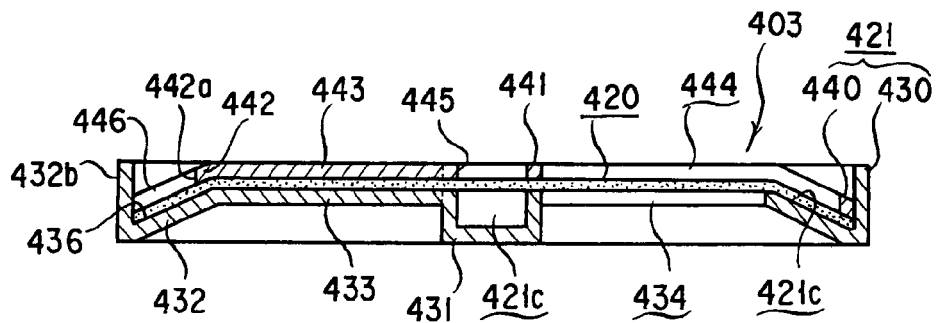
FIG. 41 is a cross sectional view of the modified chemical cartridge taken along the line XLI-XLI in FIG. 40.

Also, in a third modification as shown in FIGS. 40 and 41, the peripheral support section 432 of the receptacle body member 430 is bent downwards so that a peripheral recess 436 is formed by the bent peripheral support section 432 and the raised edge 432b.

The connecting sections 443 of the cover member 440 are also bent downwards so the peripheral hold section 442 conforms to the bent peripheral support section 432.

This presses a peripheral edge of the chemical impregnated body 420 against the peripheral support section 432.

Portions of the peripheral hold section 442 of the cover member 440, e.g., where it connects to the connecting sections 443, are deformed to form dents 442a there, thereby forming openings between these dents and the raised edge 432b, respectively, to constitute peripheral supply ports 446.

Figure 42:
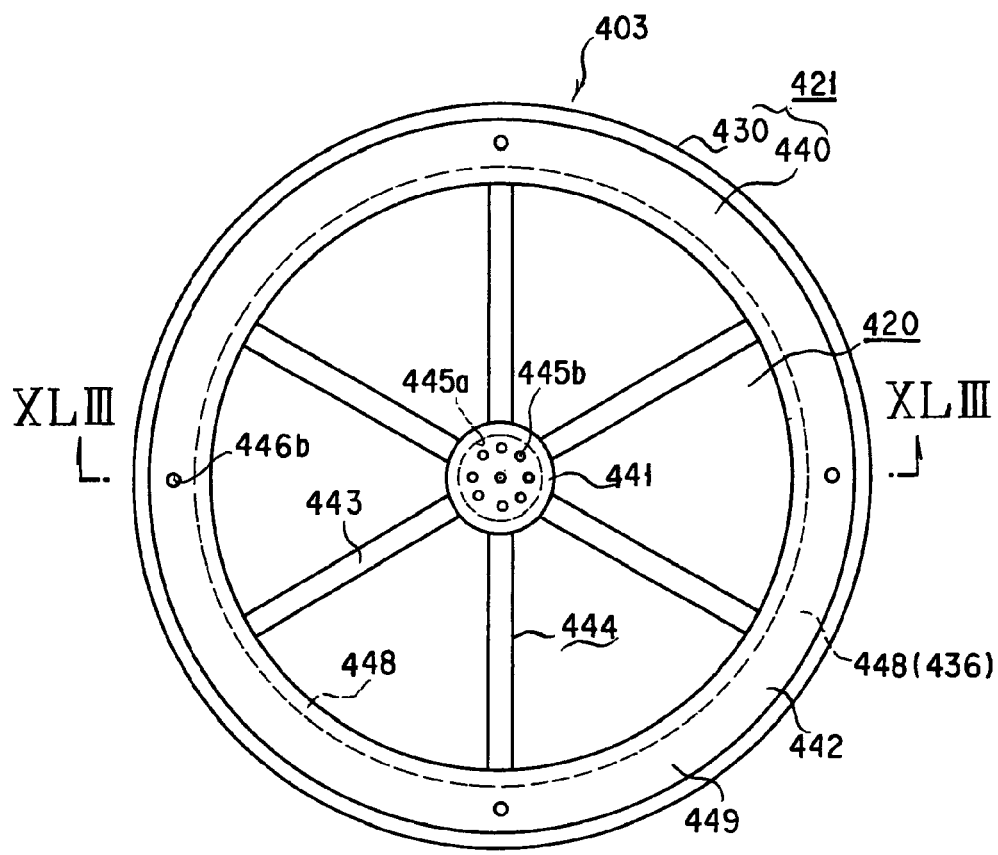
FIG. 42 is a top plan view illustrating a fourth modification of the chemical cartridge according to the fifth form of implementation of the present invention.
Figure 43:
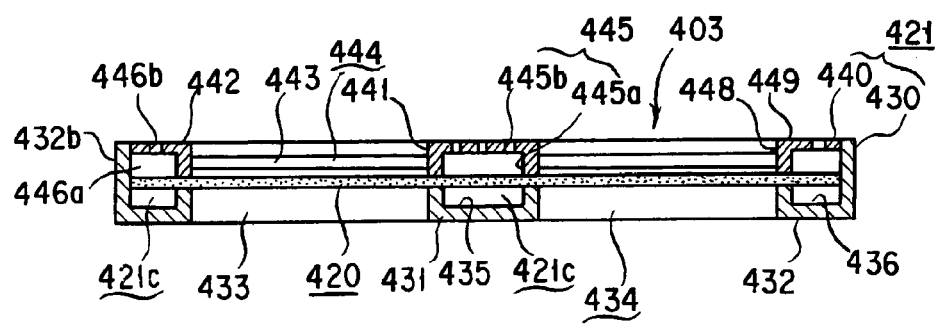
FIG. 43 is a cross sectional view of the modified chemical cartridge taken along the line XLIII-XLIII in FIG. 42.

Also, in a fourth modification as shown in FIGS. 42 and 43, the central hold section 441 of the cover member 440 is formed with a downward facing recess 445a which is in turn formed on its top face with a plurality of small supply holes 445b whereby the downward facing recess 445a and the supply holes 445b constitute a supply port 445 and the supply port 445 and the recess 435 constitute a liquid pool recess 421c.

The peripheral hold section 442 of the cover member 440 comprises an inner vertical subsection 448 and a top flat subsection 449 which define a downward facing recess 446a wherein the top flat subsection is formed with peripheral supply holes 446b which together with the downward facing recess 446a constitute a peripheral supply port 446 and the latter and the peripheral recess 436 constitute a liquid pool recess 421c in the peripheral section.

Also, it is possible to enhance the surface tension of liquid chemical with the sheet. To this end, the inner base of each of the recesses may be processed by embossing or the like to impart surface irregularities thereto, to create small spaces in the form of a lattice, or a plurality of raised edges may be provided to form grooves.

As mentioned before, ways in which to supply a liquid chemical into a liquid pool recess 421c may visually check an amount of its supply using a calibrated dropping pipette, a dosage ampule, a metered container or a container with a metering cup, or a nozzle.

Also, since in supplying a chemical it is convenient if the time of its supply can visually be checked, it is desirable to use a chemical impregnated body 420 that may be of known type with an indicator displaying the time of its depletion.

Further, not only is a chemical cartridge 403 according to the present invention used with a blower type chemical diffusing apparatus as described above, but also it can be directly attached to the fan in an air blower and may otherwise be integrated into the fan. Further, it can be disposed in either an air inlet or outlet side. Yet further, it can be attached at the blowout port of an air conditioner.

The chemical that can be impregnated into a chemical carrier or impregnated body 420 of the present invention may be a insect pest control agent (insecticide, repellent, growth inhibitor, miticide, insect control essential oil or the like), aromatic, aromatic deodorant, deodorant, fungicide, disinfectant or vermin repellent, and especially such a chemical that is volatile at an ordinary temperature or air flow conditions.

Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical carrier thin and small.

The blank materials of which the chemical carrier of the present invention may be formed include natural and chemical fibers, nonwoven fabric (of natural, chemical and carbon fibers), resin net (polyester, polypropylene, polyvinyl chloride), cloth (woven or knitted), paper yarn (pulp, linter, synthetic paper). The material may be a formed body in the form of a sheet, net, honeycomb, drain board or lattice, a body yieldable to keep its shape when confined, or flocculate or sponge.

Of these materials, a sheet-like material of nonwoven fabric that excels in air permeability and chemical retention is preferred.

An explanation is next given in respect of a sixth form of implementation of the present invention.

Figure 44:
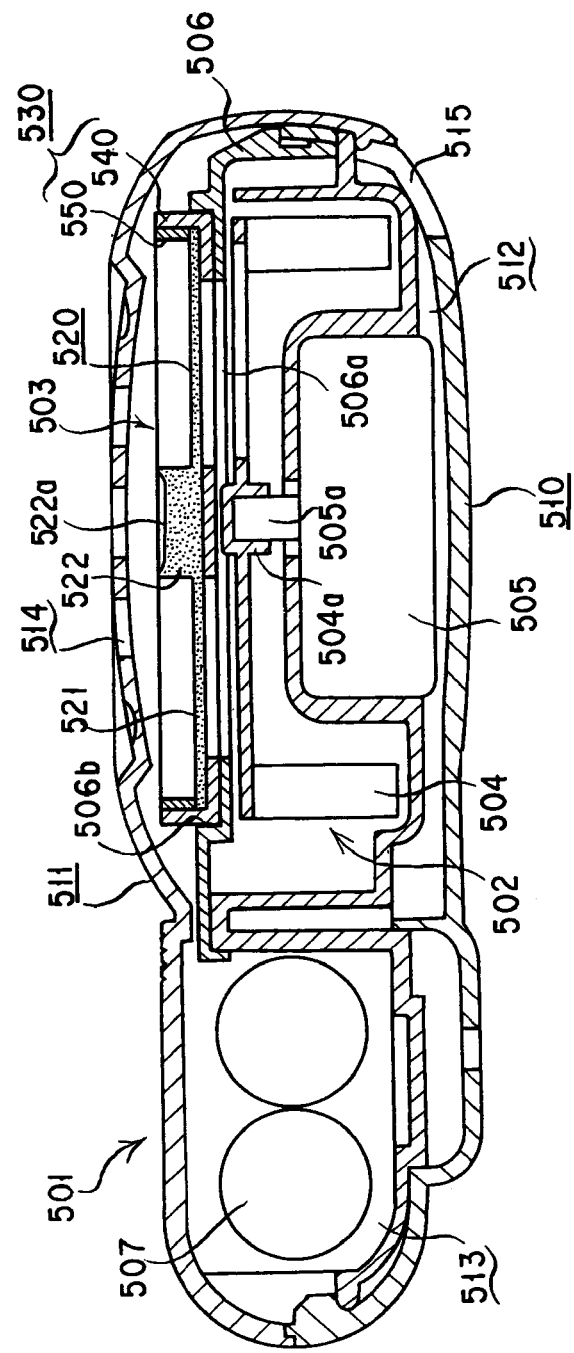
FIG. 44 is a cross sectional view illustrating a blower type chemical diffusing apparatus using a chemical cartridge that represents a sixth form of implementation of the present invention.

While with reference to FIG. 44 a chemical cartridge in another form of the present invention will, as an example of its use, be described as applied to a blower type chemical diffusing apparatus using a chemical cartridge to diffuse a chemical into an atmosphere, it will be understood that the present invention when applied is not limited to this particular use.

As shown in FIG. 44, a main casing body 501 is provided with an air blower 502 and has a chemical cartridge 503 removably attached thereto wherein a fan 504 of the air blower 502 is rotated by a motor 505 to pass air through the chemical cartridge 503.

The main casing body 501 includes a base member 510 and a cover member 511, is formed with a blower mounting section 512 and a battery accepting section 513 and has an air inlet section 514 and an air discharge section 515.

The air blower 502 has a fan 504 and a motor 505 mounted in a housing 506 provided in the blower mounting section 512. The housing 506 has an air inlet port 506a communicating with the air inlet section 514 and also has an air discharge port (not shown) communicating with the air discharge section 515.

A battery 507 shown as comprising two dry cells is attached into the battery accepting section 513.

The cover member 511 is so connected to the main casing body 510 that it can be opened and closed whereby opening the cover member 511 allows the chemical cartridge 503 and the battery 507 to be removed and fitted in.

The chemical cartridge 503 is adapted to accept a chemical impregnated body 520 in the form of a sheet and has a retainer or retainer receptacle 530 for retaining the chemical impregnated body 520.

In other words, since the chemical impregnated body 520, which is in the form of such a sheet, so liquid-absorptive and so weak in stiffness that it cannot sustain itself and if it is held directly by a hand, a chemical therein may adhere to the hand, it is held along a portion thereof with the retainer receptacle 530 to cause air to pass through other portions thereof.

This permits the chemical cartridge 520 to be made thin and easy to handle.

The chemical impregnated body 520 comprises a carrier 521 in the form of a sheet impregnated with and retaining therein a chemical in a given amount.

The sheet-like carrier 521 of the chemical impregnated body 520 has a high liquid retention region 522 that can at a time be impregnated with and capture a large amount of chemical, which progressively permeates into the carrier 521 over its entire body.

So constructed and adapted as mentioned above, a chemical cartridge 503 when used out (when chemical contained in the carrier 521 of the chemical impregnated body 520 is depleted or completely diffused into the environmental atmosphere and the carrier 521 has no such chemical contained therein) allows re-supply by dropping and thereby supplying a large amount of chemical into the high liquid retention region 522 to allow the chemical to progressively permeate into the carrier 521 over its entire body until the carrier 521 is fully charged with the chemical, thereby reproducing an unused chemical cartridge.

Therefore, this is a chemical cartridge that can be repeatedly used by being re-supplied with chemical each time it is used up.

Also, since in the stage of manufacture as well, the carrier 521 of a chemical impregnated body 520 can be supplied in its high liquid retention region 522 with a large amount of chemical to allow it to permeate into the carrier 521 progressively over its entire body, it is possible to impregnate the carrier 521 uniformly over its entire body with chemical.

Figure 45:
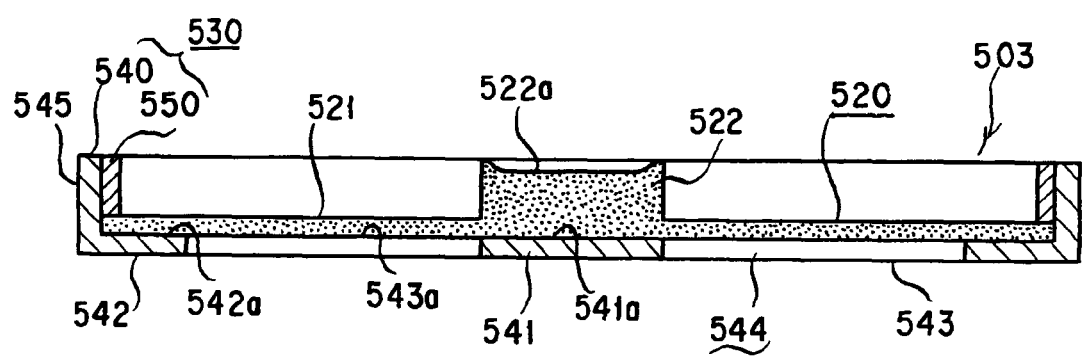
FIG. 45 is a cross sectional view of the chemical cartridge shown in FIG. 44.
Figure 46:
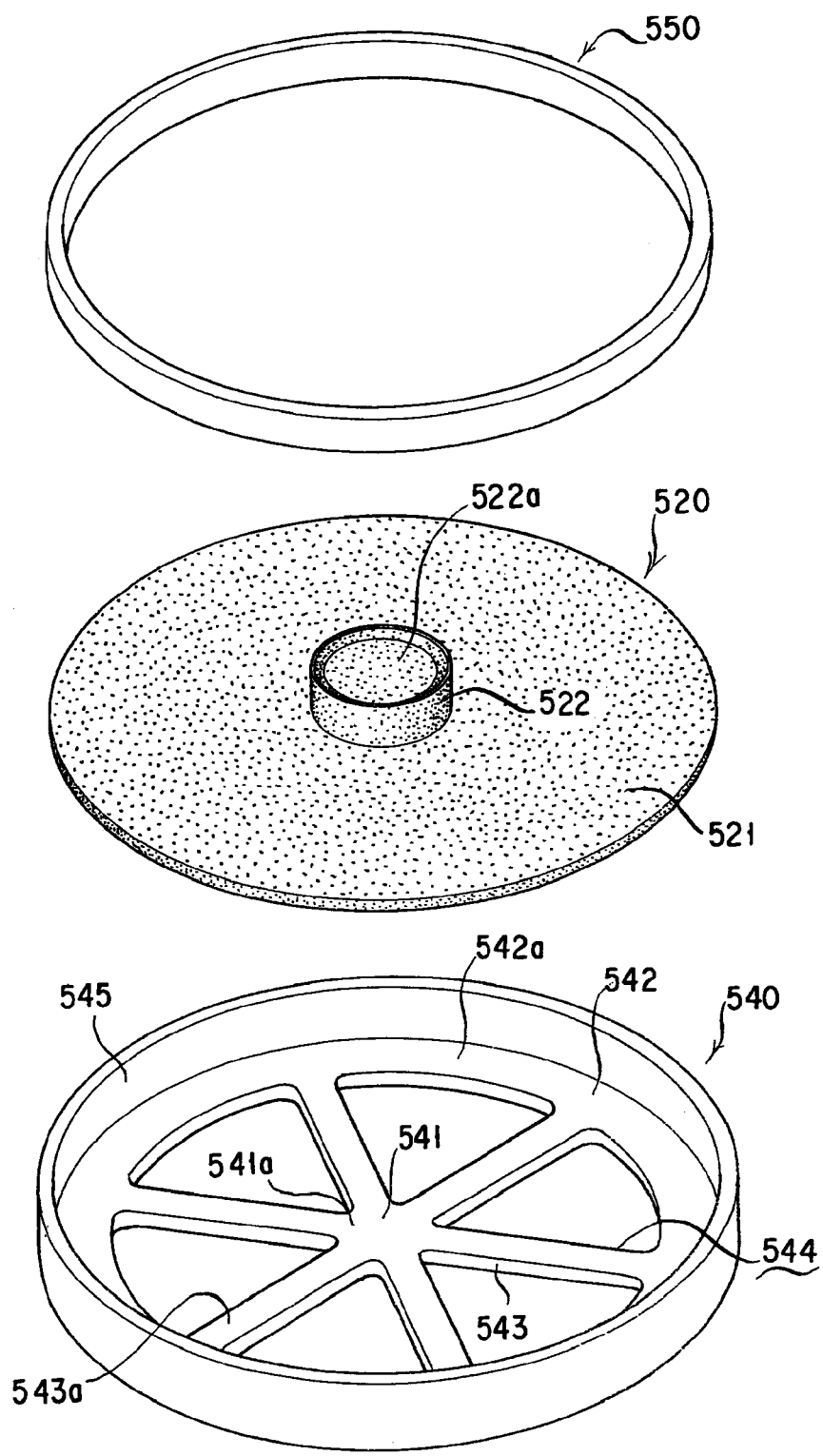
FIG. 46 is a decomposed perspective view of the chemical cartridge shown in FIG. 44.

Mention is next made specifically of a presently preferred but not exclusive example of the chemical cartridge 503 with reference to FIGS. 45 and 46.

The carrier 521 of this chemical impregnated body 520 is in the form of a sheet whose central part is thicker than elsewhere thereof, constituting the high liquid retention region 522.

The high liquid retention region 522 is formed in its top with a recess 522a to assist chemical when supplied to be absorbed into its inside easily.

Even if the liquid absorptivity (the magnitude of an amount of liquid that can be absorbed in unit area) of the carrier 521 is uniform over its entire area, its central area made thin can absorb a large amount of chemical and can constitute the high liquid retention region 522.

Preferably, however, the carrier 421 can be made more liquid absorptive in its central part than in the other parts, permitting this part (the high liquid retention region 522) to be impregnated with a maximum amount of chemical.

However, if the high liquid retention region 522 of the carrier 521 is made higher in liquid absorptiveness than its other regions, this region can be made equal in thickness to the other regions.

Thus, the high liquid retention region 522 of a carrier 521 can in effect be a region where the amount of liquid that can be absorbed per unit volume is larger than elsewhere thereof.

Also, the high liquid retention region 522 may have any shape, i.e., not only round as mentioned but also rectangular, semicircular or raising, depending on its blank material used.

The retainer receptacle 530 comprises a receptacle body member 540 and a hold member 550 by and between which the chemical impregnated body 520 is held and retained.

The receptacle body member 540 has a central support section 541, a peripheral support section 542 and a plurality of connecting support sections 543 connecting the peripheral support section 542 to the central support section 541 wherein a space defined with the central support section 541, the peripheral support section 542 and neighboring connecting support sections 543 connected together by the peripheral support section 542 is open constituting an air flow section 544.

The peripheral support section 542 has its outer edge raised from its upper face to form a raised edge 545 in the form of a ring.

The chemical impregnated body 520 is placed on and supported by the upper faces 541a, 542a and 543a of the central and peripheral and connecting support sections 541, 542 and 543.

The hold member 550 is in the form of a ring that can be fitted with the ring-shaped raised edge 545 to hold a peripheral part of the chemical impregnated body 520 by and between the hold member 50 and the peripheral support section 542.

The chemical cartridge 503 as shown in FIG. 44 is mounted fitting with its mounting section 506b of the housing 506 and opposed to the fan 504 of the air blower 502 so that the central part 504a of the fan 404 little in air flow (namely, where the axis of rotation 505a of the motor 505 is coupled thereto) is opposed to the central part (the high liquid retention region 522) of the carrier 521 of the chemical impregnated body 520.

Thus, through the high liquid retention region 522 there will air flow much less than elsewhere around it to allow air to flow smoothly through the chemical impregnated body 520 without being impeded by the high liquid retention region 522 despite its thickness.

Being placed on the upper face 541a of the central supporting section 541 of the retainer receptacle 540, the high liquid retention region 522 supplied with a large amount of chemical when it is refilled to add to its weight is prevented from coming down.

Also, being identical to or larger than the high liquid retention region 522 in size, the central support section 541 prevents liquid chemical from leaking down from the lower face of the high liquid retention region 522 when it is supplied with a large amount of liquid chemical.

The central support section 541 may be in the form of a shallow and dented dish.

A mention is next made of modifications of this form of implementation.

The central support section 541 of the receptacle body member 540 may be smaller in size than the high liquid retention region 522. Further, the connecting sections 643 may only be six but also four, three or the like in number.

Figure 47A:
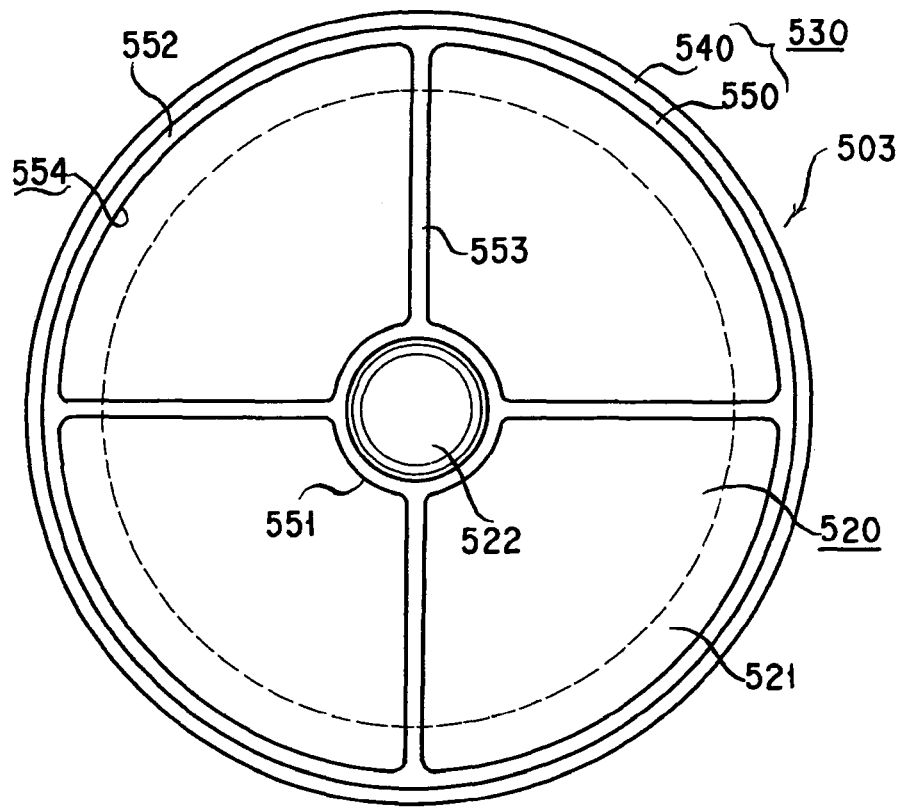
FIGS. 47A and 47B are a top plan and a cross sectional view illustrating a first modification of the chemical cartridge according to the sixth form of implementation of the present invention.
Figure 47B:
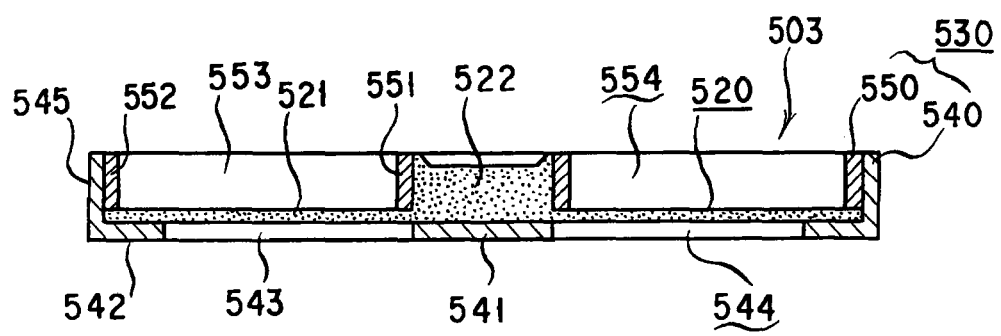

In a first modification as shown in FIGS. 47A and 47B, the hold member 550 may have a central ring 551, a peripheral ring 552 and a plurality of stays 553 connecting the central and peripheral rings 551 and 552 to form openings 554 and may so be made that the central ring 551 fits with the high liquid retention region 522 and the peripheral ring 552 fits with the ring-shaped raised edge 545 of the receptacle body member 540.

This allows the central ring 551 to provide an indication of chemical dropped and supplied.

In this case, the central support section 541 of the receptacle body member 540 may be in the form of a ring.

Also, in this case, the central ring 551 of the hold member 550 may abut on the upper face of the high liquid retention region 522 to hold it with the central support section 541.

Also, the central ring 551 may be large in height than the high liquid retention region 522 to prevent liquid chemical supplied from leaking.

Figure 48A:
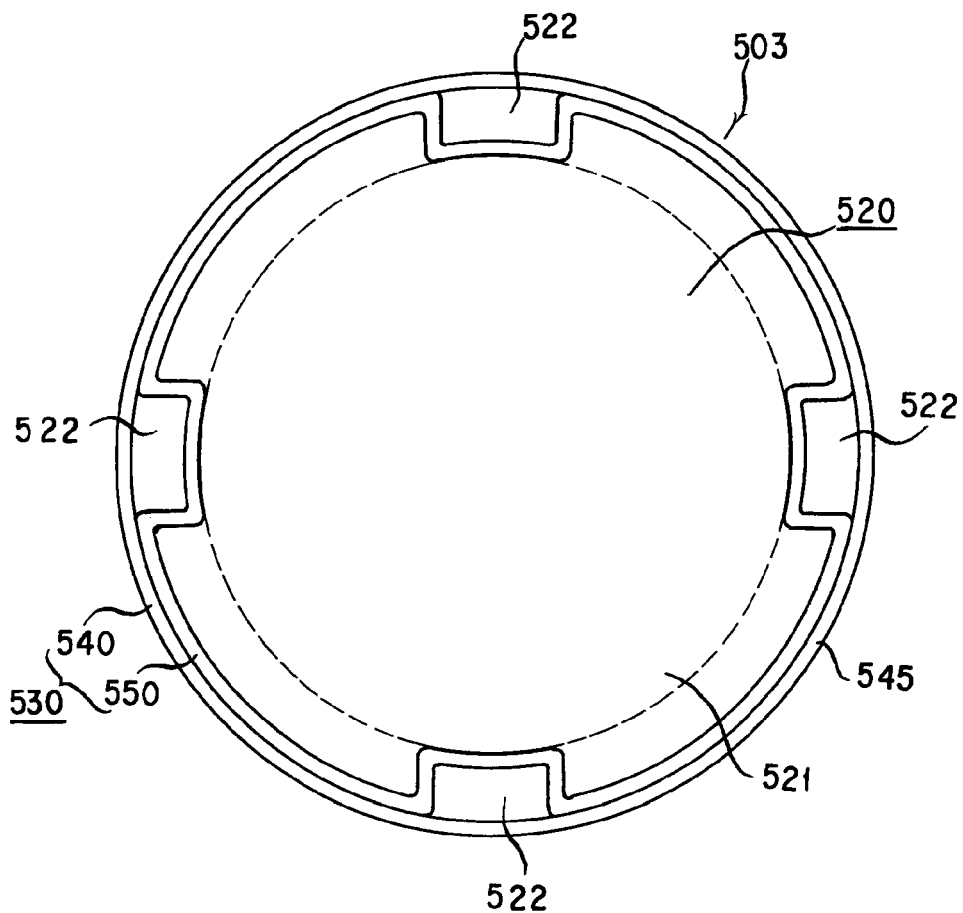
FIGS. 48A and 48B are a top plan and a cross sectional view illustrating a second modification of the chemical cartridge according to the sixth form of implementation of the present invention.
Figure 48B:
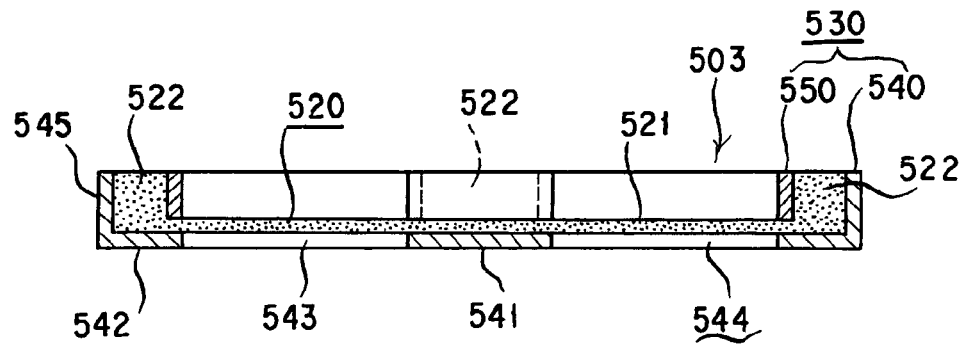

In a second modification as shown in FIGS. 48A and 48B, the chemical impregnated body 520 may have its high liquid retention region 522 located closer to the periphery of the carrier 521.

For example, the carrier 521 may have a plurality of high liquid retention regions 522 positioned circumferentially spaced apart from each other along a peripheral area thereof.

Figure 49:
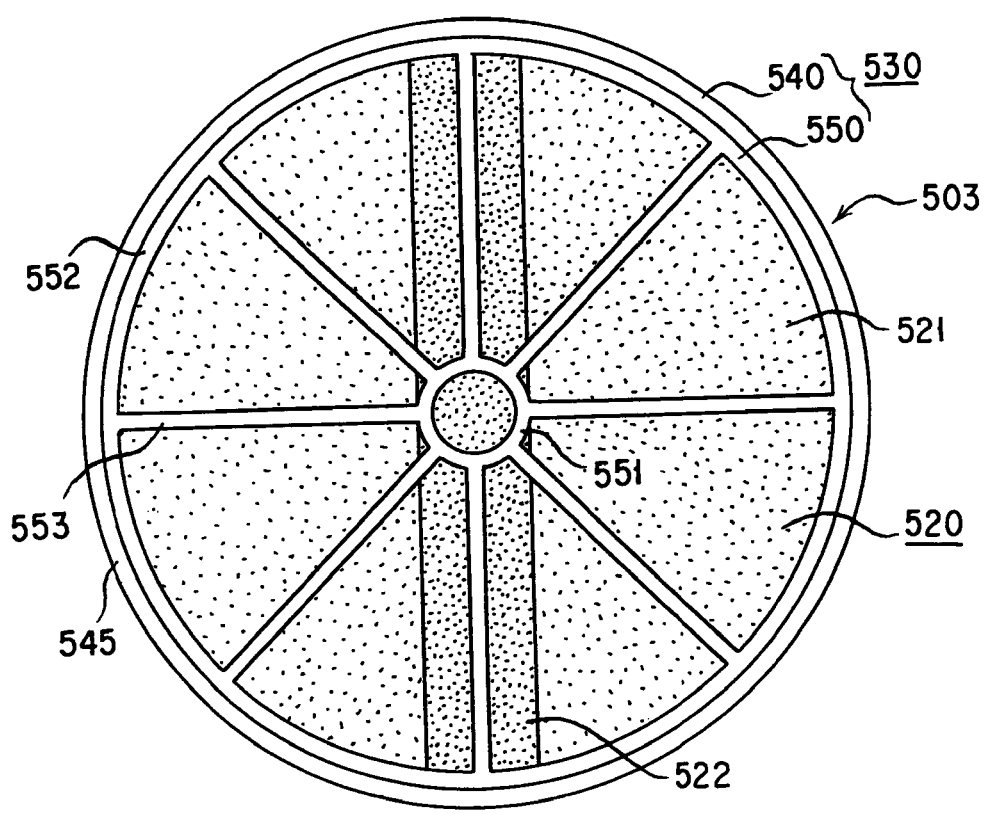
FIG. 49 is a top plan view illustrating a third modification of the chemical cartridge according to the sixth form of implementation of the present invention.
Figure 50:
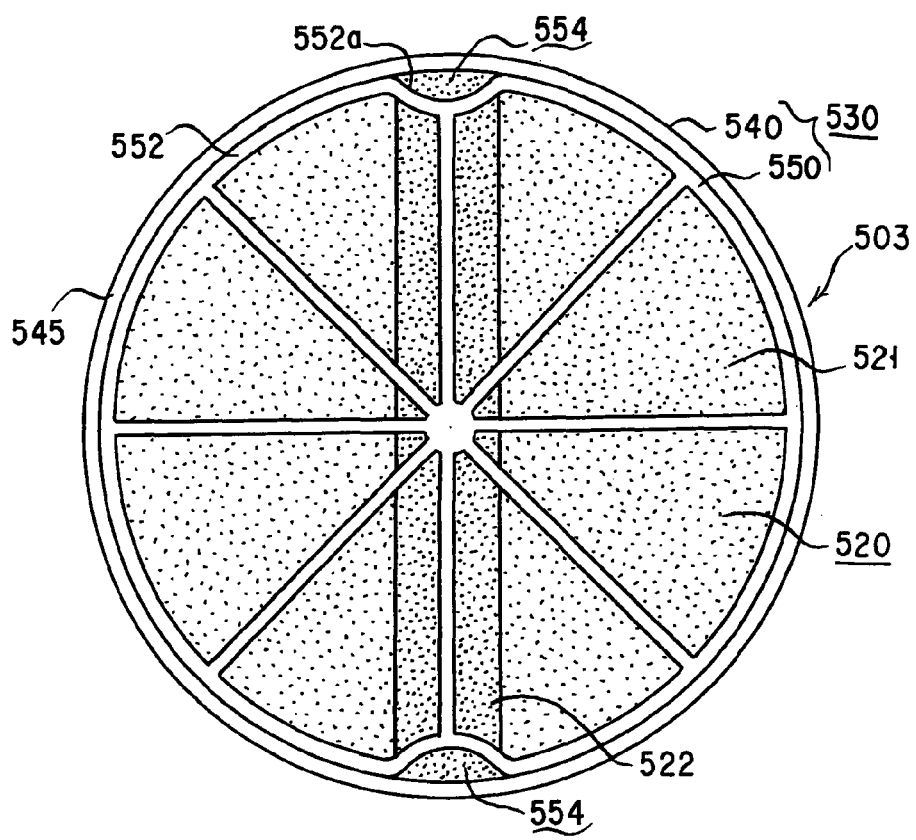
FIG. 50 is a top plan view illustrating a fourth modification of the chemical cartridge according to the sixth form of implementation of the present invention.

In a third and a fourth modification as shown in FIGS. 49 and 50, the high liquid retention region 522 of the chemical impregnated body 520 is in the form of a narrow band extending and continuous diametrically. The high liquid retention region 522 here is supplied with liquid chemical from the central region, such as the central ring 551, of the hold member 550 in the arrangement shown in FIG. 49 and from the peripheral region, such as openings 554 formed between the dents 552a of the peripheral ring 552 deformed of the hold member 550 and the ring-shaped raised edge 545 of the peripheral support section 542 of the receptacle body member 540 in the arrangement shown in FIG. 50. In further modifications not shown, a plurality of such band-shaped high liquid retention regions 522 may be formed and arranged in the form of a lattice, or one or more of such high liquid retention regions 522 may be positioned suitably as desired.

The high liquid retention region 522 of the chemical impregnated body 520 may be formed separately from the carrier 521 and may be laid above and/or below the carrier 521.

Figure 51:
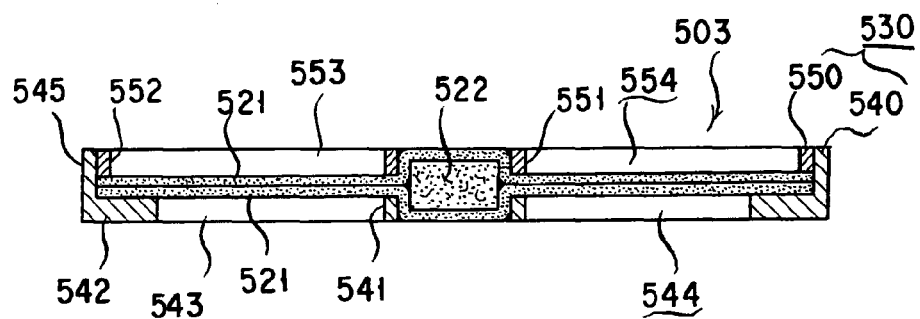
FIG. 51 is a cross sectional view illustrating a fifth modification of the chemical cartridge according to the sixth form of implementation of the present invention.

For example, in a fifth modification as shown in FIG. 51, a pair of carriers 521 are used to hold a high liquid retention region 522 between them.

Also, in a further modification not shown, the high liquid retention region as a separate body is fitted into the central ring 551 of the hold member 550 and thereby mounted while the hold member 550 is attached the receptacle body member 40 so as to bring the high liquid retention region 522 into contact with the carrier 521.

Alternatively, the carrier 521 may be laid on the high liquid retention region 522 mounted as a separate body on the central support section 541 of the receptacle body member 540.

Mention is next made of how the high liquid retention region 522 described above may specifically be implemented.

The high liquid retention region 522 as a separate body is formed of a same material or a material dissimilar to that of which the carrier 521 is formed, and is integrated with, or bonded to, seamed with, placed on or welded to the carrier 521.

Alternatively, a blank material is blown by special machining on a portion of the carrier 521 to make "metsuke" large to build up there a high liquid retention region 522.

The blank materials of which the carrier 521 of the chemical impregnated body 520 or the high liquid retention region 522 as a separate body in the present invention may be formed include natural and chemical fibers, nonwoven fabric (of natural, chemical and carbon fibers), resin net (polyester, polypropylene, polyvinyl chloride), cloth (woven or knitted), paper yarn (pulp, linter, synthetic paper). The material may be a formed body such in the form of a sheet, net, honeycomb, drain board, lattice or fold, a body yieldable to keep its shape when confined, or flocculate or sponge, and further foamed beads, foamed urethane, and wooden or bamboo charcoal.

Of these materials, a sheet-like material of nonwoven fabric that excels in air permeability and chemical retention is preferred.

In the present invention, ways in which to supply a liquid chemical into a high liquid retention region 522 may visually check an amount of its supply using a calibrated dropping pipette, a dosage ampule, a metered container or a container with a metering cup, or a nozzle.

Also, since in supplying a chemical it is convenient if the time of its re-supply can visually be checked, it is desirable to use a chemical impregnated body 420 that may be of known type with an indicator displaying the time of its depletion.

The chemical that can be impregnated into the carrier 521 of a chemical impregnated body 521 for use in the present invention may be an insect pest control agent (insecticide, repellent, growth inhibitor, miticide, insect control essential oil or the like), aromatic, aromatic deodorant, deodorant, fungicide, disinfectant or vermin repellent, and especially such a chemical that is volatile at an ordinary temperature or air flow conditions.

Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical carrier thin and small.

Further, not only is a chemical cartridge 503 according to the present invention used with a blower type chemical diffusing apparatus as described above, but also it can be directly attached to the fan in an air blower and may otherwise be integrated into the fan. Further, it can be disposed in either an air inlet or outlet side. Yet further, it can be attached at the blowout port of an air conditioner.

An explanation is next given of a seventh form of implementation of the present invention.

Figure 52:
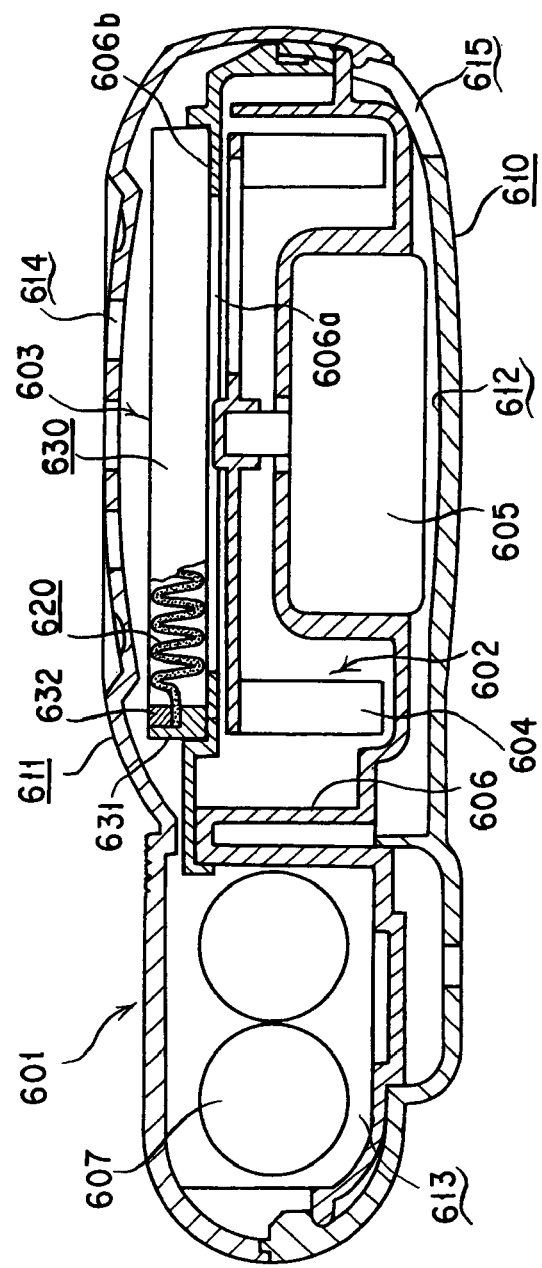
FIG. 52 is a cross sectional view illustrating a blower type chemical diffusing apparatus using a chemical cartridge that represents a seventh form of implementation of the present invention.

While with reference to FIG. 52 a chemical cartridge in another form of the present invention will, as an example of its use, be described as applied to a blower type chemical diffusing apparatus using a chemical cartridge to diffuse a chemical into an atmosphere, it will be understood that the present invention when applied is not limited to this particular use.

As shown in FIG. 52, a main casing body 601 is provided with an air blower 602 and has a chemical cartridge 603 removably attached thereto wherein a fan 604 of the air blower 602 is rotated by a motor 605 to pass air through the chemical cartridge 603.

The main casing body 601 includes a base member 610 and a cover member 611, is formed with a blower mounting section 612 and a battery accepting section 613 and has an air inlet section 614 and an air discharge section 615.

The air blower 602 has a fan 604 and a motor 605 mounted in a housing 606 provided in the blower mounting section 612. The housing 606 has an air inlet port 606a communicating with the air inlet section 614 and also has an air discharge port (not shown) communicating with the air discharge section 615.

A battery 607 shown as comprising two dry cells is attached into the battery accepting section 613.

The cover member 611 is so connected to the main casing body 610 that it can be opened and closed whereby opening the cover member 611 allows the chemical cartridge 603 and the battery 607 to be removed and fitted in.

The chemical cartridge 603 includes a chemical retainer or chemical impregnated body 620 and a fixture 630, although the chemical cartridge 603 is not limited to a combination of such a chemical impregnated body 620 and a fixture but may comprise a chemical impregnated body 620 and a receptacle that will be described later or may comprise only a chemical impregnated body 620.

The chemical impregnated body 620 as shown in FIGS. 52 to 56 is made of a porous or air permeable and liquid absorptive pleated sheet material 621 that is flat and impregnated with a chemical, as shown. A number of pleats of the chemical impregnated body 620 are formed by alternating mountain fold and valley fold of the sheet material at certain widths.

The chemical impregnated body 620 made of such a sheet material 621 which is thus large in surface area per unit volume and capable of retaining liquid chemical can retain a large amount of liquid chemical per unit volume and moreover can be enough if it is made small in size.

For example, it is possible to provide a thin chemical impregnated body 620 containing a large amount of liquid chemical.

This sheet 621 is prevented from losing its pleated shape by jointing, e.g. thermally fusing, ultrasonically fusing, and fusing by in-mold forming its peripheral edge 622, across which pleats are made parallel, to maintain a pitch of pleats. To it, if a pleated sheet is left with its pleats as they are, under an external force it tends to lose its shape and become unable to maintain its original pitch of plates.

So processed, the sheet material 621 allows air to pass uniformly over its entire area and in turn chemical to emanate from the chemical impregnated body 620 uniformly over its entire area.

This thus permits a volume of chemical retained in the chemical impregnated body to be consumed substantially uniformly over its entire area, thereby rendering the utilization of a chemical for this purse effective and efficient.

In the form of implementation illustrated, the chemical impregnated body 620 is round in its planar shape with its peripheral edge 622 in the form of a circular ring.

This does not exclude the possibility that the chemical impregnated body 620 may be square or rectangular in its planar shape; then two opposed edges of it may be fused.

The fixture 630 acts to hold the peripheral edge of the chemical impregnated body 620 to maintain its shape and prevent it from deforming. It also serves to enable the chemical cartridge 603 to be held by fingers while preventing chemical from contaminating the hand. Air is, of course, allowed to pass through the chemical impregnated body 620 except in its limited area where it is held by the fixture 630.

Thus, the fixture 630 has a hold section that holds the chemical impregnated body 620 and an air passage section through which air flows.

For example, the fixture 630 comprises a support member 631 and a hold member 632, and the support member 631 comprises a raised fitting ring 633 and, as a support element, a support ring 634 projecting inwards from an inner face 633a of the raised fitting ring 633 below it.

The hold section 632 is here in the form of a ring that can be fitted with a ring-shaped raised edge 633 of the support member 631.

Then, the chemical impregnated body 620 is loaded in the support member 631 with its peripheral edge 622 fitted with the raised fitting ring 633 and placed on the support ring 634, and thereafter the hold member 632 is fitted into the raised fitting ring 633 with itself pressed on the peripheral edge of the chemical impregnated body 620 to hold the same between the hold member 632 and the support ring 634 in the raised fitting ring 633 of the support member 631.

Thus, the ring-shaped support member 631 and the hold member 632 together constitute the abovementioned hold section and the space in the hold section constitutes the abovementioned air passage section.

Figure 56:
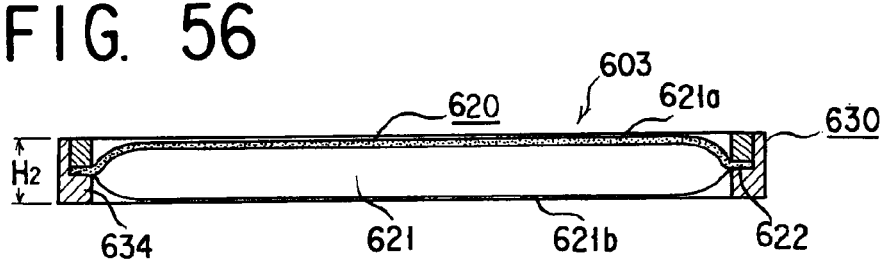
FIG. 56 is a cross sectional view of the chemical cartridge taken along the line LVI-LVI in FIG. 54.

In this form of implementation, as shown in FIG. 56 when the processed sheet material 621 is held by the fixture 630, it will be seen that its fused peripheral edge 622 is held lying at a position vertically midway of the height of the fixture 630 with its upper and lower contour lines 621a and 621b projecting upwards and downwards, respectively, to en equal extent from that vertically midway position.

Figure 57:
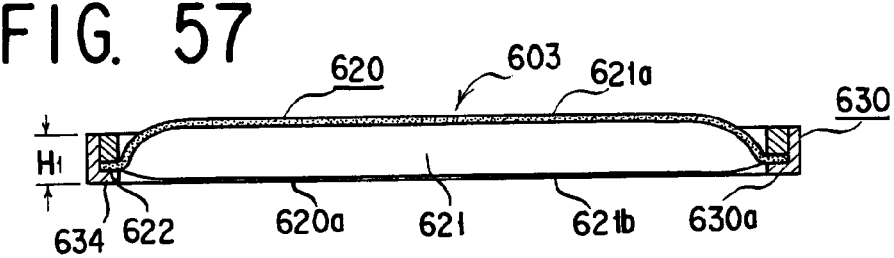
FIG. 57 is a cross sectional view illustrating a modification of the chemical cartridge shown in FIG. 55.

Depending on the relative thicknesses of the support and hold rings 634 and 632 that can be chosen, however, it is also possible to hold the fused peripheral edge 622 of the pleated sheet material 621 by the fixture 620 and as in a first modification shown in FIG. 57 to position the sheet material 621 in the fixture 630 such that its lower contour line 621b is relatively flat and its upper contour line 621a projects relatively largely upwards.

In any way, it is possible to make the lower face 620a of the chemical impregnated body 620 substantially flush and preferably precisely flush with the lower face 630a of the fixture 630, thereby improving the placeablility of the chemical cartridge 603 on the apparatus casing body 601. Also, since the support and hold rings 634 and 632 can be thin, it is possible make the fixture 630 small in thickness and size.

For example, it will be seen in the arrangement shown in FIG. 52 in which the chemical cartridge 603 must be placed on a shouldered top face 606b of the housing 606 that it is necessary to make the lower face 620a of the chemical cartridge 620 flush with the lower surface 630a of the fixture 630 in order to make the chemical cartridge 630 easily placeable on the housing 606. Otherwise, the height H2 of the fixture 630 for the chemical cartridge 603 shown in FIG. 56 tends to become larger than the height H1 of the chemical cartridge 603 shown in FIG. 57 by a thickness (height) of the support ring 634.

Being not only be air permeable but also liquid absorptive, the pleated sheet material 621 of the chemical impregnated body 620 after depletion of its chemical, namely once the chemical cartridge is used out by the fact that the amount of chemical I contains has been altogether diffused into the environmental atmosphere, can again be supplied and impregnated with chemical over its entire area to provide a chemical impregnated body.

Hence, a chemical cartridge is provided, which each time it is depleted can be reused repetitively upon refilling.

Figure 58:
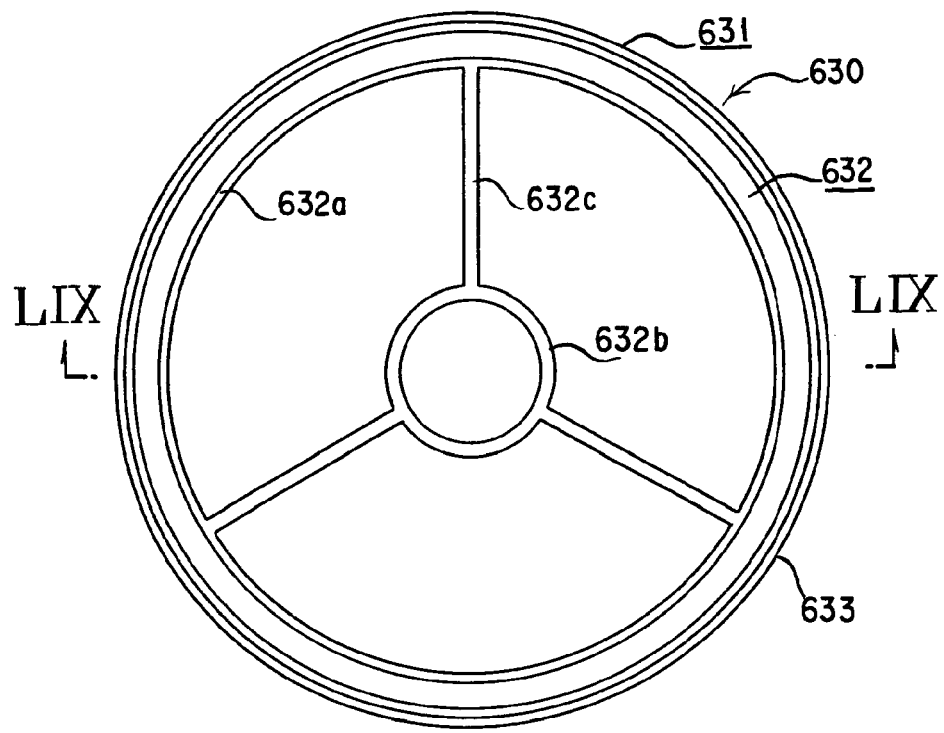
FIG. 58 is a plan view illustrating another form of the fixture that can be used in a chemical cartridge as shown in FIGS. 52 to 57.
Figure 59:
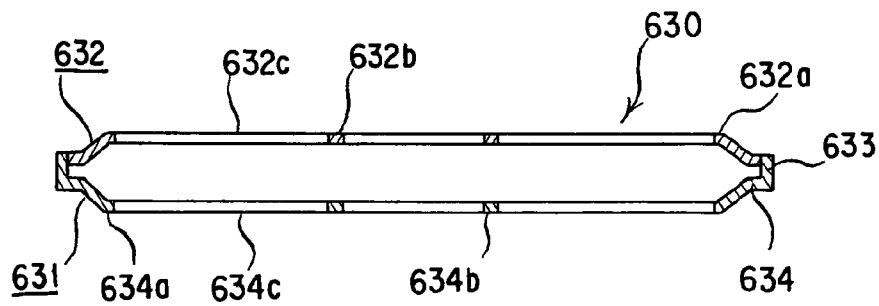
FIG. 59 is a cross sectional view of the fixture taken along the line LIX-LIX in FIG. 58.

Mention is next made of a preferred chemical cartridge that is suitable for refilling after depletion, reference being made to FIGS. 58 and 59.

The support element 634, illustrated above as the support ring, in the fixture 630 now comprises an outer and an inner peripheral ring 634a and 634b and connecting bars 634c that connect them together.

Likewise, the hold member 632 of the fixture now comprises an outer and an inner ring 632a and 632b and connecting bars 632c that connect them together.

With the cartridge so constructed, the chemical impregnated body 620 can be supplied with chemical into a region enclosed by the inner ring 632b and refilled easily.

With the fixture 630 shown in FIGS. 58 and 59, the chemical impregnated body 620 having its upper and lower faces supported by and between the inner rings 632b and 634b and the connecting bars 632c and 634c is prevented from its coming down. In this case, only one of the support and hold members 631 and 632 may have such an inner ring and connecting bars.

The inner rings are arbitrary in size, shape and number and can be determined according to the size of the chemical impregnated body 620, the material used for the pleated sheet and the amount of impregnation of chemical.

Providing an inner ring and connecting bars only for the support member 631 to form recesses on its upper face allows refilling liquid chemical to stay in these recesses and to be prevented from leaking and coming down.

Figure 54:
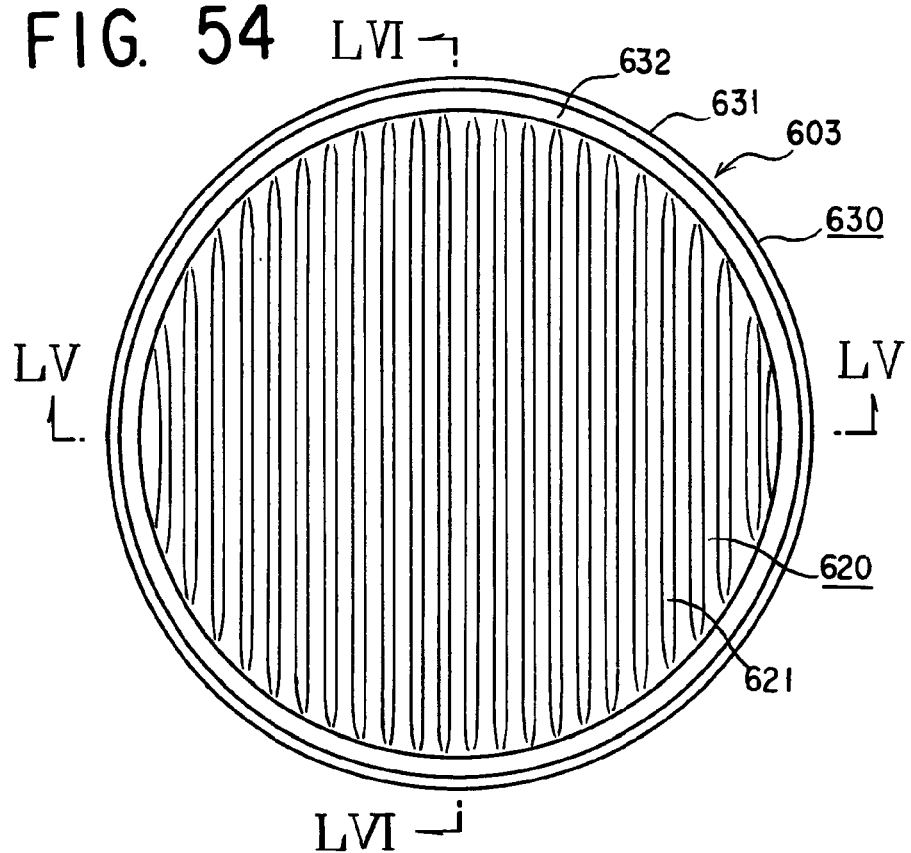
FIG. 54 is a top plan view of the chemical cartridge shown in FIG. 52.
Figure 55:
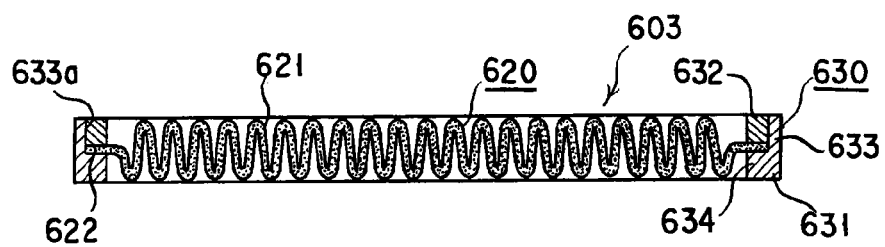
FIG. 55 is a cross sectional view of the chemical cartridge taken along the line LV-LV in FIG. 54.

Although not shown, an indication of refilling a chemical by a color or mark may be provided on a surface of the processed sheet material 621 in the chemical cartridge shown in FIG. 54.

Mention is next made of further modifications.

Figure 60:
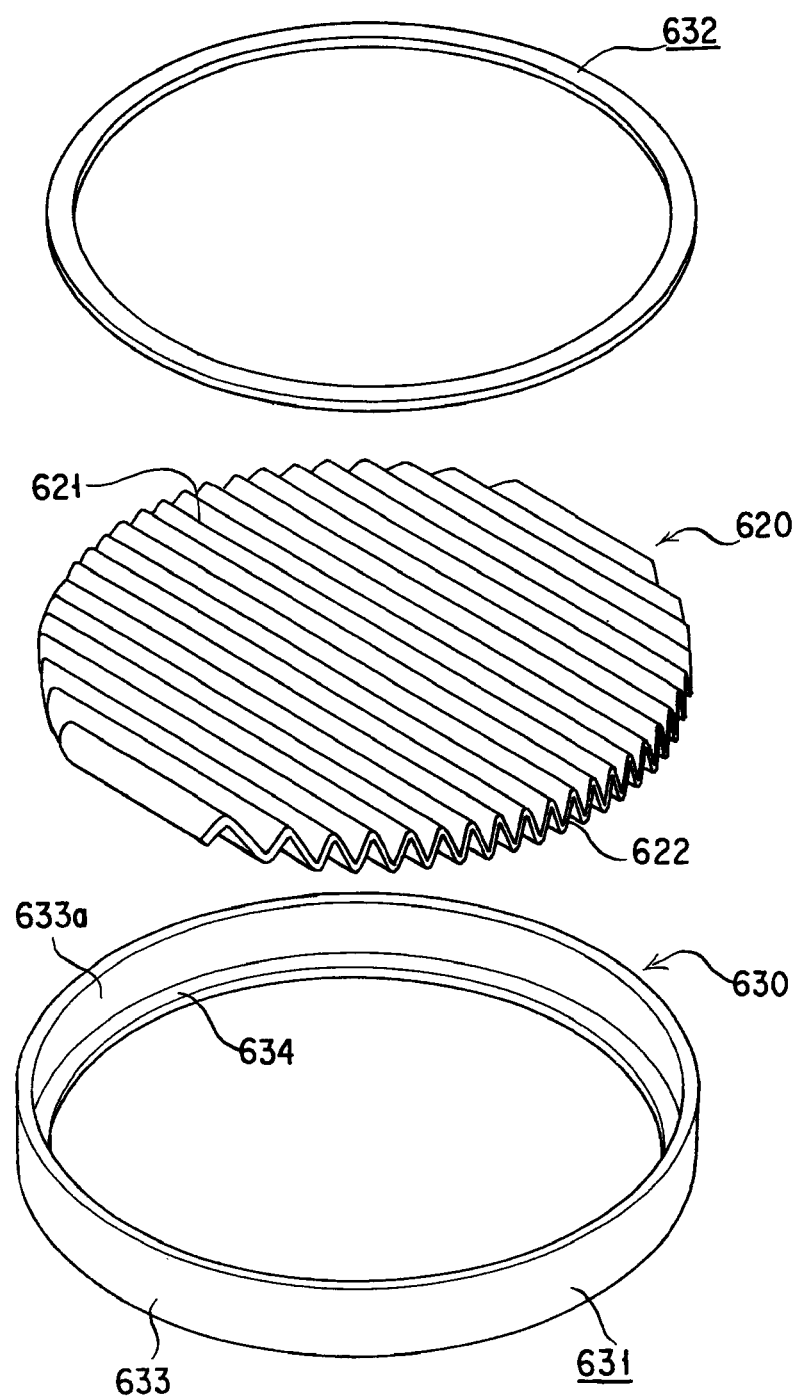
FIG. 60 is a decomposed perspective view illustrating a chemical cartridge having a chemical impregnated body different in shape.

As shown in FIG. 60, for the chemical impregnated body 620 a pleated sheet material 621 with its peripheral edge 622 that remains unprocessed (unfused) may also be used.

Then, the fixture 630 in holding the pleated sheet material 621 acts to squeeze its unprocessed peripheral edge 622, thereby holding the same firm to prevent the pleats from getting out of shape.

It may then be further desirable that the hold member 632 be threadedly engaged with the raised ring 633 of the support member 630 to hold the peripheral edge 622 of the pleated sheet material 621.

Figure 53:
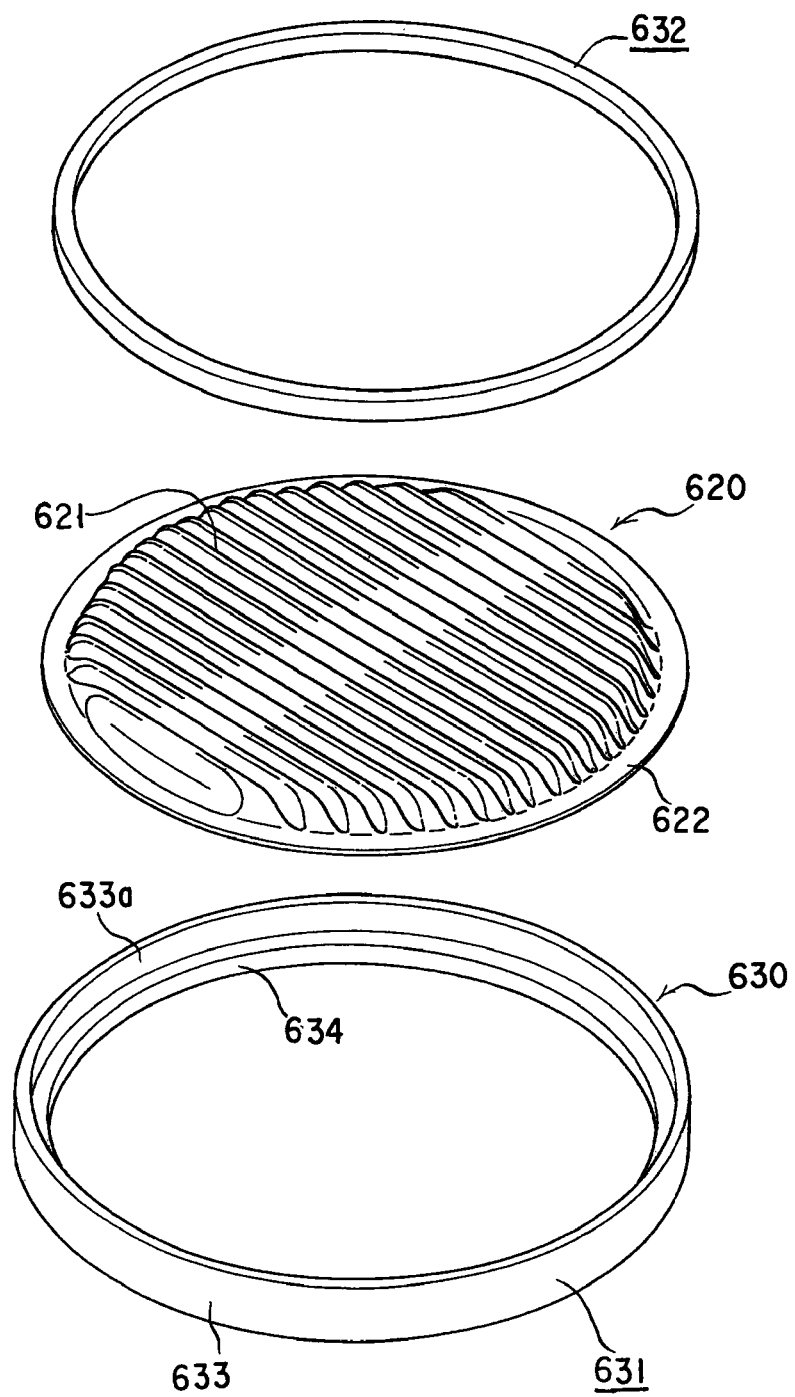
FIG. 53 is a decomposed perspective view of the chemical cartridge shown in FIG. 52.

A chemical cartridge may simply be a chemical impregnated body 620 with its peripheral edge 622 processed as shown in FIG. 53.

Incorporating a chemical impregnated body 620 into a receptacle 640 having an air passage region may provide a chemical cartridge 603.

Figure 61:
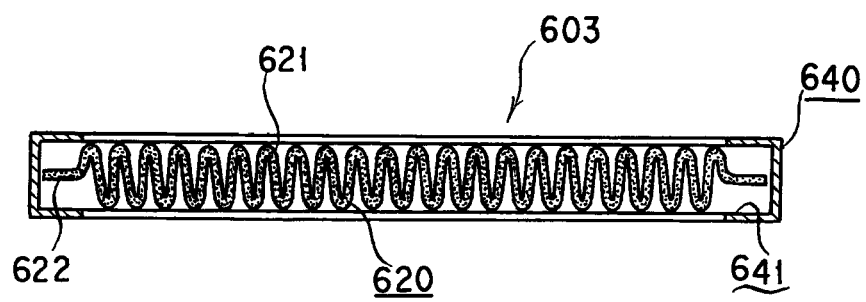
FIG. 61 is a cross sectional view illustrating a second modification of the chemical cartridge of the type shown in FIG. 52.

For example, in a second modification as shown in FIG. 61 a receptacle 640 in the form of a ring has its inner round area providing the air passage region and is formed with an inwardly facing annular recess 641 in its outer ring section. The processed peripheral edge 622 of the chemical impregnated body 620 is fitted into this annular recess 641 to incorporate the chemical impregnated body 620 in the receptacle 640.

Figure 62:
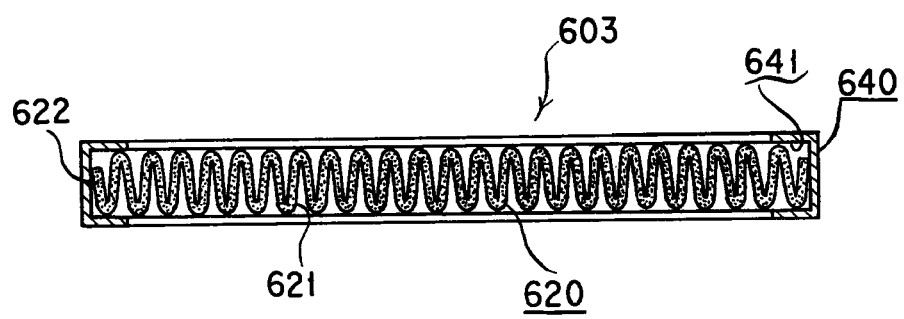
FIG. 62 is a cross sectional view illustrating a third modification of the chemical cartridge of the type shown in FIG. 52.

In a third modification as shown in FIG. 62, the unprocessed peripheral edge 622 of the chemical impregnated body 620 is fitted into this annular recess 641 to incorporate the chemical impregnated body 620 in the receptacle 640.

So constructed, the receptacle 640 can be held by a hand without causing the hand to be contaminated by chemical and is easy to handle.

While in the various examples of implementation mentioned above the chemical impregnated body 620 is shown to be round with the fixture 630 and the receptacle 640 being ring-shaped, the chemical impregnated body 620 may also be rectangular, triangular or semicircular with the fixture 630 and the receptacle 640 being then likewise rectangular, triangular or semicircular.

Thus, the fixture 630 will be enough if it is configured as being capable of holding and pressing the peripheral edge of a chemical impregnated body 620 and having an air passage region. Likewise, the receptacle 640 will be enough if it is configured as accommodating a chemical impregnated body 620 and having an air passage region.

While in the various examples of implementation mentioned above the chemical impregnated body 620 is shown to be planar to make the chemical cartridge thin, the chemical impregnated body 620 may be in the form of a cylinder and the receptacle 640 may be cylindrical having an annular hollow in which to receive the chemical impregnated body 620 to provide a chemical cartridge.

Figure 63:
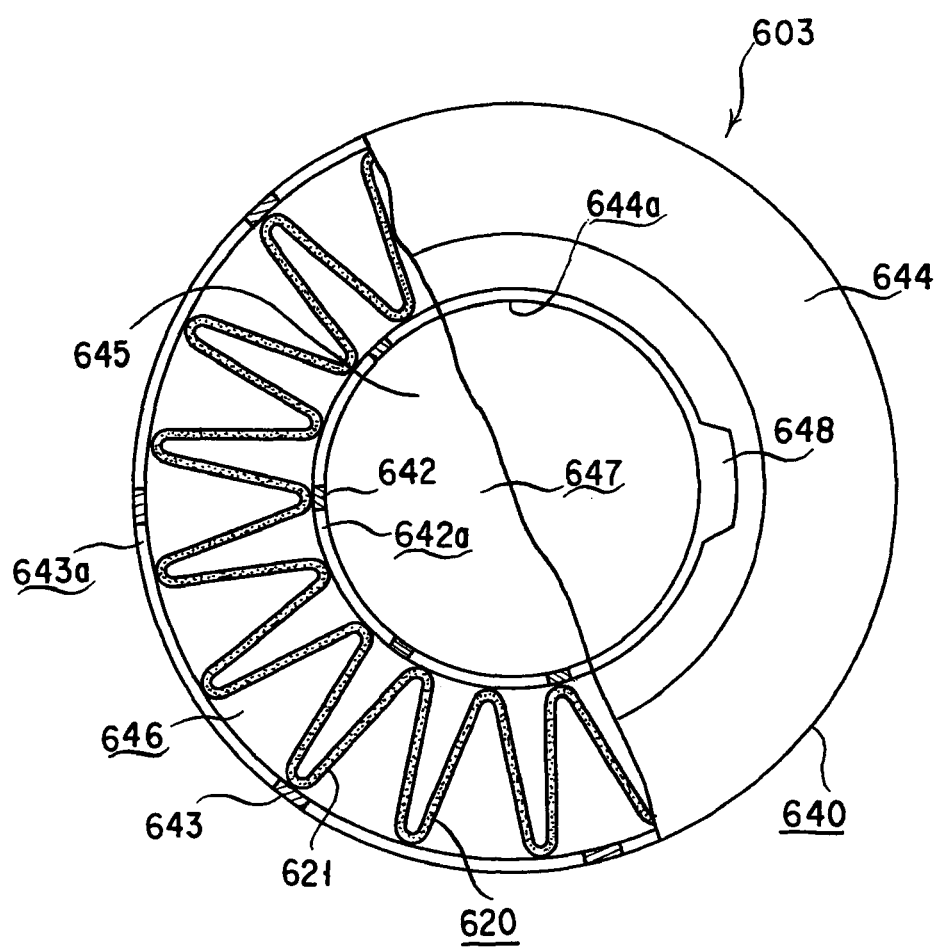
FIG. 63 is a cross sectional view illustrating a fourth modification of the chemical cartridge of the type shown in FIG. 52.
Figure 64:
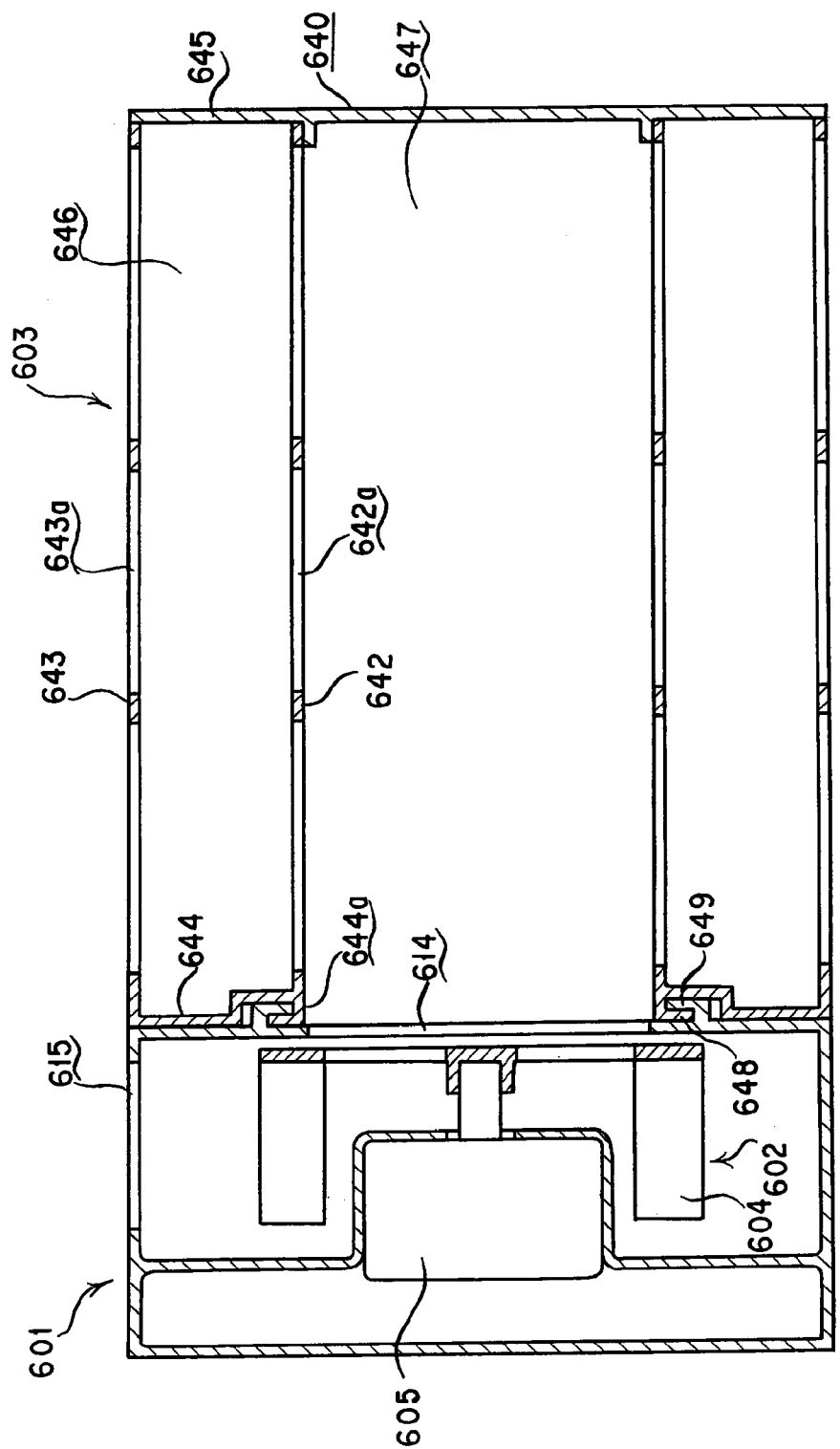
FIG. 64 is a cross sectional view illustrating an apparatus casing body and a receptacle using the chemical cartridge shown in FIG. 63.

For example, in a forth modification as shown in FIGS. 63 and 64, an inner and an outer cylinder 642 and 643 and a pair of end face plates 644 and 645 constitute a receptacle 640 having an annular hollow 646 and an axial hollow 647.

The inner and outer cylinders 642 and 643 are formed with vents 642a and 643a and one end face plate 644 has an airflow opening 644a.

The chemical impregnated body 620 here comprises a pleated sheet material 621 that is air permeable and liquid absorptive. This pleated sheet material 621 has its peak to valley height substantially equal to a radial width of the annular hollow 646 that is a difference in radius between the outer and inner cylinders 643 and 642 so it can be fitted in the latter. The pleated sheet material 621 is fitted so its pleat contours conform to opposed walls of the annular hollow 646, and then is impregnated with a liquid chemical.

The receptacle 640 thus loaded in its annular hollow 646 with the chemical impregnated body 620 provides a chemical cartridge 620.

The chemical cartridge 620 is removably loaded into the apparatus casing body 601.

For example, in the cartridge 603 the one end face plate 644 is formed with an outwardly projecting key element 648 where it defines the air passage opening 644a while in the apparatus casing body 601 is formed with an inward facing key recess 649 where it defines the air inlet opening 614 such that when the key element 649 engages the key hole 649 the chemical cartridge 603 and the apparatus casing body 601 are brought firm together while bringing the air passage opening 644a and the air inlet opening 614 into communication with each other.

And, with the fan 604 of the air blower 602 driven by the motor 605, air is allowed to flow through the vents 643a of the outer cylinder 643, the annual hollow 646, the vents 642a of the inner cylinder 642, the axial hollow 647, the air passage opening 644a, the air inlet section 614 and the air discharge section 615, thereby entraining chemical from the chemical impregnated body 620 therein for diffusion into the environmental atmosphere.

So constructed, adapted and arranged as mentioned above, a chemical impregnated body 620 as in the preceding forms of implementation can retain an increased amount of chemical per unit volume and can yet be made small in size.

According to this form of implementation, with a chemical impregnated body 620 that can retain an increased amount of chemical and can be reduced in diameter, a chemical cartridge 603 can be made small in diameter, yet having an increased chemical absorptivity.

Also, with a receptacle 640 made easy to handle and sealed, not only can it be handled easily, but also it does protect the user's hand from contamination with a chemical carried by a chemical impregnated body 620.

Further, although not shown partition plates may be provided in the annular hollow 646 of the receptacle 640 to prevent the pleats of the pleated sheet material 621 from getting out of shape. Yet further, the inner cylinder 642 may have a plurality of projections circumferentially spaced apart such that adjacent such projections hold the peak of each of the pleats to prevent the pleated sheet material 621 from getting out of shape.

While a chemical cartridge according to the present invention is shown above as mounted in the apparatus casing body 601 of a blower type chemical diffusing apparatus so that when blown by an air blower 602 it can emit chemical into the environmental atmosphere, it should be understood that the chemical cartridge in this aspect of the invention is not limited to such a particular use thereof but can simply be used with a suitable mounting means for placement in a living room or the like so that it can spontaneously emit chemical into the atmosphere.

In this case, the chemical cartridge may be made in the form of a fan, lantern, accordion or curtain.

The sheet for use to form a pleated sheet material 621 in the present invention is preferably made of a woven or nonwoven fabric to meet the requirements of its air permeability and liquid absorptivity. It is further desirable that the material be resistant to chemical depending on particular types of chemical used. For example, the raw materials applicable include pulse, cotton, wool, flax and silk as natural fiber, polypropylene, polyethylene, polyamide, polyethylene terephthalate, polybutylene terephthalate, polysulfone, rayon, methacrylate resin and glass fiber as synthetic fiber.

The pleated sheet material 621 should have as a sheet a thickness preferably ranging between 0.02 mm and 1.0 mm to keep its liquid absorptivity and retention.

Also, to facilitate chemical emission (air transmission), the sheet should preferably have a density of 0.05 to 1.0 g/cm$^3$.

While the fold width of the pleated sheet material 621 cannot be determined outright as it also relates to its fold-up width, where the object is to make the chemical cartridge smaller and especially thinner it cannot be desirable to increase the fold width since this tends to increase the thickness of chemical; it should thus be desirable to determine it depending on the area of the chemical impregnated body 620. Thus, the fold with should typically range between 2 mm and 30 mm.

In the case of a cylindrical chemical cartridge as shown in FIGS. 63 and 64, however, the pleated sheet material 621 may have a fold width in excess of 30 mm.

As to the peak to peak distance of pleats of the pleated sheet material 621 there appears to be no particular limitation imposed thereon. However, the wider the distance, the less the amount of chemical can be contained, and if the pleats are densified, an increase in the amount of chemical absorbed also impedes air flow and chemical emission. Thus, the distance should typically be mot more than 10 mm and not less than 1 mm (where the pleats when visually seen are barely contacting each other).

Not only can the pleats be even in height (where the fold width is equal to the fold-up width) but also they be irregular in height (where the fold width varies and the distance remains constant) or higher in their center. They may also be either straight or curved in center line. If their peripheries are thermally fused, a rounded periphery will result.

The materials of which the fixture 630 may be made include resins (polyethylene terephthalate, polypropylene, polyethylene, polyacetal, nylon, acryl, ABS and AS), synthetic paper materials and metals.

The volatile chemicals that can be used in the present invention include an insect pest control agent (insecticide, repellent, growth inhibitor, miticide, insect control essential oil or the like), aromatic, aromatic deodorant, deodorant, fungicide, disinfectant or vermin repellent, and especially such a chemical that is volatile at an ordinary temperature or air flow conditions. Such chemical may preferably be at least one insect pest control agent selected from such specific chemicals as methofluthrin, empenthrin, terallethrin, transfluthrin and profluthrin.

These chemicals are highly active and exhibit high deadly rates. Exhibiting efficaciousness in a small amount, they can desirably be used and can be the optimum for use in a chemical cartridge smaller in size.

In addition to a chemical as mentioned above, there may be added thereto where necessary a volatile adjustor (petrolatum, glycol etc), dissolving agent (paraffin, polyalcohol, fatty ester etc), antioxidant, (BHT, BHA etc), indicator (allochroic coloring agent) and ultraviolet absorber.

As mentioned above, ways in which to re-supply a liquid chemical into a chemical cartridge used out may visually check an amount of its supply using a calibrated dropping pipette, a dosage ampule, a metered container or a container with a metering cup, or a nozzle.

Also, since in supplying a chemical it is convenient if the time of its re-supply can visually be checked, it is desirable to use a chemical impregnated body 620 that may be of known type with an indicator displaying the time of its depletion.

An explanation is next made of an eight form of implementation of the present invention.

Figure 65:
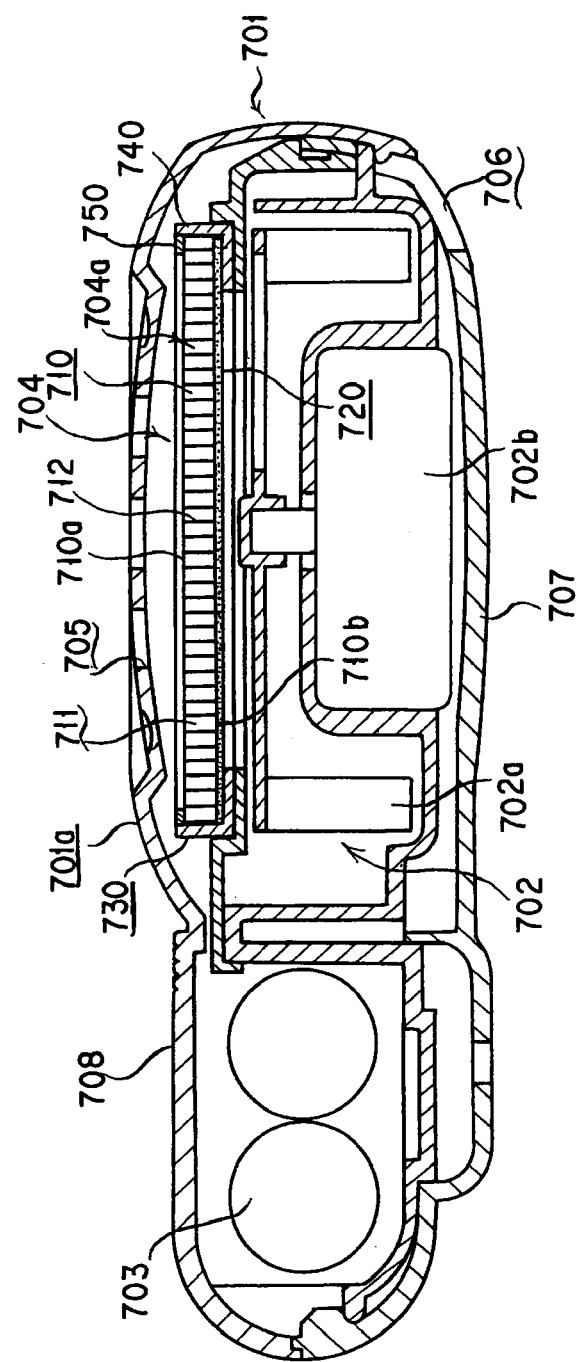
FIG. 65 is cross sectional view illustrating a blower type chemical diffusing apparatus using a chemical cartridge that represents a eighth form of implementation of the present invention.

Referring to FIG. 65, there is shown a blower type chemical diffusing apparatus using a chemical impregnated body according to the present invention to diffuse chemical volatilizing therefrom into the environmental atmosphere.

In the apparatus shown, an apparatus or main casing body 701 has an air blower 702, a battery 703 and a chemical cartridge 704 including a chemical impregnated body 704 accommodated therein, wherein with a fan 702a rotated by a motor 702b, air is drawn through an air inlet port 705, passes through the chemical impregnated body 704a and is discharged through an air discharge port 706 to emit chemical volatilizing from the chemical impregnated body 704a and carried in air into the environmental atmosphere.

The apparatus casing body 701 has a portion 701a opposed to the chemical cartridge 704 where the latter can be detached and attached.

Made of a base member 707 and a cover member 708, the apparatus casing body 701 is here designed, for example, to allow the cover member 708 to be opened and closed and the user to open the cover member 708 to remove the chemical cartridge 704 and the battery 703 and to fit them in position.

The chemical impregnated body 704a comprises a honeycomb body 710 and an air permeable and liquid absorptive sheet body 720 which are impregnated with a chemical.

The honeycomb body 710 has a large number of cores 711 which are open at its both side faces 710a and 710b in the direction its thickness.

The sheet body 720 is laid at one of these side faces, preferably at the side, 710b, where air flows out, over the side face.

Preferably, the honeycomb body 710 is much smaller in thickness than in width and length, namely a thin and "flat" body that is large in planar area, having a large number of cores 711 open in the direction of its thickness, and over that large area the sheet body 720 is laid at its side where air flows out.

The cores 711 of the honeycomb body 710 may in cross section be not only polygonal but also be, for example, corrugated, circular, triangular, square or triangular.

Further, the cores 711 may not only be laminar but also be spiral. The cores 711 may be formed of a material that can be any of those of which the sheet body 729 may be formed as will be mentioned below.

These features make it possible to make the chemical cartridge 704 thin and hence the apparatus casing body 701 small in thickness.

Further, reinforced by the honeycomb body 719, the sheet body 720 can keep its given shape.

The honeycomb body 710 also permits air to flow through it smoothly and can effectively emit the chemical it retains into the environmental atmosphere without impeding the air flow through the sheet body 720 it reinforces.

Also, being mounted on the apparatus casing body 701 as shown in FIG. 65, the honeycomb body 710 and the sheet body 720 allow air to pass and flow through them, permitting the chemical held in them to be carried on air to emanate and diffuse into the environmental atmosphere as the fan 702a is rotated as mentioned above.

Also, the honeycomb and sheet bodies 710 and 720 of chemical impregnated body 704a upon depletion of the chemical they have retained can be removed as the chemical impregnated body 704a from the apparatus casing body 701, placed in the state that the sheet body 720 lies above the honeycomb body 710 and refilled with the chemical. In this case, the sheet body 720 is supplied with liquid chemical by dropping liquid chemical at a limited area thereof, the liquid chemical being then permeated progressively over the entire sheet body 720 and at the same time permeated into and through the honeycomb body 710 progressively over the entire honeycomb body 710 as well. There thus results a chemical impregnated body 704*a* refilled.

More specifically, since the sheet body 720 is disposed to lie over an entire area in which a large number of walls 712 lie constituting the cores 711 of the honeycomb body 710 and oriented in the direction of its thickness, the chemical is retained upon impregnation or flooding on, along and into these walls 712.

Such a chemical cartridge 704 including a chemical impregnated body 704*a* on reloading in the apparatus casing body 701 is allowed to emit chemical into the environmental atmosphere.

Chemical refilling by dropping liquid chemical on the sheet body 720 allows chemical to be impregnated into and retained by the honeycomb body 710 over its entire volume as well. Since the amount of chemical for refilling the sheet body 720 may be commensurate to that needed to impregnate the honeycomb and sheet bodies 710 and 720, it is possible to avoid waste of chemical.

It is therefor possible for the user to easily regenerate a chemical impregnate body 704*a* after use by refilling the honeycomb and sheet bodies 710 and 720 with chemical.

With the sheet body 720 disposed in intimate contact with one of the side faces (e.g., side face 710*b*) of the honeycomb body 710 in the direction of its thickness, the chemical supplied into the sheet body 720 is allowed to smoothly permeate into and throughout the honeycomb body 710 (i.e. the wall materials 712).

With the sheet and honeycomb bodies 720 and 710 so arranged, chemical is allowed to permeate from the sheet body 720 to the honeycomb body 710 (i.e. wall materials 712) smoothly and without fail.

In this form of implementation, a retainer receptacle 730 is used to bring the sheet body 720 into intimate contact with one side face (e.g., side face 710*b*) of the honeycomb body 710.

The retainer receptacle 730 comprises a receptacle body member 740 and a hold member 750 each of which is in the form of a ring. The chemical impregnated body 704*a* is put into the retainer receptacle 740, and the hold member 750 is fitted into and coupled with the receptacle body member 740 to hold the honeycomb and sheet bodies 710 and 720 by and between them with the sheet body 720 lying in intimate contact with the one side face of the honeycomb body 710.

This arrangement allows the sheet material 720 to come into intimate contact firmly with one side face of the honeycomb body 710.

Figure 66:
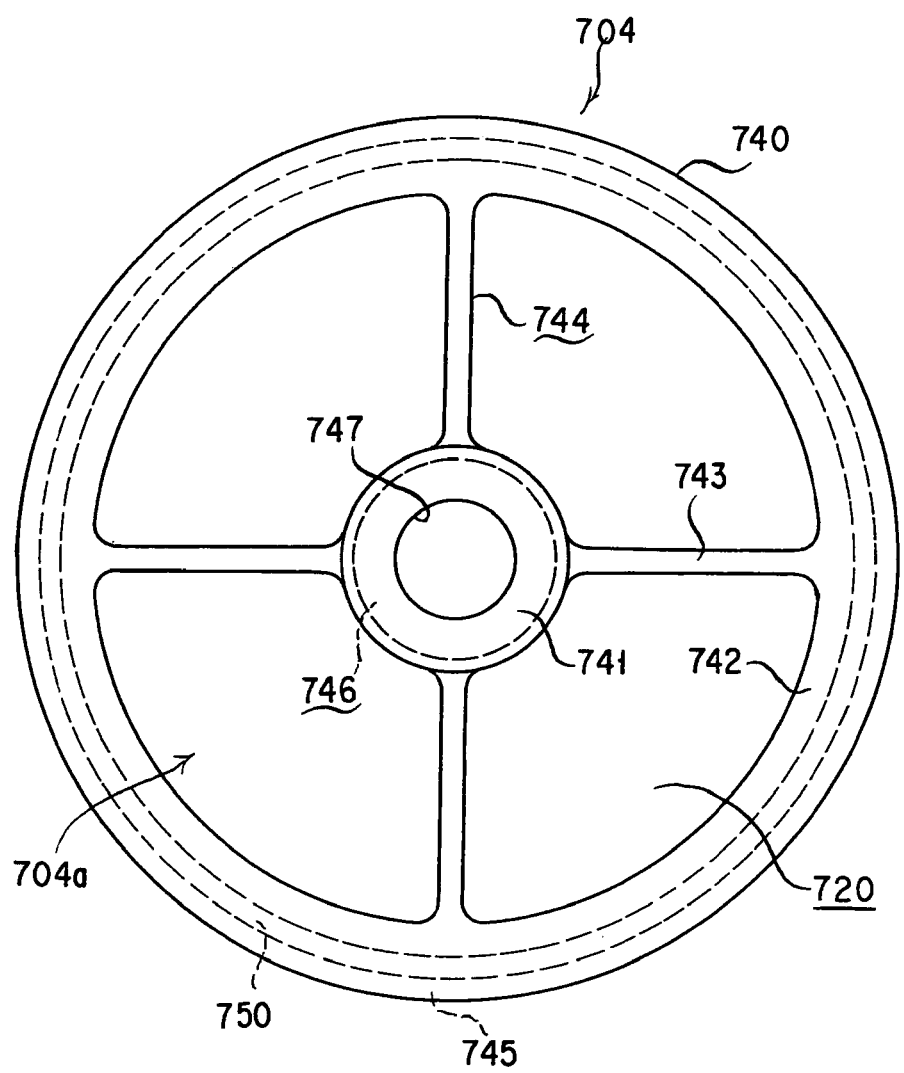
FIG. 66 is a bottom plan view of a first modification of the chemical cartridge shown in FIG. 65.
Figure 67:
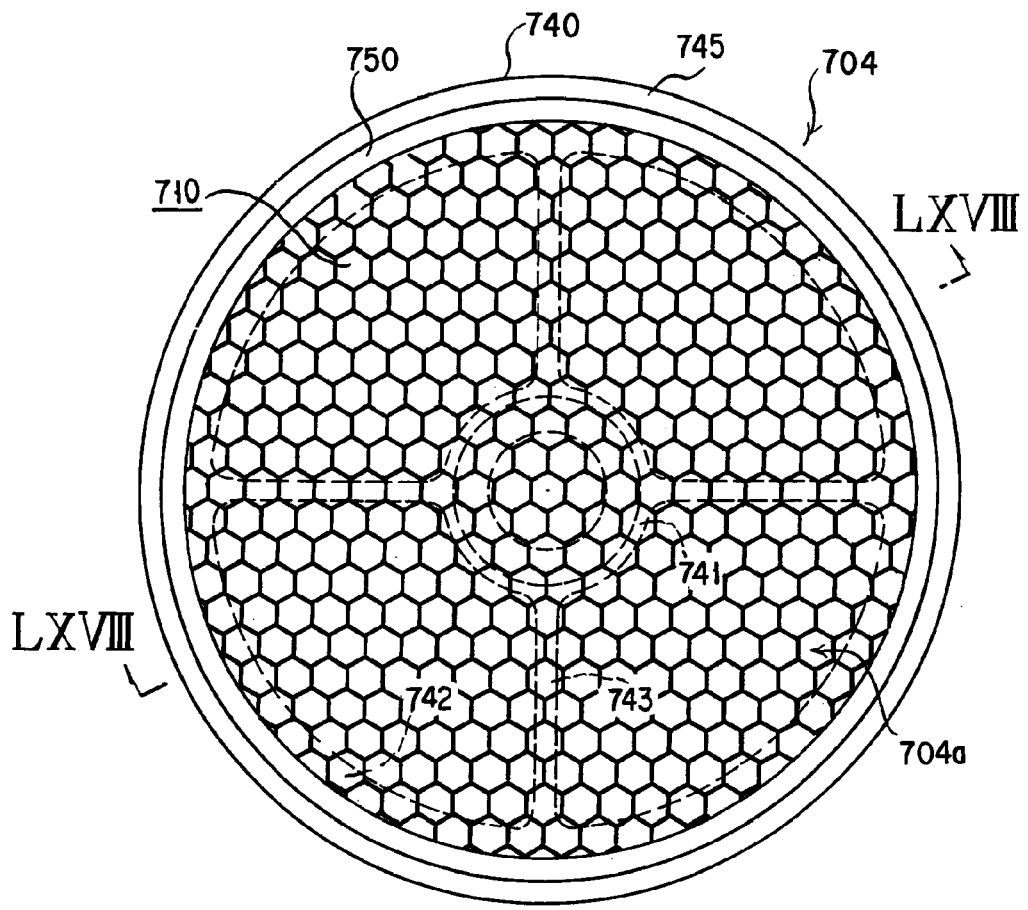
FIG. 67 is a top plan view of the chemical cartridge shown in FIG. 66.
Figure 68:
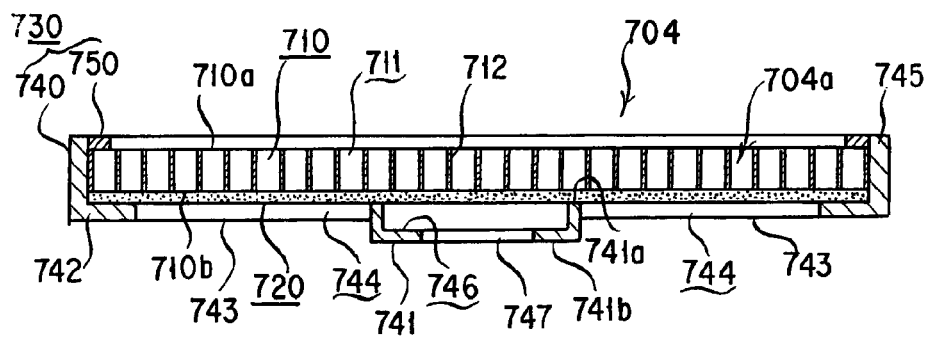
FIG. 68 is a cross sectional view of the chemical cartridge taken along the line LXVIII-LXVIII in FIG. 67.

Mention is next made of a first modification of the chemical cartridge 704 including the chemical impregnated body 704*a* with reference to FIGS. 66 to 68.

The receptacle body member 740 comprises a central support section 741, a peripheral support section 742 and a plurality of stays 743 connecting the central and peripheral support sections 741 and 742 together wherein a space defined with the central support section 741, the peripheral support section 742 and neighboring stays 743 connected together by the peripheral support section 742 is open constituting an air flow section 744 and the peripheral support section 742 has a raised support ring 745 made integral therewith.

The hold member 750 is in the form of a ring that can be fitted with the raised ring 745.

The honeycomb body 710 is fitted in the raised support ring 745 and the sheet body 720 is and placed on and supported by the upper surfaces of the central and peripheral support sections 741 and 742 and the stays 743 in contact therewith.

The hold member 750 is fitted with the raised support ring 745 and, coming into contact with a peripheral edge of the one side face 710*a* of the honeycomb body 710, holds such peripheral areas of the honeycomb and sheet bodies 710 and 720.

The central support section 741 is formed with a liquid chemical pool section 746 open in a support face 741, which section is open to the outside through an inlet port 747 formed at its side opposite to the support face 741.

In this arrangement, the chemical cartridge 704 (the retainer receptacle 730) is taken out and placed upon turning it upside down.

And, chemical is dropped and supplied through the inlet port 747 into the liquid chemical pool section 746 and pooled there.

This allows liquid chemical to permeate from the center of the of the sheet body 720 progressively over its entire area and at the same time to permeate from the sheet body 720 through the face of the honeycomb body 720 in intimate contact with the sheet body 720, then into and through the sheet body 720 progressively over its entire area as well.

Mention is next made of a second modification of the chemical cartridge 704 including the chemical impregnate body 704*a*.

Figure 69:
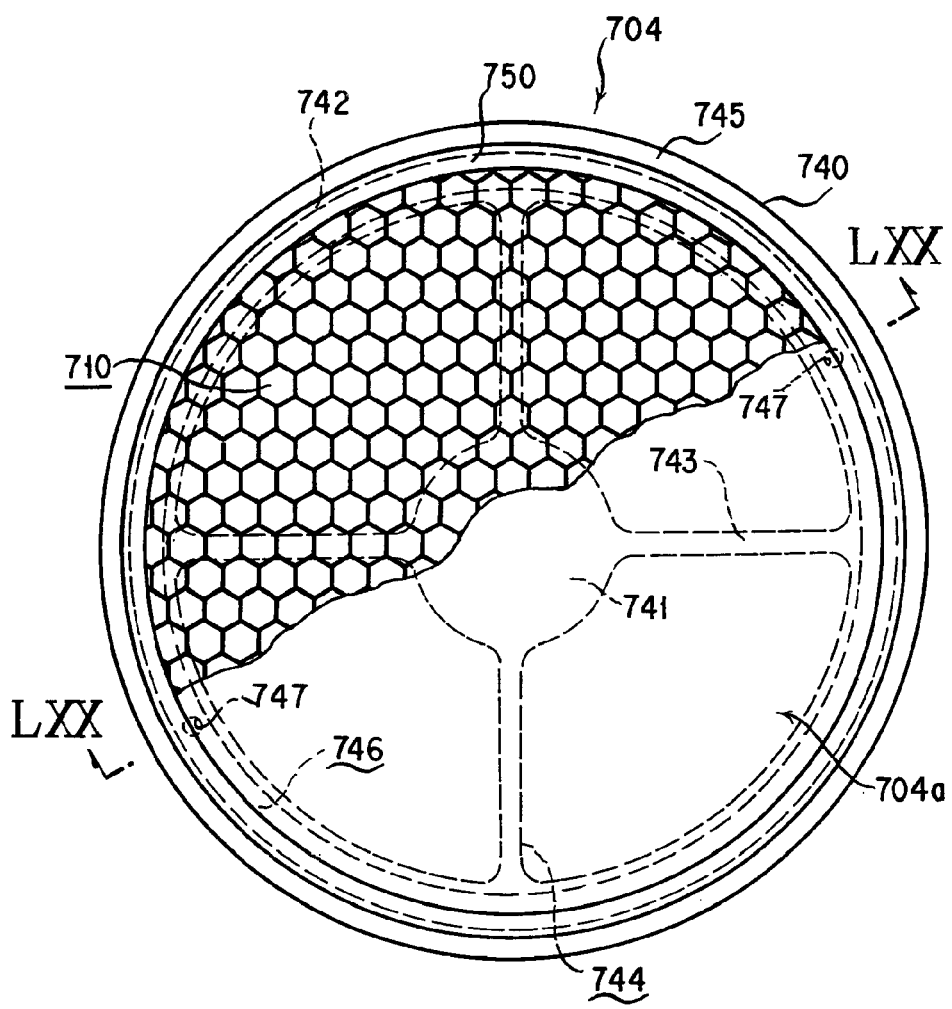
FIG. 69 is a top plan view
Figure 70:
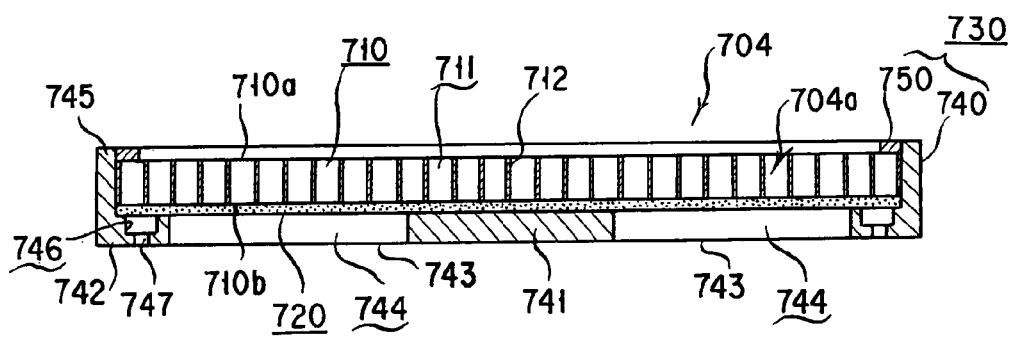
FIG. 70 is a cross sectional view of the chemical cartridge taken along the line LXX-LXX in FIG. 69.

As shown in FIGS. 69 to 70, the peripheral support section 742 of the receptacle body member 740 is formed in its support face 742*a* with an annular liquid chemical pool section 746 that is open in its lower face through an inlet port 747.

In this arrangement, liquid chemical is supplied into a peripheral part of the sheet body and is allowed to permeate towards its central part.

Mention is next made of a third modification of the chemical cartridge 704 including the chemical impregnate body 704*a*.

Figure 71:
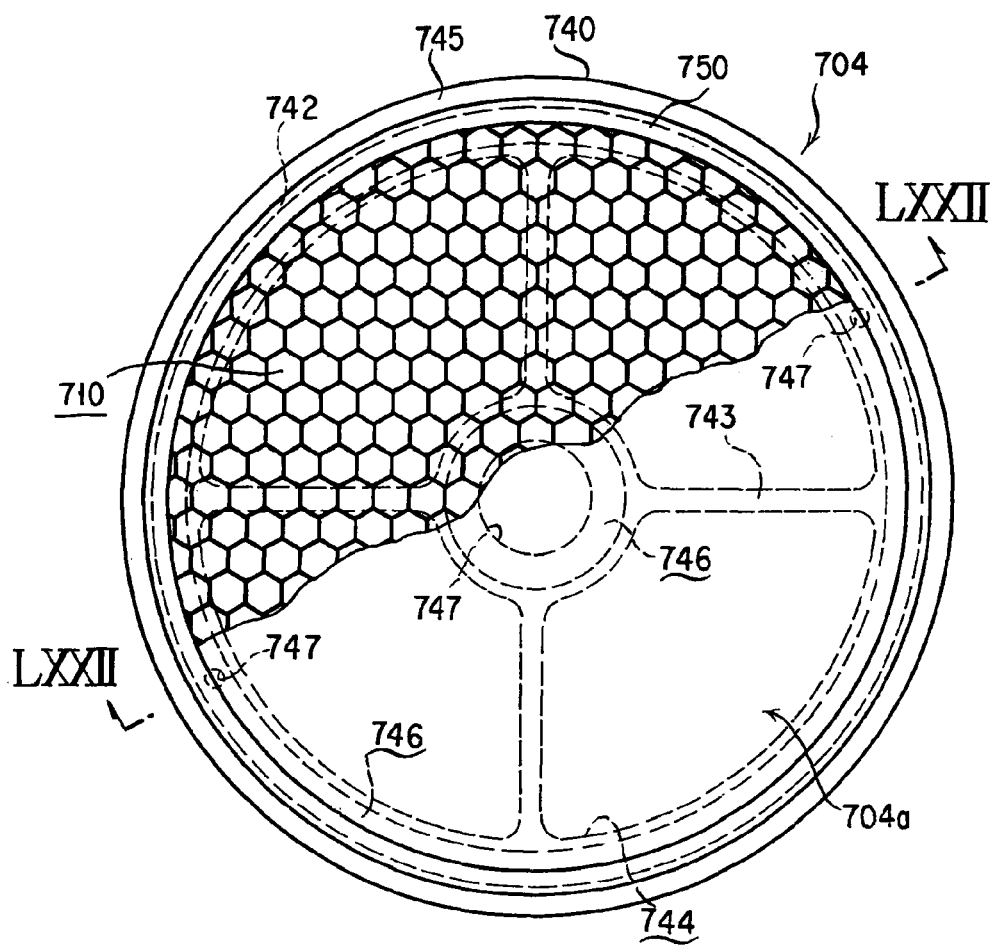
FIG. 71 is a top plan view of a third modification of the chemical cartridge shown in FIG. 65.
Figure 72:
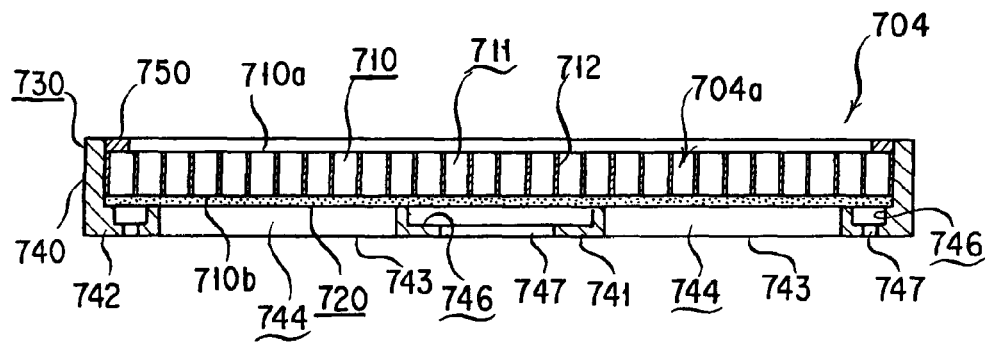
FIG. 72 is a cross sectional view of the chemical cartridge taken along the line LXXII-LXXII in FIG. 71.

As shown in FIGS. 71 and 72, the receptacle body member 740 is formed in each of the central and peripheral support sections 741 and 742 with a liquid chemical pool section 746 and an inlet port 747.

In this arrangement, liquid chemical is supplied into both a central and a peripheral part of the sheet body 720 so that chemical is allowed to permeate both its peripheral and central parts. This allows chemical to fill the honeycomb body 710 efficiently in a short period of time.

While the sheet body 720 is shown above to lie above the honeycomb body 710 to supply liquid chemical directly on the sheet body 720, alternatively the sheet body 720 may be positioned below the honeycomb body 710 so that liquid chemical is supplied from above the honeycomb body 710 into the cores 711 and then supplied into the sheet body 720.

In this case, both the need to form the inlet port 747 shown in FIGS. 68 and 72 and the need to make the liquid chemical pool section 746 deep as shown in FIGS. 68 and 72 are eliminated.

Figure 73:
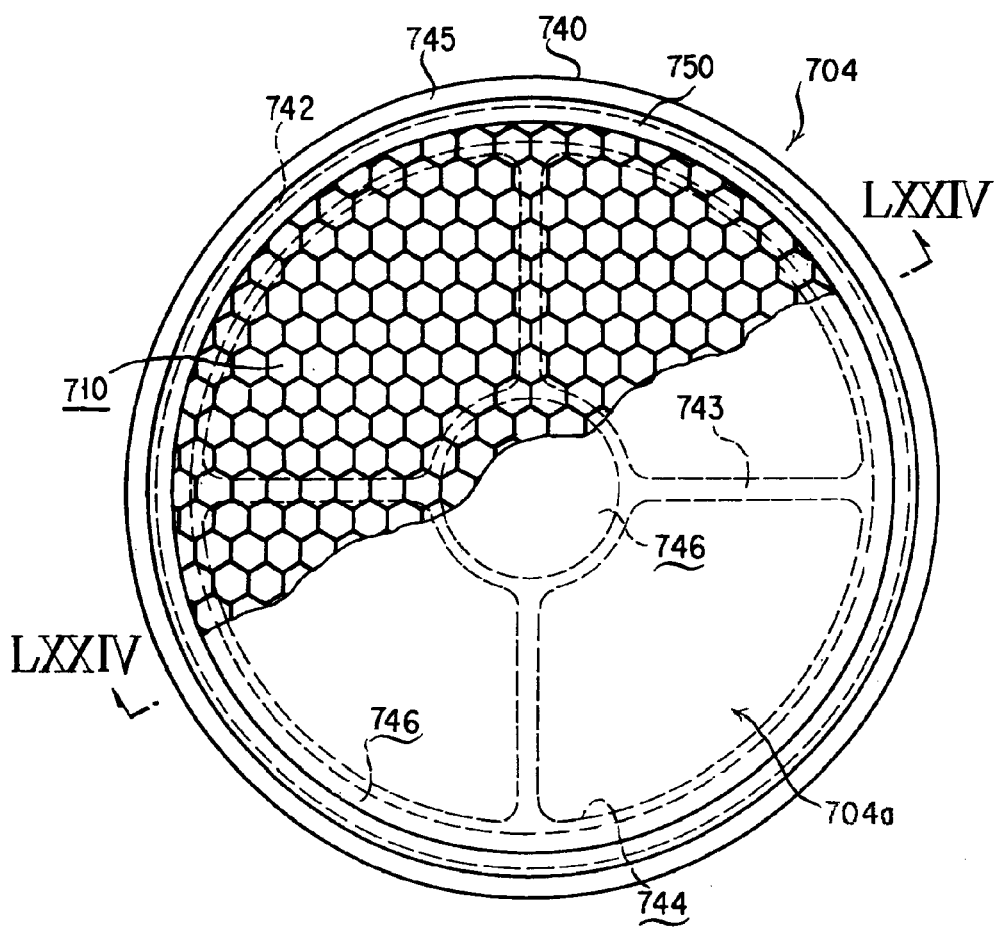
FIG. 73 is a top plan view of a fourth modification of the chemical cartridge shown in FIG. 65.
Figure 74:
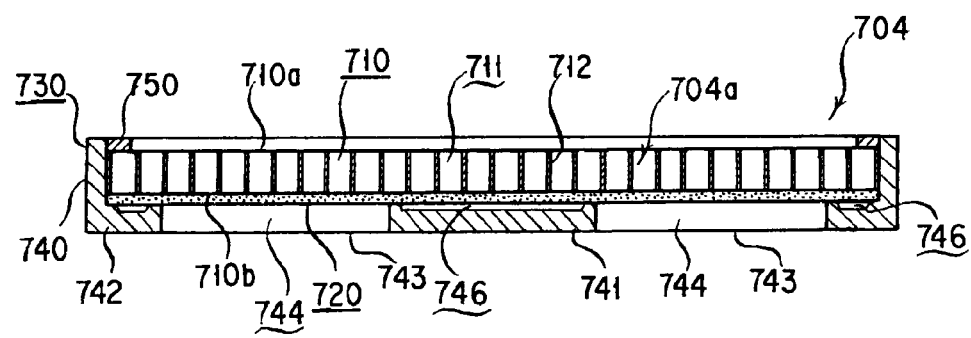
FIG. 74 is a cross sectional view of the chemical cartridge taken along the line LXXIV-LXXIV in FIG. 73.

For example, in a fourth modification as shown in FIGS. 73 and 74, a shallow liquid chemical pool section 746 is formed in each of the central and peripheral support sections 741 and 742.

And, liquid chemical is supplied from the cores 711 both in the central and peripheral parts of the honeycomb body 710 into the central and peripheral parts of the sheet body 720.

Also, to identify where the chemical can be supplied, a ring collar may be applied on a hold section opposed to the liquid chemical pool section to indicate that the chemical should be supplied there. Alternatively, a color may be applied as an indication to those cores where the chemical should be supplied.

While in the preceding examples of implementation, the chemical impregnated body 704a is shown mounted so that the sheet and honeycomb bodies 720 and 710 lie inside and outside, respectively, they may be positioned vice versa, i.e., to lie outside and inside, respectively.

For example, depending on types of chemicals used, the sheet body 720 may be positioned to face outwards and the honeycomb body 710 to face inwards.

Also, while in the above examples of implementation, the chemical impregnate body 704a is shown having a sheet body 720 disposed to lie in intimate contact with one side face of a honeycomb body 710, two sheet bodies 720 may be used to lie in intimate contact with the two opposite side faces of a honeycomb body 710, respectively.

The chemical that can be impregnated into a honeycomb body 710 of a chemical impregnated body 704a for use in the present invention may be an insect pest control agent (insecticide, repellent, growth inhibitor, miticide, insect control essential oil or the like), aromatic, aromatic deodorant, deodorant, fungicide, disinfectant or vermin repellent, and especially such a chemical that is volatile at an ordinary temperature or air flow conditions.

Such chemicals, if used to kill insects, may be a variety of volatile insecticides so far known, of which pyrethroid, carbamate, organophosphorus chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical impregnated body thin and small.

The blank materials of which a sheet body 720 may be formed include natural and chemical fibers, nonwoven fabric (of natural, chemical and carbon fibers), resin net (polyester, polypropylene, polyvinyl chloride), cloth (woven or knitted), paper yarn (pulp, linter, synthetic paper). The material may be a formed body such in the form of a sheet, net, honeycomb, drain board, lattice or fold, a body yieldable to keep its shape when confined, or flocculate or sponge.

Of these materials, a sheet-like material of nonwoven fabric that excels in air permeability and chemical retention is preferred.

In the present invention, ways in which to supply a liquid chemical into a chemical impregnate body may visually check an amount of its supply using a calibrated dropping pipette, a dosage ampule, a metered container or a container with a metering cup, or a nozzle.

Also, since in supplying a chemical it is convenient if the time of its re-supply can visually be checked, it is desirable to use a honeycomb body 710 in a chemical impregnated body 704 that may be of known type with an indicator displaying the time of its depletion.

What is claimed is:

1. A chemical cartridge, comprising:
a chemical-impregnated body comprising an air-permeable and liquid-absorptive sheet impregnated with a chemical; and
a retainer receptacle which contains the chemical-impregnated body;
wherein:
the retainer receptacle comprises a central liquid pool recess formed at a central area of the retainer receptacle such that a liquid chemical stored in the central liquid pool recess is permeable towards a peripheral area of the sheet;
the retainer receptacle further comprises a peripheral liquid pool recess formed at a peripheral area of the retainer receptacle, the peripheral liquid pool recess being independent from said central liquid pool recess, and wherein a liquid chemical stored in the peripheral liquid pool recess is permeable towards a central area of the sheet;
the retainer receptacle comprises a receptacle base member and a cover member;
said receptacle base member comprises a central support section, a peripheral support section, a plurality of connecting sections connecting the central and peripheral support sections to each other, and a first airflow passage section defined by said support and connecting sections;
said cover member comprises a central hold section, a peripheral hold section, a plurality of connecting sections connecting the central and peripheral hold sections to each other, and a second airflow passage section defined by said hold and connecting sections;
said central liquid pool recess is formed in said central support section and a supply port communicating with said central liquid pool recess is formed in said central hold section; and
said peripheral liquid pool recess is formed in said peripheral support section and a peripheral supply section communicating with said peripheral liquid pool recess is formed in said peripheral hold section.

* * * * *